(12) United States Patent
Armani et al.

(10) Patent No.: US 8,637,662 B2
(45) Date of Patent: Jan. 28, 2014

(54) ISOXAZOLIDINE DERIVATIVES

(75) Inventors: Elisabetta Armani, Parma (IT); Eleonora Ghidini, Parma (IT); Ilaria Peretto, Parma (IT); Andrea Virdis, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 16 days.

(21) Appl. No.: 12/878,113

(22) Filed: Sep. 9, 2010

(65) Prior Publication Data

US 2011/0065678 A1    Mar. 17, 2011

(30) Foreign Application Priority Data

Sep. 11, 2009   (EP) .................................. 09011665

(51) Int. Cl.
| | | |
|---|---|---|
| *A61K 31/58* | (2006.01) | |
| *C07J 71/00* | (2006.01) | |
| *C07J 75/00* | (2006.01) | |
| *A61P 29/00* | (2006.01) | |
| *A61P 37/06* | (2006.01) | |
| *A61P 37/08* | (2006.01) | |
| *A61P 11/06* | (2006.01) | |

(52) U.S. Cl.
USPC .............................. 540/56; 514/171; 514/176

(58) Field of Classification Search
None
See application file for complete search history.

(56) References Cited

U.S. PATENT DOCUMENTS

| | | | |
|---|---|---|---|
| 3,048,581 A |  | 8/1962 | Fried |
| 3,631,033 A |  | 12/1971 | Nathansohn |
| 3,928,326 A | * | 12/1975 | Brattsand et al. ............... 540/63 |
| 4,432,976 A |  | 2/1984 | Annen et al. |
| 5,200,518 A |  | 4/1993 | Kim et al. |

FOREIGN PATENT DOCUMENTS

| | | |
|---|---|---|
| DE | 11 31 213 | 6/1962 |
| DE | 20 21 718 | 11/1970 |
| EP | 0 072 989 | 3/1983 |
| GB | 1 120 337 | 7/1968 |
| GB | 1 122 863 | 8/1968 |
| GB | 1 302 572 | 1/1973 |
| GB | 1 578 446 | 11/1980 |
| WO | 2005/028495 | 3/2005 |
| WO | 2006/005611 | 1/2006 |
| WO | WO 2006/005611 * | 1/2006 |
| WO | 2006/138212 | 12/2006 |
| WO | 2009/108118 | 9/2009 |

OTHER PUBLICATIONS

Green et al. In Journal of Medicinal Chemistry 25, 1492-1495 (1982).*
Hancox et al. In Thorax 1999; 54(6), 482-487.*
U.S. Appl. No. 13/020,988, filed Feb. 4, 2011, Ghidini, et al.
Green M. J. et al., "Journal of Medicinal Chemistry, American Chemical Society", vol. 25, No. 12, (1982), pp. 1492-1495.
A. I. Terekhina et al., "Pharmaceutical Chemistry Journal", vol. 27, No. 3 (1993), pp. 188-192.
Database CA [Online] Chemical Abstracts Service, Columbus, Ohio, US; 1992, Sin, K. S. et al., "Synthesis and pharmacological evaluation of new topical anti-inflammatory steroids", XP002576963 retrieved from STN Database accession No. 1992:401156 & Sin, K. S. et al, "Synthesis and pharmacological evaluation of new topical anti-inflammatory steroids", Drugs Under Experimental and Clinical Research, 17(8), 375-80 Coden: Decrdtp; ISSN: 0378-0501, (1991).
Database CA [Online] Chemical Abstracts Service, Columbus, Ohio, US; 1996, Miki, Takuchi et al., XP002576964 retrieved from STN Database accession No. 1996:356668; JP 1996-0319.
European Search Report in European Patent Application 09011665. 8, issued Apr. 21, 2010.
U.S. Appl. No. 13/421,128, filed Mar. 15, 2012, Ghidini, et al.
U.S. Appl. No. 13/421,150, filed Mar. 15, 2012, Ghidini, et al.
U.S. Appl. No. 13/561,134, filed Jul. 30, 2012, Ghidini, et al.

* cited by examiner

*Primary Examiner* — Dennis Heyer
(74) *Attorney, Agent, or Firm* — Oblon, Spivak, McClelland, Maier & Neustadt, L.L.P.

(57) ABSTRACT

Novel glucocorticosteroids that are derivatives of isoxazolidine are useful as anti-inflammatory and antiallergic compounds.

20 Claims, No Drawings

ISOXAZOLIDINE DERIVATIVES

CROSS REFERENCES TO RELATED APPLICATIONS

This application claims priority to European Patent Application No. 09011665.8 filed on Sep. 11, 2009, which is incorporated herein by reference in its entirety.

BACKGROUND OF THE INVENTION

1. Field of the Invention

The present invention relates to novel anti-inflammatory and antiallergic compounds of the glucocorticosteroid series. The present invention also relates to methods of preparing such a compound, pharmaceutical compositions which contain such a compound, combinations which contain such a compound and therapeutic uses of such a compound.

2. Discussion of the Background

Corticosteroids are potent anti-inflammatory agents, able to decrease the number, activity, and movement of inflammatory cells. They are commonly used to treat a wide range of chronic and acute inflammatory conditions including asthma, chronic obstructive pulmonary disease (COPD), allergic rhinitis, rheumatoid arthritis, inflammatory bowel disease and autoimmune diseases.

Corticosteroids mediate their effects through the glucocorticoid receptor (GR). The binding of corticosteroids to GR induces its nuclear translocation which, in turn, affects a number of downstream pathways via DNA-binding-dependent (e.g. transactivation) and -independent (e.g. transespression) mechanisms.

Corticosteroids for treating chronic inflammatory conditions in the lung such as asthma and COPD are currently administered through inhalation. One of the advantages of employing inhaled corticosteroids (ICS) is the possibility of delivering the drug directly at the site of action, limiting systemic side-effects, thus resulting in a more rapid clinical response and a higher therapeutic ratio.

Although ICS treatment can afford important benefits, especially in asthma it is important to minimise ICS systemic exposure which leads to the occurrence and severity of unwanted side effects that may be associated with chronic administration. Moreover, the limited duration of action of ICS currently available in the clinical practice contributes to suboptimal management of the disease. While the inhaler technology is the key point to target the lung, the modulation of the substituents on the corticosteroids molecular scaffold is important for the optimization of pharmacokinetic and pharmacodynamic properties in order to decrease oral bioavailability, confine pharmacological activity only in the lung (prodrugs and soft drugs) and increase systemic clearance. Moreover, long lasting ICS activity in the lung is highly desirable as once daily administration of ICS would allow the reduction of the frequency of administration and, thus, substantially improve patient compliance and, as a result, disease management and control. In sum, there is a pressing medical need for developing ICS with improved pharmacokinetic and pharmacodynamic characteristics.

Glucocorticoid isoxazolidine derivatives are described in WO2006/005611, GB1578446, and in "Synthesis and topical anti-inflammatory activity of some steroidal [16α,17α-d] isoxazolidines" (J. Med. Chem., vol. 25, pp. 1492-1495, 1982).

SUMMARY OF THE INVENTION

Accordingly, it is one object of the present invention to provide novel glucocorticosteroids.

It is another object of the present invention to provide novel anti-inflammatory and antiallergic compounds of the glucocorticosteroid series.

It is another object of the present invention to provide novel methods of preparing such a compound.

It is another object of the present invention to provide novel pharmaceutical compositions which contain such a compound.

It is another object of the present invention to provide novel combinations which contain such a compound.

It is another object of the present invention to provide novel methods of treating and/or preventing certain conditions by administering such a compound.

These and other objects, which will become apparent during the following detailed description, have been achieved by the inventors' discovery of new glucocorticosteroids which are isoxazolidine derivatives.

Thus, the invention provides compounds of general formula (I), methods of preparing said compounds, compositions comprising them and therapeutic uses thereof:

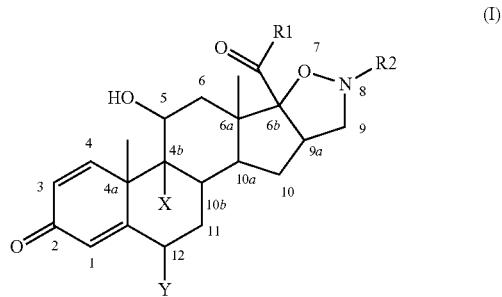

wherein
R1 is $(CH_2)_n$—Z—$(CH_2)_{n'}$—R4 wherein n and n' are each independently 0, 1 or 2;
Z is a single bond or is selected from the group consisting of S, O, CO and NR3, wherein
R3 is selected from the group consisting of H, straight or branched $(C_1-C_6)$alkyl, $(C_1-C_6)$haloalkyl, $(C_3-C_8)$cycloalkyl, aryl, aryl$(C_1-C_6)$alkyl and heteroaryl, which are optionally substituted by CN;
R4 is selected from the group consisting of:
  H, halogen, OH, SH, CN, $NH_2$;
  aryl$(C_1-C_6)$alkyl, $(C_1-C_6)$alkylsulfonyl, $(C_1-C_6)$alkylcarbonyl, $(C_1-C_6)$alkylcarboxyl, O$(C_1-C_6)$alkylcarboxyl, $(C_1-C_6)$alkylamide and $(C_1-C_6)$alkoxy, which are optionally substituted by oxo groups;
  $(C_1-C_6)$alkyl which may be optionally substituted by one or more substituents selected from the group consisting of halogen atoms, CN, OH, $NH_2$, $NO_2$, $CF_3$ and SH;
  $(C_2-C_6)$alkynyl;
  a mono-, bi- or tricyclic saturated or partially saturated or unsaturated ring, such as $(C_3-C_8)$cycloalkyl, aryl, $(C_5-C_{10})$heterocycloalkyl or heteroaryl, optionally substituted by one or more halogen atoms or oxo groups;
R2 is selected from the group consisting of
  H;
  straight or branched $(C_1-C_6)$alkyl;
  —$(CH_2)_m$R5, wherein R5 is heteroaryl optionally substituted with a substituent selected from the group consisting of oxo, OH, halogen, CN, $NH_2$, $NO_2$, aryl, $(C_1-C_6)$alkylsulfonyl, $(C_1-C_6)$alkoxy, $(C_1-C_6)$alkylthio, $(C_1-C_6)$alkylcarboxyl, $(C_1-C_6)$alkylamide, aryl$(C_1-C_6)$alkoxy and ($C_1$-$C_6$)alkyl, each of which is optionally substituted by one or more halogen atoms or COOH;

($CH_2$)$_p$NR6R7;
($CH_2$)$_p$NR6COR7;
($CH_2$)$_p$NR6$SO_2$R7;
($CH_2$)$_m$CONR6R7;
($CH_2$)$_m$$SO_2$NR6R7;
($CH_2$)$_m$COR7;
($CH_2$)$_p$OR7;
($CH_2$)$_m$$SO_q$R7;

wherein R6 and R7 are independently H or are selected from the group consisting of straight or branched ($C_1$-$C_6$)alkyl, ($C_3$-$C_8$)cycloalkyl, aryl($C_1$-$C_6$)alkyl and a saturated, partially saturated or unsaturated, optionally fused ring such as aryl, ($C_5$-$C_{10}$)heterocycloalkyl or heteroaryl, which groups may be optionally substituted with one or more substituents selected from the group consisting of halogen, CN, oxo, $NH_2$, $NO_2$ and ($C_1$-$C_6$)alkyl;

($CH_2$)$_p$R8 wherein R8 is selected from the group consisting of halogen, oxo, CN, OH, $NH_2$, $NO_2$; ($C_3$-$C_8$)cycloalkyl, aryl and a saturated, partially saturated or unsaturated optionally fused ring such as ($C_5$-$C_{10}$)heterocycloalkyl, which are optionally substituted by one or more substituents selected from the group consisting of halogen, CO, CN, ($C_1$-$C_6$)alkyl, ($C_1$-$C_6$)haloalkyl, ($C_1$-$C_6$)carboxyalkyl, ($C_1$-$C_6$)alkoxy, ($C_1$-$C_6$)haloalkoxy and ($C_1$-$C_6$)alkylsulfonyl;

wherein m and p are, each independently, 0 or an integer from 1 to 6 and q is 0, 1 or 2 and X and Y are independently selected from the group consisting of H and halogen atoms and pharmaceutically acceptable salts thereof, with the proviso that when R2 is ($C_1$-$C_6$)alkyl, X and Y are not simultaneously H.

It will be apparent to those skilled in the art that compounds of general formula (I) contain asymmetric centers at least at the positions 4a, 4b, 5, 6a, 6b, 9a, 10a, 10b, 12 and therefore may exist as many optical stereoisomers and mixtures thereof. Therefore the invention is also directed to all of these forms.

Preferred compounds are those of general formula (I) wherein the configuration of the chiral carbon atoms is fixed and specifically wherein 4a is (R), 4b is (R), 5 is (S), 6a is (S), 6b is (R), 9a is (S), 10a is (S), 10b is (S) and 12 is (S), which are represented by the formula (I') below

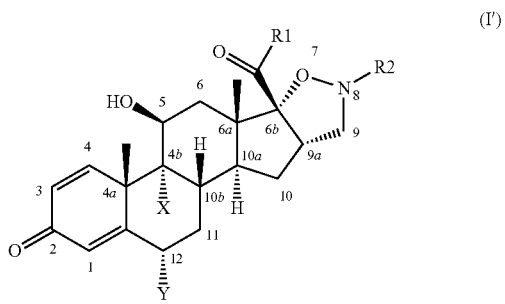

(I')

wherein the values of R1, R2, X and Y are as defined above.

Compounds of general formula (I) are capable of forming acid addition salts, particularly pharmaceutically acceptable acid addition salts.

Pharmaceutically acceptable acid addition salts of the compounds of formula (I), thus encompassing also those of formula (I'), include those of inorganic acids, for example hydrohalic acids such as hydrofluoric acid, hydrochloric acid, hydrobromic acid or hydroiodic acid; nitric acid, sulfuric acid, phosphoric acid; and organic acids, for example aliphatic monocarboxylic acids such as formic acid, acetic acid, trifluoroacetic acid, and propionic acid; aliphatic hydroxyl acids such as lactic acid, citric acid, tartaric acid or malic acid; dicarboxylic acids such as maleic acid, fumaric acid, oxalic acid or succinic acid; aromatic carboxylic acids such as benzoic acid; aromatic hydroxyl acids and sulfonic acids.

These salts may be prepared from compounds of formula (I) by known salt-forming procedures.

The compounds of formula (I) of the present invention may be prepared according to a variety of synthetic steps which are carried out according to conventional methods and techniques.

The present invention is also directed to processes for the preparation of compounds of general formula (I') wherein R1=($CH_2$)$_n$—Z—($CH_2$)$_{n'}$—R4 wherein n=1 and R4 is as defined above, which comprise:

reacting a compound of formula (VI):

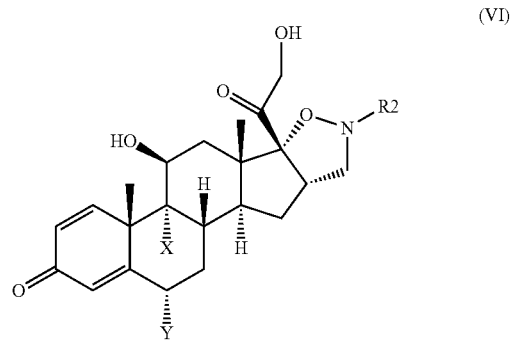

(VI)

with methanesulfonyl chloride or p-toluenesulfonyl chloride to obtain a compound of general formula (XI):

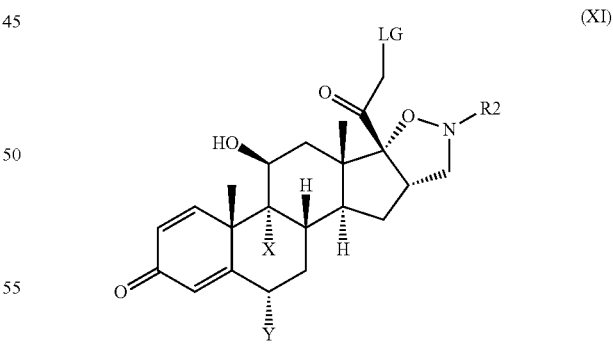

(XI)

wherein the leaving group (LG) may be displaced by nucleophiles.

The present invention is also directed to processes for the preparation of compounds of general formula (I') wherein R1=($CH_2$)$_n$—Z—($CH_2$)$_{n'}$—R4 wherein n=0, Z and R4 are as defined above, which comprise:

reacting a compound of formula (VI) under oxidizing conditions to obtain an intermediate of general formula (XII):

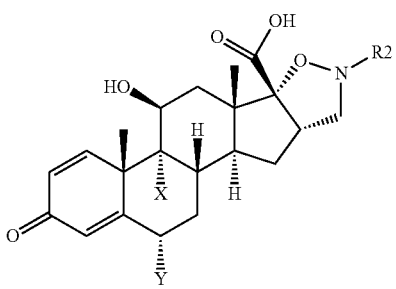
(XII)

treating the compound of formula (XII) with one or more equivalents of an acid activating agent and then with a nucleophile.

The present invention is also directed to processes for the preparation of compounds of general formula (I') wherein R1=(CH$_2$)$_n$—Z—(CH$_2$)$_n$—R4 wherein n=0, Z=S and R4 is as defined above, which comprise:

reacting a compound of formula (VI) under oxidizing conditions to obtain an intermediate of general formula (XII)

converting the intermediate of formula (XII) into a compound of general formula (XIII):

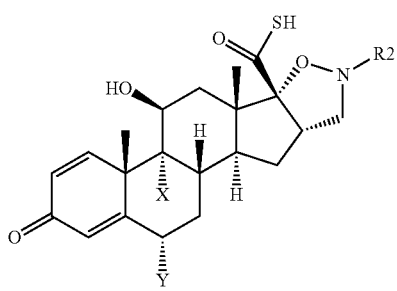
(XIII)

alkylating the compound of formula (XIII).

The present invention is also directed to processes for the preparation of a compound of general formula (VI) which comprises:

reacting a compound of general formula (IV):

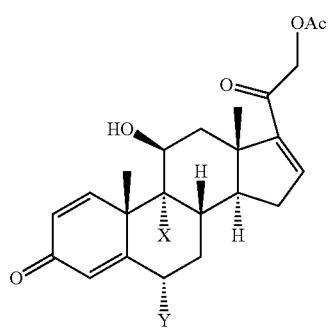
(IV)

with N-tetrahydropyranyl hydroxylamine (HO—NH-THP), to prepare a compound of formula (V):

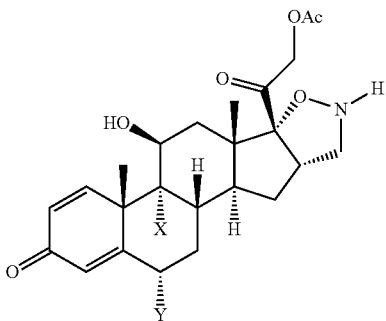
(V)

optionally further functionalizing the compound of formula (V) and deprotecting.

The present invention is also directed to processes for the preparation of a compound of general formula (VI), which comprise:

reacting a compound of formula (VII)

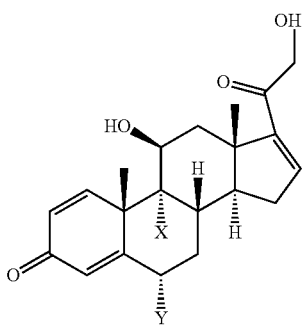
(VII)

with a compound of formula (X)

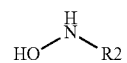
(X)

The present invention is also directed to processes for the preparation of a compound of general formula (VI), which comprise:

reaction of a compound of formula (VII) with N-tetrahydropyranyl hydroxylamine (HO—NH-THP) to obtain a compound of formula (VIII)

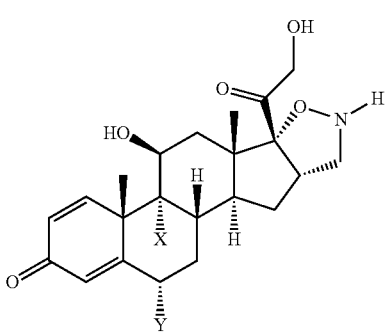
(VIII)

protecting the compound of formula (VIII) to obtain a compound of formula (IX)

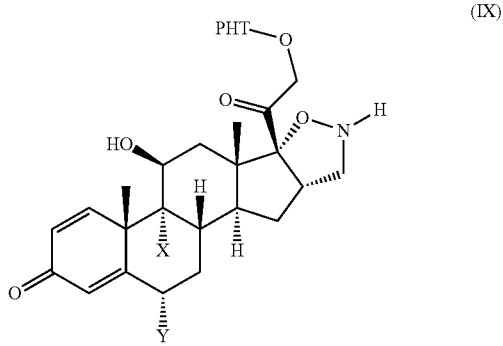

(IX)

optionally further functionalizing the compound of formula (IX) and
deprotecting.

The present invention is also directed to processes for the preparation of compounds of general formula (I') wherein R1=(CH$_2$)$_n$—Z—(CH$_2$)$_{n'}$—R4 wherein n=1, Z=O and R4=Ac, which comprise the reaction of the intermediates of general formula (IV) with hydroxylamines of formula (X).

The present invention is also directed to processes for the preparation of compounds of general formula (I') wherein R1=(CH$_2$)$_n$—Z—(CH$_2$)$_{n'}$—R4 wherein n=1, Z=O, R4=H and X=Cl, which comprise:

reacting a compound of formula (I') wherein n=1, Z=O, R4=Ac and X=H with methanesulfonyl chloride to obtain a compound of formula (XIV)

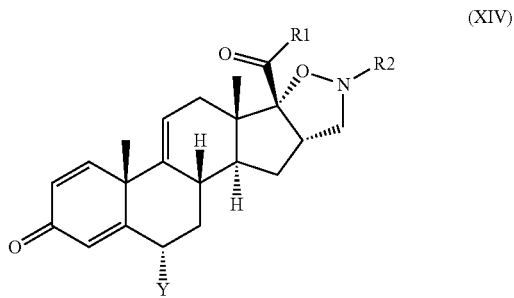

(XIV)

reacting the compound (XIV) with a chlorinating agent and hydrolyzing.

From all of the above, it is clear to the person skilled in the art that by selecting the starting material with a proper stereochemical configuration, any of the possible stereoisomers of formula (I) could be thus obtained.

The present invention also provides pharmaceutical compositions comprising a compound of general formula (I) or (I') and one or more pharmaceutically acceptable carriers and/or excipients.

The compounds of the invention may be administered as the sole active agent or in combination with other pharmaceutical active ingredients including those currently used in the treatment of respiratory disorders, e.g. beta2-agonists, antimuscarinic agents, corticosteroids, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs), and mucus regulators.

The present invention also provides combinations of a compound of general formula (I) or (I') with a β2-agonist selected from the group consisting of carmoterol, GSK-642444, indacaterol, milveterol, arformoterol, formoterol, salbutamol, levalbuterol, terbutaline, AZD-3199, BI-1744-CL, LAS-100977, bambuterol, isoproterenol, procaterol, clenbuterol, reproterol, fenoterol and ASF-1020 and salts thereof.

The present invention also provides combinations of a compound of general formula (I) or (I') with an antimuscarinic agent selected from the group consisting of aclidinium, tiotropium, ipratropium, trospium, glycopirronium and oxitropium salts.

The present invention also provides combinations of a compound of general formula (I) or (I') with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TP1-PD3, ELB-353, CC-11050, GSK-256066, oglemilast, OX-914, tetomilast, MEM-1414 and RPL-554.

The present invention also provides combinations of a compound of general formula (I) or (I') with a P38 MAP kinase inhibitor selected from the group consisting of semapimod, talmapimod, pirfenidone, PH-797804, GSK-725, minokine and losrnapimod and salts thereof.

In a preferred embodiment, the present invention provides combinations of a compound of general formula (I) or (I') with an IKK2 inhibitor.

The invention also provides combinations of a compound of formula (I) with a HNE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C and prolastin inhaled.

The invention also provides combinations of a compound of formula (I) with a leukotriene modulator selected from the group consisting of montelukast, zafirlukast and pranlukast.

The invention also provides combinations of a compound of formula (I) with a NSAID selected from the group consisting of ibuprofen and ketoprofen.

The invention also provides combinations of a compound of formula (I) with a mucus regulator selected from the group consisting of INS-37217, diquafosol, sibenadet, CS-003, talnetant, DNK-333, MSI-1956 and gefitinib.

The present invention also provides a compound of general formula (I) or (I') for use as a medicament.

The invention also relates to the use of compounds of general formula (I) or (I') to decrease the number, activity and movement of the inflammatory cells in vitro and/or in vivo.

The present invention is also directed to compounds of general formula (I) or (I') for use in the prevention or treatment of any disease wherein the decrease in the number, activity and movement of inflammatory cells is involved.

In a further aspect the present invention provides the use of compounds of general formula (I) or (I') for the prevention and/or treatment of any disease wherein the decrease in the number, activity and movement of inflammatory cells is involved.

In particular, compounds of general formula (I) or (I') alone or combined with one or more active ingredients may be administered for the prevention and/or treatment of a disease the respiratory tract characterized by airway obstruction such as asthma and COPD.

In a further aspect the present invention provides the use of compounds of general formula (I) or (I') for the preparation of a medicament for the prevention and/or treatment of any disease wherein the decrease in the number, activity and movement of inflammatory cells is involved.

Moreover the present invention provides a method for prevention and/or treatment of any disease wherein the decrease in the number, activity and movement of inflammatory cells is involved, said method comprising administering to a patient in need of such treatment a therapeutically effective amount of a compound of general formula (I) or (I').

The present invention also provides pharmaceutical preparations of compounds of general formula (I) or (I') suitable for administration by inhalation, by injection, orally or intranasally.

Inhalable preparations include inhalable powders, propellant-containing metering aerosols or propellant-free inhalable formulations.

The invention is also directed to a device which may be a single- or multi-dose dry powder inhaler, a metered dose inhaler or a nebulizer, in particular a soft mist nebulizer comprising a compound of general formula (I) or (I').

The invention is also directed to a kit comprising the pharmaceutical compositions of compounds of general formula (I) or (I') alone or in combination with or in admixture with one or more pharmaceutically acceptable carriers and/or excipients and a device which may be a single- or multi-dose dry powder inhaler, a metered dose inhaler or a nebulizer.

The isoxazolidine glucocorticoids of the present invention are profiled in vitro by potency and efficacy in: a) binding to the GR, b) inducing nuclear translocation of GR, and c) inhibition of inflammatory responses in macrophages. In addition, the optimization of pharmacokinetics/pharmacodynamic properties is pursued with the aim of improving the anti-inflammatory potency, efficacy and duration of action in the lung and to reduce systemic side effects. When administered topically in the lung in experimental animal models the isoxazolidine glucocorticoids of the present invention are characterized by a good anti-inflammatory potency and efficacy which is associated with a long duration of action and a limited systemic exposure.

DETAILED DESCRIPTION OF THE PREFERRED EMBODIMENTS

The term "halogen" or "halogen atoms" as used herein includes fluorine, chlorine, bromine and iodine.

As used herein, the expression "$(C_1-C_6)$alkyl" refers to straight- and branched-chained alkyl groups wherein the number of constituent carbon atoms is in the range 1 to 6. Examples of alkyl groups are methyl, ethyl, n-propyl, isopropyl, t-butyl, pentyl and hexyl.

The derived expression "$(C_2-C_6)$alkynyl" is to be construed in an analogous manner. Examples of alkynyl groups include ethynyl, propynyl, butynyl, pentynyl and hexynyl.

The term "$(C_1-C_6)$alkoxy" refers to alkyl-oxy (e.g. alkoxy) groups. Examples of said groups may thus comprise methoxy, ethoxy, n-propoxy, isopropoxy, n-butoxy, isobutoxy, sec-butoxy, tert-butoxy, pentoxy, hexoxy and the like.

The expressions "$(C_1-C_6)$haloalkyl" and "$(C_1-C_6)$haloalkoxy", refer to the above "$(C_1-C_6)$alkyl" and "$(C_1-C_6)$alkoxy" groups wherein one or more hydrogen atoms are replaced by one or more halogen atoms, which can be the same or different from each other.

Likewise, the derived expressions "$(C_1-C_6)$alkylcarbonyl", "$O(C_1-C_6)$-alkylcarbonyl", "$(C_1-C_6)$alkylcarboxyl" and "$(C_1-C_6)$alkylamide" refer respectively to alkyl-CO, O-alkyl-CO, alkyl-$CO_2$— and alkyl-$NH_2$, alkyl-NH-alkyl or alkyl-N-(alkyl)$_2$ groups.

Likewise, the expression "$(C_1-C_6)$alkylsulfonyl" refers to alkyl-$SO_2$— group.

As used herein, the expression "$(C_3-C_8)$cycloalkyl" refers to cyclic non-aromatic hydrocarbon groups with from 3 to 8 carbon atoms. Examples include cyclopropyl, cyclobutyl, cyclopentyl, cyclohexyl, cycloheptyl and the like.

As used herein, the expression "$(C_5-C_{10})$heterocycloalkyl" refers to cyclic non-aromatic hydrocarbon groups, wherein at least one ring atom is a heteroatom (e.g. N, S, or O). Examples include dihydropyridine and dihydrobenzodioxin radicals.

As used herein, the expression "aryl" refers to mono, bi- or tricyclic ring systems which have 5 to 20 ring atoms, preferably from 5 to 15 and wherein at least one ring is aromatic.

The expressions "aryl$(C_1-C_6)$alkyl" and "aryl$(C_1-C_6)$alkoxy" refer to $(C_1-C_6)$alkyl groups further substituted by aryl, alkoxy, heteroaryl or cycloalkyl rings, respectively. Examples of suitable aryl$(C_1-C_6)$alkyl groups include benzyl, biphenylmethyl and thiophenylmethyl.

As used herein, the expression "heteroaryl" refers to mono, bi- or tricyclic ring system which have 5 to 20 ring atoms, preferably from 5 to 15, in which at least one ring is aromatic and in which at least one ring atom is a heteroatom (e.g. N, S or O). Examples of suitable monocyclic systems include thiophene, cyclopentadiene, benzene, pyrrole, pyrazole, imidazole, isoxazole, oxazole, isothiazole, thiazole, pyridine, imidazolidine, piperidine and furan radicals such as tetrahydrofuran. Examples of suitable bicyclic systems include naphthalene, biphenyl, purine, pteridine, benzotriazole, quinoline, isoquinoline, indole, isoindole, benzofuran, benzodioxane and benzothiophene radicals. Examples of suitable tricyclic systems include fluorene radicals.

The invention is directed to compounds acting as glucocorticosteroids, which are potent anti-inflammatory agents.

Said compounds decrease the number, activity and movement of inflammatory cells into the bronchial submucosa, leading to decreased airway responsiveness.

In particular the present invention relates to compounds of general formula (I) as defined above

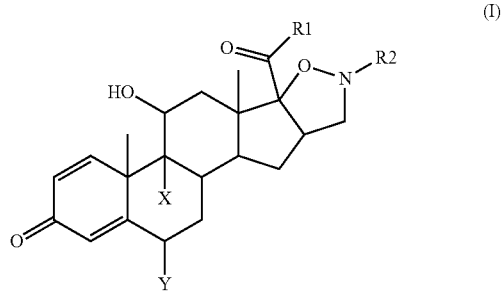

(I)

Preferred compounds are those of general formula (I) wherein the configuration of the chiral carbon atoms is fixed and specifically wherein 4a is (R), 4b is (R), 5 is (S), 6a is (S), 6b is (R), 9a is (S), 10a is (S), 10b is (S) and 12 is (S), which are represented by the formula (I') below

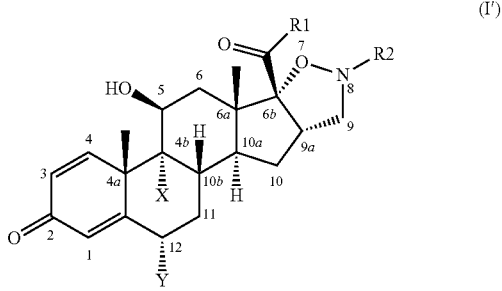

(I')

wherein the values of R1, R2, X and Y are as defined above, in free or salt form.

A first preferred group of compounds of general formula (I') is that wherein R1 is $(CH_2)_n$—Z—$(CH_2)_{n'}$—R4, wherein n is 0 or 1; Z is a single bond or is selected from the group consisting of S, O and NR3, wherein R3 is H or $(C_1-C_6)$alkyl; n' is 0, 1 or 2; R4 is selected from the group consisting of H, halogen, CN, OH; $(C_1-C_6)$alkyl, optionally substituted by one or more substituents selected from the group consisting of halogen atoms, CN, OH, $NH_2$, $NO_2$, $CF_3$ and SH; aryl$(C_1$-$C_6)$alkyl, $(C_1-C_6)$alkynyl, $(C_1-C_6)$alkylsulfonyl, $(C_1-C_6)$alkylcarbonyl, $O(C_1-C_6)$alkylcarbonyl, $(C_1-C_6)$alkylamide, $(C_1-C_6)$alkylcarboxyl, $(C_5-C_{10})$heterocycloalkyl and heteroaryl, which are optionally substituted by oxo groups; R2, X and Y have the above reported meanings.

Still more preferred within this class, are the compounds of general formula (I'), wherein R4 is selected from the group consisting of methyl, ethyl, benzothiazole, benzooxazole, tetrahydrofuran, tetrahydropiran, methylsulfonyl, methylcarbonyl, chlorine, fluorine, trifluoromethyl, methylcarboxyl, ethylcarboxyl, methoxy, ethoxy, trifluoromethyl and butynyl.

Even more preferred within this class, are the compounds of general formula (I'), wherein R3 is H or methyl.

Even more preferred within this class, are the compounds of general formula (I'), wherein R2 is a straight or branched $(C_1-C_6)$alkyl.

A second preferred group of compounds of general formula (I') is that wherein R1, X and Y are as defined above; R2 is H or is selected from the group consisting of $(CH_2)_mR5$ wherein m is 1 or 2, R5 is heteroaryl optionally substituted by a group selected from halogen, CN, OH, CF3, $(C_1-C_6)$alkyl, $(C_1-C_6)$haloalkyl, $(C_1-C_6)$alkoxy, $(C_1-C_6)$alkylsulfonyl and aryl; $(CH_2)_m$CONR6R7 wherein m is 0, R6 is $(C_1-C_6)$alkyl and R7 is aryl; $(CH_2)_m$COR7, wherein m is 1, R7 is aryl, heteroaryl or $(C_5-C_{10})$heterocycloalkyl; $(CH_2)_p$OR7, wherein p is 2 and R7 is aryl or aryl$(C_1-C_6)$alkyl; $(CH_2)_mSO_qR7$ wherein m is 0 or 2, q is 0 or 2 and R7 is $(C_1-C_6)$alkyl or aryl; and $(CH_2)_pR8$ wherein p is 1, 2 or 3 and R8 is selected from the group consisting of aryl and $(C_5-C_{10})$heterocycloalkyl, optionally substituted by one or more substituents selected from the group consisting of halogen, oxo, CN, OH, $CF_3$, $(C_1-C_6)$alkyl, $(C_1-C_6)$haloalkyl, $(C_1-C_6)$alkoxy, $(C_1-C_6)$haloalkoxy, $(C_1-C_6)$alkylcarboxyl and $(C_1-C_6)$alkylsulfonyl.

Still more preferred within this class, are the compounds of general formula (I'), wherein R2 is selected from the group consisting of phenyl, thiophenyl, pyridyl, imidazolyl, thiazolyl, benziloxyethyl, phenylsulfanyl, phenylpropyl, phenoxyethyl, isoxazolyl, benzoyl, furancarbonyl, methanesulfonyl, dihydropyridinmethyl and methylphenylamide, cyclopentenone, benzofuran, furan, dihydrobenzodioxin radicals.

A third preferred group of compounds of general formula (I') is that wherein R1 and R2 are as defined above and X and Y are both H or fluorine atoms or X is chlorine and Y is H.

Most of the compounds of general formula (I) and (I') were found to show an in vitro activity ranging from $10^{-8}$ to $10^{-10}$ M in all the cell free and cell based assays employed and some of them turned out to be endowed with a long duration of anti-inflammatory action in the lung in rodent experimental models in vivo.

For examples purposes, and according to preferred embodiments, the present invention provides the compounds reported below:

| Cpd. | Chemical Name |
|---|---|
| 9 | (4aR,4bS,5S,6aS,6bR,9aS,10aS,10bS)-8-Furan-3-ylmethyl-5-hydroxy-6b-(2-hydroxy-acetyl)-4a,6a-dimethyl 4a,4b,5,6,6a,6b,8,9,9a,10,10a,10b,11,12-tetradecahydro-7-oxa-8-aza pentaleno[2,1-a]phenanthren-2-one |
| 10 | (4aR,4bS,5S,6aS,6bR,9aS,10aS,10bS)-8-Benzyl-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 11 | (4aR,4bS,5S,6aS,6bR,9aS,10aS,10bS)-5-Hydroxy-6b-(2-hydroxy-acetyl)-4a,6a-dimethyl-8-thiophen-3-ylmethyl-4a,4b,5,6,6a,6b,8,9,9a,10,10a,10b,11,12-tetradecahydro-7-oxa-8-aza-pentaleno[2,1-a]phenanthren-2-one |
| 12 | (4aR,4bS,5S,6aS,6bR,9aS,10aS,10bS)-5-Hydroxy-6b-(2-hydroxy-acetyl)-4a,6a-dimethyl-8-thiophen-3-ylmethyl-4a,4b,5,6,6a,6b,8,9,9a,10,10a,10b,11,12-tetradecahydro-7-oxa-8-aza-pentaleno[2,1-a]phenanthren-2-one |
| 13 | (4aR,4bS,5S,6aS,6bR,9aS,10aS,10bS)-5-Hydroxy-6b-(2-hydroxy-acetyl)-4a,6a-dimethyl-8-pyridin-3-ylmethyl-4a,4b,5,6,6a,6b,8,9,9a,10,10a,10b,11,12-tetradecahydro-7-oxa-8-aza-pentaleno[2,1-a]phenanthren-2-one |
| 14 | (4aR,4bS,5S,6aS,6bR,9aS,10aS,10bS)-5-Hydroxy-6b-(2-hydroxy-acetyl)-8-(1H-imidazol-4-ylmethyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 15 | (4aR,4bS,5S,6aS,6bR,9aS,10aS,10bS)-5-Hydroxy-6b-(2-hydroxy-acetyl)-4a,6a-dimethyl-8-(4-methyl-thiazol-2-ylmethyl)-4a,4b,5,6,6a,6b,8,9,9a,10,10a,10b,11,12-tetradecahydro-7-oxa-8-aza-pentaleno[2,1-a]phenanthren-2-one |
| 16 | (4aR,4bS,5S,6aS,6bR,9aS,10aS,10bS)-8-(5-Bromo-furan-2-ylmethyl)-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 17 | (4aR,4bS,5S,6aS,6bR,9aS,10aS,10bS)-8-Benzofuran-2-ylmethyl-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 18 | (4aR,4bS,5S,6aS,6bR,9aS,10aS,10bS)-8-Furan-2-ylmethyl-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 19 | (4aR,4bS,5S,6aS,6bR,9aS,10aS,10bS)-8-(2-Benzyloxy-ethyl)-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 20 | (4aR,4bS,5S,6aS,6bR,9aS,10aS,10bS)-5-Hydroxy-6b-(2-hydroxy-acetyl)-8-(4-methoxy-benzyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |

| Cpd. | Chemical Name |
|---|---|
| 21 | (4aR,4bS,5S,6aS,6bR,9aS,10aS,10bS)-5-Hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 22 | (4aR,4bS,5S,6aS,6bR,9aS,10aS,10bS)-5-Hydroxy-6b-(2-hydroxy-acetyl)-4a,6a-dimethyl-8-(2-phenylsulfanyl-ethyl)-4a,4b,5,6,6a,6b,8,9,9a,10,10a,10b,11,12-tetradecahydro-7-oxa-8-aza-pentaleno[2,1-a]phenanthren-2-one |
| 23 | (4aS,4bR,5S,6aS,6bR,9aS,10aS,10bS,12S)-4b,12-Difluoro-8-furan-3-ylmethyl-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 24 | (4aR,4bS,5S,6aS,6bR,9aS,10aS,10bS)-5-Hydroxy-6b-(2-hydroxy-acetyl)-4a,6a-dimethyl-8-(2-phenoxy-ethyl)-4a,4b,5,6,6a,6b,8,9,9a,10,10a,10b,11,12-tetradecahydro-7-oxa-8-aza-pentaleno[2,1-a]phenanthren-2-one |
| 25 | (4aR,4bS,5S,6aS,6bR,9aS,10aS,10bS)-5-Hydroxy-6b-(2-hydroxy-acetyl)-4a,6a-dimethyl-8-(3-phenyl-propyl)-4a,4b,5,6,6a,6b,8,9,9a,10,10a,10b,11,12-tetradecahydro-7-oxa-8-aza-pentaleno[2,1-a]phenanthren-2-one |
| 26 | (4aR,4bS,5S,6aS,6bR,9aS,10aS,10bS)-8-(3,4-Dimethoxy-benzyl)-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 27 | (4aR,4bS,5S,6aS,6bR,9aS,10aS,10bS)-8-(2,3-Dihydro-benzo[1,4]dioxin-6-ylmethyl)-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 28 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(2-phenylsulfanyl-ethyl)-4a,4b,5,6,6a,6b,8,9,9a,10,10a,10b,11,12-tetradecahydro-7-oxa-8-aza-pentaleno[2,1-a]phenanthren-2-one |
| 29 | (4aR,4bS,5S,6aS,6bR,9aS,10aS,10bS)-8-(4-Fluoro-benzyl)-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 30 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(3-phenyl-propyl)-4a,4b,5,6,6a,6b,8,9,9a,10,10a,10b,11,12-tetradecahydro-7-oxa-8-aza-pentaleno[2,1-a]phenanthren-2-one |
| 31 | (4aR,4bS,5S,6aS,6bR,9aS,10aS,10bS)-5-Hydroxy-6b-(2-hydroxy-acetyl)-4a,6a-dimethyl-8-thiophen-2-ylmethyl-4a,4b,5,6,6a,6b,8,9,9a,10,10a,10b,11,12-tetradecahydro-7-oxa-8-aza-pentaleno[2,1-a]phenanthren-2-one |
| 32 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(2-phenoxy-ethyl)-4a,4b,5,6,6a,6b,8,9,9a,10,10a,10b,11,12-tetradecahydro-7-oxa-8-aza-pentaleno[2,1-a]phenanthren-2-one |
| 33 | (4aS,4bR,5S,6aS,6bR,9aS,10aS,10bS,12S)-8-(3,4-Dimethoxy-benzyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 34 | (4aR,4bS,5S,6aS,6bR,9aS,10aS,10bS)-8-(4-Chloro-benzyl)-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 35 | (4aS,4bR,5S,6aS,6bR,9aS,10aS,10bS,12S)-4b,12-Difluoro-8-furan-2-ylmethyl-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 36 | (4aS,4bR,5S,6aS,6bR,9aS,10aS,10bS,12S)-8-(4-Chloro-benzyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 37 | (4aS,4bR,5S,6aS,6bR,9aS,10aS,10bS,12S)-4b,12-Difluoro-5-hydroxy-6b-(2-hydroxy-acetyl)-4a,6a-dimethyl-8-thiophen-2-ylmethyl-4a,4b,5,6,6a,6b,8,9,9a,10,10a,10b,11,12-tetradecahydro-7-oxa-8-aza-pentaleno[2,1-a]phenanthren-2-one |
| 38 | (4aS,4bR,5S,6aS,6bR,9aS,10aS,10bS,12S)-8-Benzyl-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 39 | (4aS,4bR,5S,6aS,6bR,9aS,10aS,10bS,12S)-8-(3,4-Dichloro-benzyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 40 | (4aS,4bR,5S,6aS,6bR,9aS,10aS,10bS,12S)-8-(3-Chloro-benzyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 41 | (4aS,4bR,5S,6aS,6bR,9aS,10aS,10bS,12S)-4b,12-Difluoro-5-hydroxy-6b-(2-hydroxy-acetyl)-8-(4-methoxy-benzyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 42 | (4aS,4bR,5S,6aS,6bR,9aS,10aS,10bS,12S)-8-(2-Chloro-benzyl)-4b,12-difluoro-5-hydroxy-6b-(2-hydroxy-acetyl)-4a,6a-dimethyl- |

| Cpd. | Chemical Name |
|---|---|
|  | 4a,4b,5,6,6a,6b,8,9,9a,10,10a,10b,11,12-tetradecahydro-7-oxa-8-aza-pentaleno[2,1-a]phenanthren-2-one |
| 43 | (4aS,4bR,5S,6aS,6bR,9aS,10aS,10bS,12S)-8-(2,6-Dichloro-benzyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 44 | (4aS,4bR,5S,6aS,6bR,9aS,10aS,10bS,12S)-4b,12-Difluoro-8-(4-fluoro-benzyl)-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 45 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(5-methyl-thiophen-2-ylmethyl)-4a,4b,5,6,6a,6b,8,9,9a,10,10a,10b,11,12-tetradecahydro-7-oxa-8-aza-pentaleno[2,1-a]phenanthren-2-one |
| 46 | (4aS,4bR,5S,6aS,6bR,9aS,10aS,10bS,12S)-8-(5-Chloro-furan-2-ylmethyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 47 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(4-methyl-benzyl)-4a,4b,5,6,6a,6b,8,9,9a,10,10a,10b,11,12-tetradecahydro-7-oxa-8-aza-pentaleno[2,1-a]phenanthren-2-one |
| 48 | (4aS,4bR,5S,6aS,6bR,9aS,10aS,10bS,12S)-8-(4,5-dimethyl-furan-2-ylmethyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 49 | (4aS,4bR,5S,6aS,6bR,9aS,10aS,10bS,12S)-4b,12-Difluoro-8-((S,R)-1-furan-2-yl-ethyl)-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 50 | 4-[(4aS,4bR,5S,6aS,6bR,9aS,10aS,10bS,12S)-4b,12-Difluoro-5-hydroxy-6b-(2-hydroxy-acetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-ylmethyl]-benzonitrile |
| 51 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(5-methyl-furan-2-ylmethyl)-4a,4b,5,6,6a,6b,8,9,9a,10,10a,10b,11,12-tetradecahydro-7-oxa-8-aza-pentaleno[2,1-a]phenanthren-2-one |
| 52 | (4aS,4bR,5S,6aS,6bR,9aS,10aS,10bS,12S)-4b,12-Difluoro-5-hydroxy-6b-(2-hydroxy-acetyl)-4a,6a-dimethyl-8-pyridin-3-ylmethyl-4a,4b,5,6,6a,6b,8,9,9a,10,10a,10b,11,12-tetradecahydro-7-oxa-8-aza-pentaleno[2,1-a]phenanthren-2-one |
| 53 | (4aS,4bR,5S,6aS,6bR,9aS,10aS,10bS,12S)-4b,12-Difluoro-5-hydroxy-6b-(2-hydroxy-acetyl)-4a,6a-dimethyl-8(2,3-dihydrobenzo[b][1,4]dioxine-6-ylmethyl)-4a,4b,5,6,6a,6b,8,9,9a,10,10a,10b,11,12-tetradecahydro-7-oxa-8-aza-pentaleno[2,1-a]phenanthren-2-one |
| 54 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(2-phenyl-thiazol-4-ylmethyl)-4a,4b,5,6,6a,6b,8,9,9a,10,10a,10b,11,12-tetradecahydro-7-oxa-8-aza-pentaleno[2,1-a]phenanthren-2-one |
| 55 | (4aS,4bR,5S,6aS,6bR,9aS,10aS,10bS,12S)-8-(2,3-Dichloro-benzyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 56 | (4aS,4bR,5S,6aS,6bR,9aS,10aS,10bS,12S)-8-(3,5-Dimethyl-isoxazol-4-ylmethyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 57 | (4aS,4bR,5S,6aS,6bR,9aS,10aS,10bS,12S)-4b,12-Difluoro-5-hydroxy-6b-(2-hydroxy-acetyl)-8-(4-methanesulfonyl-benzyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 58 | (4aS,4bR,5S,6aS,6bR,9aS,10aS,10bS,1S)-4b,12-Difluoro-5-hydroxy-6b-(2-hydroxy-acetyl)-4a,6a-dimethyl-8-(5-phenyl-furan-2-ylmethyl)-4a,4b,5,6,6a,6b,8,9,9a,10,10a,10b,11,12-tetradecahydro-7-oxa-8-aza-pentaleno[2,1-a]phenanthren-2-one |
| 59 | (4aS,4bR,5S,6aS,6bR,9aS,10aS,10bS,12S)-8-(5-Chloro-thiophen-2-ylmethyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 60 | (4aS,4bR,5S,6aS,6bR,9aS,10aS,10bS,12S)-8-Benzofuran-2-ylmethyl-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 61 | (4aS,4bR,5S,6aS,6bR,9aS,10aS,10bS,12S)-8-(4-Chloro-3-trifluoromethyl-benzyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |

| Cpd. | Chemical Name |
|---|---|
| 62 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(4-trifluoromethyl-benzyl)-4a,4b,5,6,6a,6b,8,9,9a,10,10a,10b,11,12-tetradecahydro-7-oxa-8-aza-pentaleno[2,1-a]phenanthren-2-one |
| 63 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(5-phenyl-isoxazol-3-ylmethyl)-4a,4b,5,6,6a,6b,8,9,9a,10,10a,10b,11,12-tetradecahydro-7-oxa-8-aza-pentaleno[2,1-a]phenanthren-2-one |
| 64 | (4aS,4bR,5S,6aS,6bR,9aS,10aS,10bS,12S)-4b,12-Difluoro-8-(4-fluoro-3-methoxy-benzyl)-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 65 | (4aS,4bR,5S,6aS,6bR,9aS,10aS,10bS,12S)-4b,12-Difluoro-5-hydroxy-6b-(2-hydroxy-acetyl)-4a,6a-dimethyl-8-pyridin-2-ylmethyl-4a,4b,5,6,6a,6b,8,9,9a,10,10a,10b,11,12-tetradecahydro-7-oxa-8-aza-pentaleno[2,1-a]phenanthren-2-one |
| 66 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(4-trifluoromethoxy-benzyl)-4a,4b,5,6,6a,6b,8,9,9a,10,10a,10b,11,12-tetradecahydro-7-oxa-8-aza-pentaleno[2,1-a]phenanthren-2-one |
| 67 | (4aS,4bR,5S,6aS,6bR,9aS,10aS,10bS,12S)-8-(4-Difluoromethoxy-benzyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 68 | (4aS,4bR,5S,6aS,6bR,9aS,10aS,10bS,12S)-4b,12-Difluoro-8-(3-fluoro-4-trifluoromethoxy-benzyl)-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 69 | (4aS,4bR,5S,6aS,6bR,9aS,10aS,10bS,12S)-4b,12-Difluoro-8-(4-fluoro-3-trifluoromethyl-benzyl)-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 70 | 5-[(4aS,4bR,5S,6aS,6bR,9aS,10aS,10bS,12S)-4b,12-Difluoro-5-hydroxy-6b-(2-hydroxy-acetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-ylmethyl]-2-fluoro-benzonitrile |
| 71 | (4aS,4bR,5S,6aS,6bR,9aS,10aS,10bS,12S)-4b,12-Difluoro-5-hydroxy-6b-(2-hydroxy-acetyl)-8-(4-hydroxy-benzyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 72 | 4-[(4aS,4bR,5S,6aS,6bR,9aS,10aS,10bS,12S)-4b,12-Difluoro-5-hydroxy-6b-(2-hydroxy-acetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthren-8-ylmethyl]-benzoic acid methyl ester |
| 73 | (4aS,4bR,5S,6aS,6bR,9aS,10aS,10bS,12S)-8-(3,3-Dimethyl-butyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 74 | Methanesulfonic acid 2-[(4aS,4bR,5S,6aS,6bR,9aS,10aS,10bS,12S)-4b,12-difluoro-5-hydroxy-4a,6a-dimethyl-2-oxo-8-(3-phenyl-propyl)-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 75 | methanesulfonic acid 2-((4aS,4bR,5S,6aS,6bR,9aS,10aS,10bS,12S)-4b,12-difluoro-8-furan-3-ylmethyl-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl)-2-oxo-ethyl ester |
| 76 | methanesulfonic acid 2-((4aR,4bS,5S,6aS,6bR,9aS,10aS,10bS)-8-furan-3-ylmethyl-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl)-2-oxo-ethyl ester |
| 77 | methanesulfonic acid 2-[(4aS,4bR,5S,6aS,6bR,9aS,10aS,10bS,12S)-8-(4-chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 78 | methanesulfonic acid 2-((4aR,4bS,5S,6aS,6bR,9aS,10aS,10bS)-8-benzyl-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl)-2-oxo-ethyl ester |
| 79 | methanesulfonic acid 2-((4aS,4bR,5S,6aS,6bR,9aS,10aS,10bS,12S)-4b,12-difluoro-5-hydroxy-4a,6a-dimethyl-2-oxo-8-thiophen-3-ylmethyl-2,4a,4b,5,6,6a,8,9,9a,10,10a,10b,11,12-tetradecahydro-7-oxa-8-aza-pentaleno[2,1-a]phenanthren-6b-yl)-2-oxo-ethyl ester |
| 80 | methanesulfonic acid 2-((4aS,4bR,5S,6aS,6bR,9aS,10aS,10bS,12S)-4b,12-difluoro-8-furan-2-ylmethyl-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl)-2-oxo-ethyl ester |

| Cpd. | Chemical Name |
|---|---|
| 81 | (4aR,4bS,5S,6aS,6bR,9aS,10aS,10bS)-6b-(2-Ethylsulfanyl-acetyl)-8-furan-3-ylmethyl-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 82 | thioacetic acid S-[2-((4aR,4bS,5S,6aS,6bR,9aS,10aS,10bS)-8-furan-3-ylmethyl-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl)-2-oxo-ethyl]ester |
| 83 | (4aS,4bR,5S,6aS,6bR,9aS,10aS,10bS,12S)-6b-(2-Ethylsulfanyl-acetyl)-4b,12-difluoro-8-furan-3-ylmethyl-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 84 | (4aS,4bR,5S,6aS,6bR,9aS,10aS,10bS,12S)-4b,12-Difluoro-8-furan-3-ylmethyl-5-hydroxy-4a,6a-dimethyl-6b-(2-methylsulfanyl-acetyl)-4a,4b,5,6,6a,6b,8,9,9a,10,10a,10b,11,12-tetradecahydro-7-oxa-8-aza-pentaleno[2,1-a]phenanthren-2-one |
| 85 | (4aS,4bR,5S,6aS,6bR,9aS,10aS,10bS,12S)-8-(4-Chloro-benzyl)-4b,12-difluoro-5-hydroxy-4a,6a-dimethyl-6b-(2-methylsulfanyl-acetyl)-4a,4b,5,6,6a,6b,8,9,9a,10,10a,10b,11,12-tetradecahydro-7-oxa-8-aza-pentaleno[2,1-a]phenanthren-2-one |
| 86 | (4aS,4bR,5S,6aS,6bR,9aS,10aS,10bS,12S)-6b-[2-(Benzothiazol-2-ylsulfanyl)-acetyl]-8-(4-chloro-benzyl)-4b,12-difluoro-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 87 | (4aS,4bR,5S,6aS,6bR,9aS,10aS,10bS,12S)-6b-[2-(Benzooxazol-2-ylsulfanyl)-acetyl]-8-(4-chloro-benzyl)-4b,12-difluoro-5-hydroxy-4a,6a-dimethyl-4a,4b,5,6,6a,6b,8,9,9a,10,10a,10b,14a,4b,5,6,6a,6b,8,9,9a,10,10a,10b,11,12-tetradecahydro-7-oxa-8-aza-pentaleno[2,1-a]phenanthren-2-one |
| 88 | (4aR,4bS,5S,6aS,6bR,9aS,10aS,10bS)-8-Furan-3-ylmethyl-5-hydroxy-6b-(2-mercapto-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 89 | (4aS,4bR,5S,6aS,6bR,9aS,10aS,10bS,12S)-6b-(2-Chloro-acetyl)-4b,12-difluoro-5-hydroxy-4a,6a-dimethyl-8-(3-phenyl-propyl)-4a,4b,5,6,6a,6b,8,9,9a,10,10a,10b,11,12-tetradecahydro-7-oxa-8-aza-pentaleno[2,1-a]phenanthren-2-one |
| 90 | (4aS,4bR,5S,6aS,6bR,9aS,10aS,10bS,12S)-6b-(2-Chloro-acetyl)-4b,12-difluoro-8-furan-3-ylmethyl-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 91 | (4aS,4bR,5S,6aS,6bR,9aS,10aS,10bS,12S)-6b-(2-Chloro-acetyl)-8-(4-chloro-benzyl)-4b,12-difluoro-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 92 | (4aS,4bR,5S,6aS,6bR,9aS,10aS,10bS,12S)-6b-(2-Chloro-acetyl)-4b,12-difluoro-8-furan-2-ylmethyl-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 93 | (4aR,4bS,5S,6aS,6bR,9aS,10aS,10bS)-8-Furan-3-ylmethyl-5-hydroxy-4a,6a-dimethyl-6b-[2-(2-oxo-tetrahydro-furan-3-ylsulfanyl)-acetyl]-4a,4b,5,6,6a,6b,8,9,9a,10,10a,10b,11,12-tetradecahydro-7-oxa-8-aza-pentaleno[2,1-a]phenanthren-2-one |
| 94 | (4aR,4bS,5S,6aS,6bR,9aS,10aS,10bS)-8-Benzyl-5-hydroxy-4a,6a-dimethyl-6b-[2-(2-oxo-tetrahydro-furan-3-ylsulfanyl)-acetyl]-4a,4b,5,6,6a,6b,8,9,9a,10,10a,10b,11,12-tetradecahydro-7-oxa-8-aza-pentaleno[2,1-a]phenanthren-2-one |
| 95 | (4aS,4bR,5S,6aS,6bR,9aS,10aS,10bS,12S)-6b-[2-(2-oxo-tetrahydro-furan-3-ylsulfanyl)-acetyl]-4b,12-difluoro-5-hydroxy-4a,6a-dimethyl-8-thiophen-2-ylmethyl-4a,4b,5,6,6a,6b,8,9,9a,10,10a,10b,11,12-tetradecahydro-7-oxa-8-aza-pentaleno[2,1-a]phenanthren-2-one |
| 96 | (4aS,4bR,5S,6aS,6bR,9aS,10aS,10bS,12S)-6b-[2-(2-oxo-tetrahydro-furan-3-ylsulfanyl)-acetyl]-4b,12-difluoro-8-furan-2-ylmethyl-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 97 | (4aR,4bS,5S,6aS,6bR,9aS,10aS,10bS)-5-Hydroxy-4a,6a-dimethyl-6b-[2-(tetrahydro-pyran-2-yloxy)-acetyl]-4a,4b,5,6,6a,6b,8,9,9a,10,10a,10b,11,12-tetradecahydro-7-oxa-8-aza-pentaleno[2,1-a]phenanthren-2-one |
| 98 | (4aR,4bS,5S,6aS,6bR,9aS,10aS,10bS)-8-Benzoyl-5-hydroxy-4a,6a-dimethyl-6b-[2-(tetrahydro-pyran-2-yloxy)-acetyl]-4a,4b,5,6,6a,6b,8,9,9a,10,10a,10b,11,12-tetradecahydro-7-oxa-8-aza-pentaleno[2,1-a]phenanthren-2-one |
| 99 | (4aS,4bR,5S,6aS,6bR,9aS,10aS,10bS,12S)-4b,12-Difluoro-8-(furan-2-carbonyl)-5-hydroxy-4a,6a-dimethyl-6b-[2-(tetrahydro-pyran-2-yloxy)-acetyl]-4a,4b,5,6,6a,6b,8,9,9a,10,10a,10b,11,12-tetradecahydro-7-oxa-8-aza-pentaleno[2,1-a]phenanthren-2-one |
| 100 | (4aR,4bS,5S,6aS,6bR,9aS,10aS,10bS)-8-Benzoyl-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 101 | (4aS,4bR,5S,6aS,6bR,9aS,10aS,10bS,12S)-4b,12-Difluoro-8-(furan-2-carbonyl)-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |

-continued

| Cpd. | Chemical Name |
|---|---|
| 102 | (4aR,4bS,5S,6aS,6bR,9aS,10aS,10bS)-8-(Furan-2-carbonyl)-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 103 | (4aR,4bS,5S,6aS,6bR,9aS,10aS,10bS)-5-Hydroxy-6b-(2-hydroxy-acetyl)-4a,6a-dimethyl-8-(thiophene-2-carbonyl)-4a,4b,5,6,6a,6b,8,9,9a,10,10a,10b,11,12-tetradecahydro-7-oxa-8-aza-pentaleno[2,1-a]phenanthren-2-one |
| 104 | (4aR,4bS,5S,6aS,6bR,9aS,10aS,10bS)-5-Hydroxy-6b-(2-hydroxy-acetyl)-4a,6a-dimethyl-8-(thiophene-3-carbonyl)-4a,4b,5,6,6a,6b,8,9,9a,10,10a,10b,11,12-tetradecahydro-7-oxa-8-aza-pentaleno[2,1-a]phenanthren-2-one |
| 105 | (4aR,4bS,5S,6aS,6bR,9aS,10aS,10bS)-5-Hydroxy-6b-(2-hydroxy-acetyl)-4a,6a-dimethyl-8-phenylacetyl-4a,4b,5,6,6a,6b,8,9,9a,10,10a,10b,11,12-tetradecahydro-7-oxa-8-aza-pentaleno[2,1-a]phenanthren-2-one |
| 106 | acetic acid 2-((4aR,4bS,5S,6aS,6bR,9aS,10aS,10bS)-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl)-2-oxo-ethyl ester |
| 107 | acetic acid 2-((4aR,4bS,5S,6aS,6bR,9aS,10aS,10bS)-5-hydroxy-8-methanesulfonyl-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl)-2-oxo-ethyl ester |
| 108 | (4aR,4bS,5S,6aS,6bR,9aS,10aS,10bS)-5-Hydroxy-6b-(2-hydroxy-acetyl)-8-methanesulfonyl-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 109 | acetic acid 2-[(4aR,4bS,5S,6aS,6bR,9aS,10aS,10bS)-5-hydroxy-4a,6a-dimethyl-8-(methyl-phenyl-carbamoyl)-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 110 | (4aR,4bS,5S,6aS,6bR,9aS,10aS,10bS)-5-Hydroxy-6b-(2-hydroxy-acetyl)-4a,6a-dimethyl-2-oxo-2,4a,4b,5,6,6a,6b,9,9a,10,10a,10b,11,12-tetradecahydro-7-oxa-8-aza-pentaleno[2,1-a]phenanthrene-8-carboxylic acid methyl-phenyl-amide |
| 111 | (4aR,4bS,5S,6aS,6bR,9aS,10aS,10bS)-5-Hydroxy-4a,6a-dimethyl-2-oxo-8-thiophen-3-ylmethyl-2,4a,4b,5,6,6a,8,9,9a,10,10a,10b,11,12-tetradecahydro-7-oxa-8-aza-pentaleno[2,1-a]phenanthrene-6b-carboxylic acid |
| 112 | (4aS,4bR,5S,6aS,6bR,9aS,10aS,10bS,12S)-4b,12-Difluoro-8-furan-3-ylmethyl-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 113 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 114 | (4aS,4bR,5S,6aS,6bR,9aS,10aS,10bS,12S)-4b,12-Difluoro-5-hydroxy-4a,6a-dimethyl-2-oxo-8-(3-phenyl-propyl)-2,4a,4b,5,6,6a,8,9,9a,10,10a,10b,11,12-tetradecahydro-7-oxa-8-aza-pentaleno[2,1-a]phenanthrene-6b-carboxylic acid |
| 115 | (4aS,4bR,5S,6aS,6bR,9aS,10aS,10bS,12S)-4b,12-Difluoro-5-hydroxy-4a,6a-dimethyl-2-oxo-8-thiophen-2-ylmethyl-2,4a,4b,5,6,6a,8,9,9a,10,10a,10b,11,12-tetradecahydro-7-oxa-8-aza-pentaleno[2,1-a]phenanthrene-6b-carboxylic acid |
| 116 | (4aR,4bS,5S,6aS,6bR,9aS,10aS,10bS)-5-Hydroxy-4a,6a-dimethyl-2-oxo-8-thiophen-3-ylmethyl-2,4a,4b,5,6,6a,8,9,9a,10,10a,10b,11,12-tetradecahydro-7-oxa-8-aza-pentaleno[2,1-a]phenanthrene-6b-carboxylic acid methyl ester |
| 117 | (4aS,4bR,5S,6aS,6bR,9aS,10aS,10bS,12S)-4b,12-Difluoro-5-hydroxy-4a,6a-dimethyl-2-oxo-8-(3-phenyl-propyl)-2,4a,4b,5,6,6a,8,9,9a,10,10a,10b,11,12-tetradecahydro-7-oxa-8-aza-pentaleno[2,1-a]phenanthrene-6b-carbothioic acid S-butyl ester |
| 118 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid methyl amide |
| 119 | (4aS,4bR,5S,6aS,6bR,9aS,10aS,10bS,12S)-4b,12-Difluoro-8-furan-3-ylmethyl-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-butyl ester |
| 120 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-butyl ester |
| 121 | (4aS,4bR,5S,6aS,6bR,9aS,10aS,10bS,12S)-4b,12-Difluoro-5-hydroxy-4a,6a-dimethyl-2-oxo-8-(3-phenyl-propyl)-2,4a,4b,5,6,6a,8,9,9a,10,10a,10b,11,12-tetradecahydro-7-oxa-8-aza-pentaleno[2,1-a]phenanthrene-6b-carboxylic acid butyl ester |
| 122 | (4aS,4bR,5S,6aS,6bR,9aS,10aS,10bS,12S)-4b,12-Difluoro-8-furan-3-ylmethyl-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid butyl ester |
| 123 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid butyl ester |
| 124 | ((4aS,4bR,5S,6aS,6bR,9aS,10aS,10bS,12S)-4b,12-Difluoro-5-hydroxy-4a,6a-dimethyl-2-oxo-2,4a,4b,5,6,6a,8,9,9a,10,10a,10b,11,12-tetradecahydro-7-oxa-8-aza-N-(2-thienylmethyl)-pentaleno[2,1-a]phenanthrene-6b-carbonylsulfanyl)-acetic acid ethyl ester |

| Cpd. | Chemical Name |
|---|---|
| 125 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-(2-oxo-tetrahydro-furan-3-yl) ester |
| 126 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid methyl ester |
| 127 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-methylcarbamoylmethyl ester |
| 128 | [(4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbonylsulfanyl]-acetic acid ethyl ester |
| 129 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid benzyl amide |
| 130 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid dimethylamide |
| 131 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid benzyl-methyl-amide |
| 132 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid (2,2,2-trifluoro-ethyl)-amide |
| 133 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid cyanomethyl-amide |
| 134 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid cyanomethyl-methyl-amide |
| 135 | (4aS,4bR,5S,6aS,6bR,9aS,10aS,10bS,12S)-4b,12-Difluoro-5-hydroxy-4a,6a-dimethyl-2-oxo-8-(3-phenyl-propyl)-2,4a,4b,5,6,6a,8,9,9a,10,10a,10b,11,12-tetradecahydro-7-oxa-8-aza-pentaleno[2,1-a]phenanthrene-6b-carboxylic acid chloromethyl ester |
| 136 | (4aS,4bR,5S,6aS,6bR,9aS,10aS,10bS,12S)-4b,12-Difluoro-8-furan-3-ylmethyl-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid chloromethyl ester |
| 137 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid chloromethyl ester |
| 138 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxyilic acid 2-hydroxy-ethyl ester |
| 139 | (4aS,4bR,5S,6aS,6bR,9aS,10aS,10bS,12S)-4b,12-Difluoro-5-hydroxy-4a,6a-dimethyl-2-oxo-8-(3-phenyl-propyl)-2,4a,4b,5,6,6a,8,9,9a,10,10a,10b,11,12-tetradecahydro-7-oxa-8-aza-pentaleno[2,1-a]phenanthrene-6b-carbothioic acid S-cyanomethyl ester |
| 140 | (4aS,4bR,5S,6aS,6bR,9aS,10aS,10bS,12S)-4b,12-Difluoro-8-furan-3-ylmethyl-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-cyanomethyl ester |
| 141 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-cyanomethyl ester |
| 142 | (4aS,4bR,5S,6aS,6bR,9aS,10aS,10bS,12S)-4b,12-Difluoro-8-furan-3-ylmethyl-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-chloromethyl ester |
| 143 | (4aS,4bR,5S,6aS,6bR,9aS,10aS,10bS,12S)-4b,12-Difluoro-5-hydroxy-4a,6a-dimethyl-2-oxo-8-(3-phenyl-propyl)-2,4a,4b,5,6,6a,8,9,9a,10,10a,10b,11,12-tetradecahydro-7-oxa-8-aza-pentaleno[2,1-a]phenanthrene-6b-carbothioic acid S-chloromethyl ester |
| 144 | (4aS,4bR,5S,6aS,6bR,9aS,10aS,10bS,12S)-4b,12-Difluoro-5-hydroxy-4a,6a-dimethyl-2-oxo-8-thiophen-2-ylmethyl-2,4a,4b,5,6,6a,8,9,9a,10,10a,10b,11,12- |

| Cpd. | Chemical Name |
|---|---|
| | tetradecahydro-7-oxa-8-aza-pentaleno[2,1-a]phenanthrene-6b-carbothioic acid S-cyanomethyl ester |
| 145 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-chloromethyl ester |
| 146 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-(3,3,3-Trifluoro-propyl) ester |
| 147 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-(2-fluoro-ethyl) ester |
| 148 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-(3,3,3-trifluoro-2,2-dihydroxy-propyl) ester |
| 149 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-methoxymethyl ester |
| 150 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-(2-cyano-ethyl) ester |
| 151 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-(2-ethoxy-ethyl) ester |
| 152 | Acetic acid (4aS,4bR,5S,6aS,6bR,9aS,10aS,10bS,12S)-8-(4-chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbonylsulfanylmethyl ester |
| 153 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-(2,2,2-trifluoro-ethyl) ester |
| 154 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-(2-oxo-butyl) ester |
| 155 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-but-2-ynyl ester |
| 156 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-(2-oxo-propyl) ester |
| 157 | (4aS,4bR,5S,6aS,6bR,9aS,10aS,10bS,12S)-4b,12-Difluoro-5-hydroxy-4a,6a-dimethyl-2-oxo-8-(3-phenyl-propyl)-2,4a,4b,5,6,6a,8,9,9a,10,10a,10b,11,12-tetradecahydro-7-oxa-8-aza-pentaleno[2,1-a]phenanthrene-6b-carbothioic acid S-iodomethyl ester |
| 158 | (4aS,4bR,5S,6aS,6bR,9aS,10aS,10bS,12S)-4b,12-Difluoro-5-hydroxy-4a,6a-dimethyl-2-oxo-8-(3-phenyl-propyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 159 | (4aS,4bR,5S,6aS,6bR,9aS,10aS,10bS,12S)-8-(4-Chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 160 | acetic acid 2-[(4aR,4bS,5S,6aS,6bR,9aS,10aS,10bS)-5-hydroxy-4a,6a-dimethyl-2-oxo-8-(3-phenyl-propyl)-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 161 | acetic acid 2-[(4aS,6aS,6bR,9aS,10aS,10bS)-4a,6a-dimethyl-2-oxo-8-(3-phenyl-propyl)-2,4a,6,6a,8,9,9a,10,10a,10b,11,12-dodecahydro-7-oxa-8-aza-pentaleno[2,1-a]phenanthren-6b-yl]-2-oxo-ethyl ester |
| 162 | acetic acid 2-[(4aS,4bR,5S,6aS,6bR,9aS,10aS,10bS)-4b-chloro-5-hydroxy-4a,6a-dimethyl-2-oxo-8-(3-phenyl-propyl)-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 163 | (4aS,4bR,5S,6aS,6bR,9aS,10aS,10bS)-4b-Chloro-5-hydroxy-6b-(2-hydroxy-acetyl)-4a,6a-dimethyl-8-(3-phenyl-propyl)-4a,4b,5,6,6a,6b,8,9,9a,10,10a,10b,11,12-tetradecahydro-7-oxa-8-aza-pentaleno[2,1-a]phenanthren-2-one |

-continued

| Cpd. | Chemical Name |
|---|---|
| 164 | (4aS,4bR,5S,6aS,6bR,9aS,10aS,10bS)-4b-Chloro-8-(4-chloro-benzyl)-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 165 | Propionic acid 2-((4aS,4bR,5S,6aS,6bR,9aS,10aS,10bS,12S)-4b,12-difluoro-5-hydroxy-4a,6a-dimethyl-2-oxo-8-thiophen-2-ylmethyl-2,4a,4b,5,6,6a,8,9,9a,10,10a,10b,11,12-tetradecahydro-7-oxa-8-aza-pentaleno[2,1-a]phenanthren-6b-yl)-2-oxo-ethyl ester |
| 166 | Propionic acid 2-[(4aS,4bR,5S,6aS,6bR,9aS,10aS,10bS,12S)-4b,12-difluoro-8-(4-fluoro-benzyl)-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 167 | Propionic acid 2-[(4aS,4bR,5S,6aS,6bR,9aS,10aS,10bS,12S)-8-(4-chloro-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl]-2-oxo-ethyl ester |
| 168 | Acetic acid 2-((4aS,4bR,5S,6aS,6bR,9aS,10aS,10bS,12S)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthren-6b-yl)-2-oxo-ethyl ester |
| 169 | Acetic acid 2-((4aS,4bR,5S,6aS,6bR,9aS,10aS,10bS,12S)-4b,12-difluoro-5-hydroxy-4a,6a-dimethyl-2-oxo-2,4a,4b,5,6,6a,8,9,9a,10,10a,10b,11,12-tetradecahydro-7-oxa-8-N-(1-methyl-2-oxo-1,2-dihydro-pyridin-3-ylmethyl)-aza-pentaleno[2,1-a]phenanthren-6b-yl)-2-oxo-ethyl ester |
| 170 | (4aS,4bR,5S,6aS,6bR,9aS,10aS,10bS,12S)-4b,12-Difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-N-(1-methyl-2-oxo-1,2-dihydro-pyridin-3-ylmethyl)-aza-pentaleno[2,1-a]phenanthren-2-one |
| 171 | (4aS,4bR,5S,6aS,6bR,9aS,10aS,10bS,12S)-4b,12-Difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-N-(2-yl-methyl-cyclopent-2-enone)-aza-pentaleno[2,1-a]phenanthren-2-one |
| 172 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(2-methyl-thiazol-4-ylmethyl)-4a,4b,5,6,6a,6b,8,9,9a,10,10a,10b,11,12-tetradecahydro-7-oxa-8-aza-pentaleno[2,1-a]phenanthren-2-one |
| 173 | (6S,8S,9R,10S,11S,13S,14S)-6,9-Difluoro-17-(2-fluoro-acetyl)-11-hydroxy-10,13-dimethyl-6,7,8,9,10,11,12,13,14,15-decahydro-cyclopenta[a]phenanthren-3-one |
| 174 | 4aS,4bR,5S,6aS,6bR,9aS,10aS,10bS,12S)-8-(4-Chloro-benzyl)-4b,12-difluoro-6b-(2-fluoro-acetyl)-5-hydroxy-4a,6a-dimethyl-4a,4b,5,6,6a,6b,8,9,9a,10,10a,10b,11,12-tetradecahydro-7-oxa-8-aza-pentaleno[2,1-a]phenanthren-2-one |

The compounds of general formula (I) and (I') may be prepared conventionally according to methods disclosed in the art. Some of the processes which can be used for the preparation of the compounds of formula (I'), may also be applied to compounds of formula (I), as described in the Scheme below.

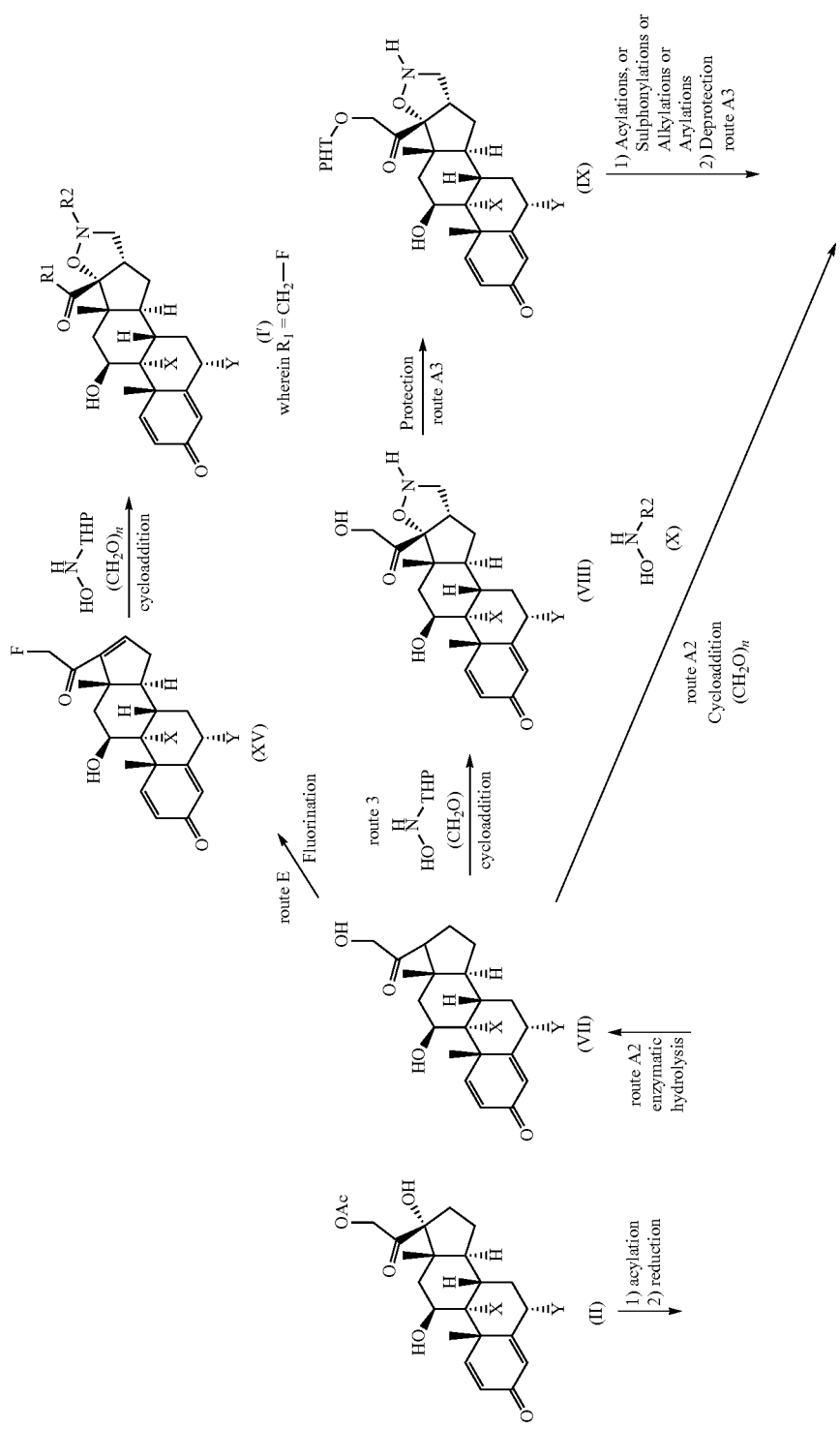

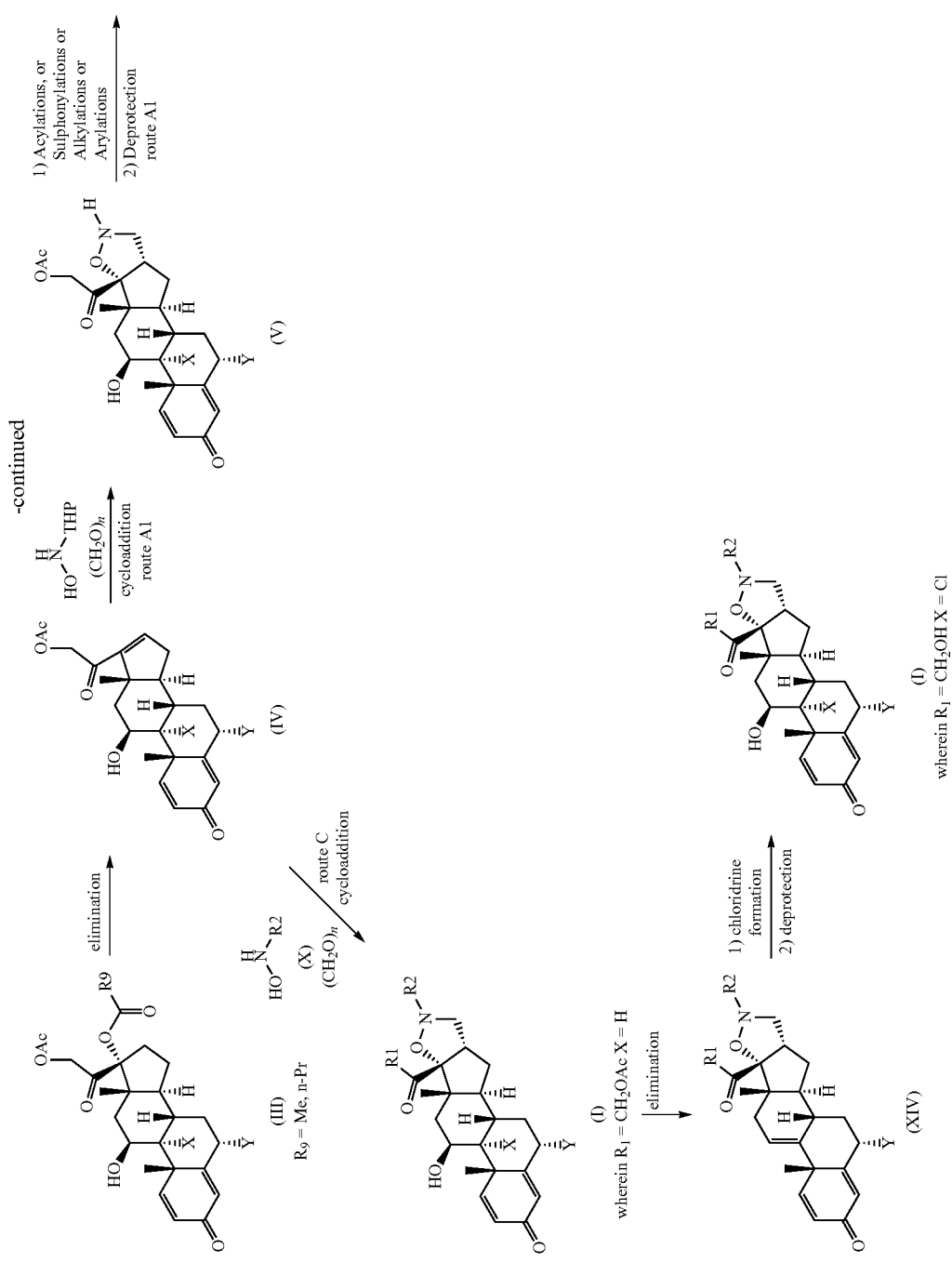

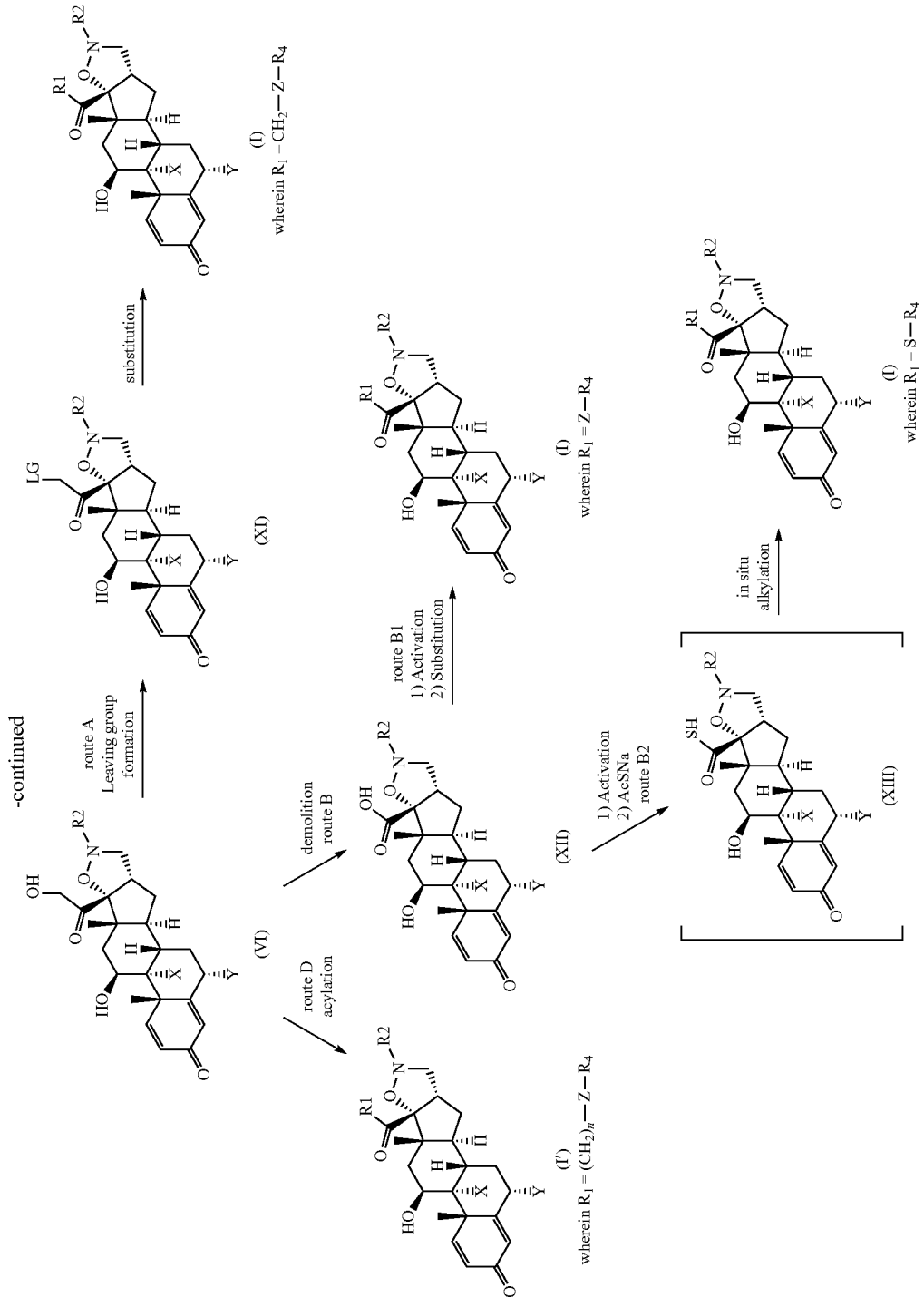

Procedure for the Preparation of the Compounds of the Invention.

According to a particular embodiment of the present invention, the compounds of the invention may be prepared according to different routes described in scheme, depending on the substituents R1, R2, X and Y.

Route A1—reaction of compounds of general formula (IV) with N-tetrahydropyranyl hydroxylamine (HO—NH-THP), to prepare a compound of formula (V) can be conveniently conducted in a protic solvent such as EtOH at a temperature ranging from 80 to 100° C. The THP protecting group is directly cleaved in the reaction conditions.

These compounds may be further functionalized with alkyl halides, acyl halides, isocyanates, carbamoyl chlorides or sulphonyl chlorides using method readily apparent for those skilled in the art (*J. Med. Chem.*, pp. 379-388, 1995; *J. C. S. Chem. Comm.*, pp. 256-257, 1985), to give compounds of general formula (VI). These reactions are usually carried out in a solvent such as dichloromethane (DCM) or tetrahydrofuran (THF) and proceed at a temperature range from room temperature (RT) to reflux. A base such as triethylamine or diisopropylethylamine may be required to promote the reaction. The reaction with aryl halides may be performed under the known copper catalyzed N-arylation of isoxazolidine (*Bioorg. Med. Chem. Lett.*, p. 2834, 2005). The acetyl ester may be easily hydrolyzed using standard conditions for the deacetylation of alcohols, treating for example the compound with a base such as sodium or potassium hydroxide or potassium carbonate in a suitable solvent (e.g. methanol or ethanol). This reaction usually proceeds at room temperature (RT) over a period of 1 to 5 hours leading to compounds of general formula (VI).

Compounds of general formula (IV) may be conveniently prepared according to standard procedures reported in the literature. For instance they may be prepared by treatment of compounds of general formula (III) with a base such as potassium acetate. This reaction is usually performed in a suitable polar solvent such as dimethylformamide (DMF) and typically proceeds at a temperature range from 80 to 110° C., over a period of 0.5 to 4 hours.

Compounds of formula (III) may be readily prepared from known compounds by methods well known to those skilled in the art, starting from compounds of general formula (II) (*J. Med. Chem.* 1982, vol. 25, pp. 1492-1495).

Route A2—alternatively, the compounds of general formula (VI) may be prepared starting from the reaction of a compound of formula (VII) with a compound of formula (X) in the presence of paraformaldehyde, using known procedures for the isoxazolidine formation, by cycloaddition of nitrones (*J. Med. Chem.*, vol. 25, pp. 1492-1495, 1982). The reaction is conveniently carried out in a protogenic solvent, such as ethanol, at temperatures ranging from 80 to 100° C. Hydroxylamine of formula (X) are either commercially available or may be easily prepared using procedures well known for those skilled in the art, for example by reducing an oxime with a reducing agent, such as borane pyridine complex (*J. Med. Chem.*, vol. 40, pp. 1955-1968, 1997) or by reaction of O-tetrahydropyranyl hydroxylamine with a suitable alkylating agent such as alkyl halides (*Chem. Pharm. Bull.*, vol. 46, pp. 966-972, 1998).

The compounds of formula (VII) may be prepared hydrolyzing the compounds of formula (IV). This reaction is preferably carried out by subjecting compounds (IV) to the action of an enzyme, such as immobilized Lipase from *Candida Antarctica* (Sigma Aldrich) (*Tetrahedron*, vol. 50, pp. 13165-13172, 1994).

Route A3—compounds of general formula (VIII) may be prepared starting from the reaction of a compound of formula (VII) with HO—NH-THP. This reaction may be conveniently conducted in dioxane or in a protic solvent such as EtOH at a temperature ranging from 80 to 100° C. The THP protecting group is directly cleaved in the reaction conditions. The obtained (VIII) can be conveniently and selectively protected by treatment with dihydropyrane in a suitable solvent such as DCM or THF, at temperature from 0° C. to RT, to obtain compound of formula (IX). The reaction is complete in time ranging from 0.5 to 3 hours. Compounds of formula (IX) may be further functionalized with alkyl halides, acyl halides, isocyanates, carbamoyl chlorides or sulphonyl chlorides as described in Route A1. The THP protecting group can be easily removed by treating the protected intermediate with HCl in a suitable solvent, such as THF or dioxane. This reaction usually proceeds at RT over a period of 1 to 15 hours leading to compounds of general formula (VI).

Route A—conversion of the hydroxyl group of 2-hydroxy acetyl moiety at position 6b of compounds of general formula (VI) into a leaving group (LG) of compounds of general formula (XI) can be carried out by treating compounds of formula (VI) with methanesulfonyl chloride or p-toluenesulphonyl chloride (March's, "Advanced Organic Chemistry", Wiley-Interscience), in a suitable solvent, such as pyridine. This reaction is usually performed at RT over a period of 1 to 5 hours.

The LG of compounds of general formula (XI) may be easily displaced by nucleophiles such as halide anions, alcohols, thiols, thioacids, amines, amides and carbanions (*J. Org. Chem.*, p. 1042, 1999; *J. Steroid. Biochem.*, vol. 13, pp. 311-322, 1980), to obtain compounds of general formula (I) and (I') wherein R1=$(CH_2)_n$—Z—$(CH_2)_{n'}$—R4, wherein n=0, Z and R4 are as defined above. The reaction is usually performed in a suitable solvent, such as DCM, THF or dimethylformamide (DMF), in a range of temperature from 0 to 80° C. over a period of 1 to 5 hours and may be promoted by a base such as sodium or potassium carbonate or sodium hydride. The obtained product may be further functionalized modifying the moiety introduced by the described nucleophilic substitution reaction.

Route B—reaction of compounds of formula (VI) under well known oxidation conditions to obtain the intermediates of general formula (XII). This reaction is usually performed in open air at room RT over a period of 12 to 48 hours, in a suitable solvent such as THF in the presence of aqueous solution of an inorganic base, such as sodium or potassium hydroxide.

Route B1—conversion of the intermediates of formula (XII) into compounds of general formula (I) and (I') wherein R1=$(CH_2)_n$—Z—$(CH_2)_{n'}$—R4 wherein n=0, Z and R4 are as defined above, by treating the acid (XII) with one or more equivalents of an acid activating agent such as carbonyldiimidazole. The reaction is usually performed in a suitable polar solvent such as DMF, in a range of temperature from 0 to 80° C. over a period of 1 to 2 hours. The activated acid may be reacted with a nucleophile, such as alcohols, thiols, thioacids and amines. The reaction may be promoted by a base such as sodium or potassium carbonate, sodium hydride and proceeds at a temperature ranging from 0 to 20° C. over a period of 1 to 24 hours.

Alternatively, the intermediates of formula (XII) may be converted into the corresponding acyl chloride under well known conditions, using oxalyl chloride in a suitable solvent such as DCM. The activated intermediate may be reacted with a nucleophile such as alcohols, thiols, thioacids, amines and carbanions such as alkyl, aryl and heteroaryl cuprates or other metallorganic compounds reported in the literature, to be suitable for the conversion of acyl chlorides into the corresponding ketones.

Route B2—conversion of intermediates of formula (XII) into compounds of general formula (XIII), derived from reaction of acid (XII) with carbonyldiimidazole, followed by reaction with the sodium salt of thioacetic acid and/or hydrogen sulphide anhydrous. The reaction is usually performed by adding the solution of the preformed salt in the reaction solvent to the solution of the activated acid at a temperature ranging from 0 to 20° C. The thioacid intermediate (XIII) readily formed is in situ reacted with an alkylating reagent, such as bromoalkanes, leading to thioesters of general formula (I) and (I') wherein $R1=(CH_2)_n$—Z—$(CH_2)_{n'}$—R4, wherein n=0, Z=S and R4 is as defined above. The choice of suitable bromoalkane, such as bromo-chloromethane, may allow the preparation of compounds of formula (I) and (I') wherein $R1=(CH_2)_n$—Z—$(CH_2)_{n'}$—R4, wherein n=0, Z=S and R4 is as defined above, that may be further modified. For example, the reaction of these compounds in which R4 is chloromethyl with potassium iodide, followed by treatment with silver fluoride, may allow the preparation of compounds of formula (I) and (I') in which R4=fluoromethyl. These reactions are well known to those skilled in the art (*J. Med. Chem.*, vol. 37, pp. 3717-3729, 1994).

Route C—reaction of the intermediates of general formula (IV) with hydroxylamines of formula (X) in the presence of paraformaldehyde using known procedures for the isoxazolidine formation by cycloaddition of nitrones. The reaction is conveniently performed in a protogenic solvent, such as ethanol. The reaction is conveniently carried out at high temperature, for example from 60 to 85° C. and leads to compounds of general formula (I) and (I') wherein $R1=(CH_2)_n$—Z—$(CH_2)_{n'}$—R4, wherein n=1, Z=O and R4=Ac.

The intermediates of general formula (XIV) may be prepared by treating compounds of general formula (I) and (I') wherein $R1=(CH_2)_n$—Z—$(CH_2)_{n'}$—R4, wherein n=1, Z=O, R4=Ac and X=H, with methanesulfonyl chloride in a suitable solvent, such as DMF, in the presence of a base, such as pyridine. The reaction proceeds at a temperature ranging from 80 to 100° C. over a period of 1 to 5 hours.

Reacting compounds of formula (XIV) under well known conditions for the preparation of chlorohydrine starting from the corresponding alkene, it is possible to obtain compounds of general formula (I) and (I') wherein $R1=(CH_2)_n$—Z—$(CH_2)_{n'}$—R4, wherein n=1, Z=O, R4=H and X=Cl. The reaction involves the use of a chlorinating agent, such as N-chlorosuccinimide or dichloro-5,5-dimethylhydantoin, and is promoted by an acid such as perchloric acid. The reaction is usually carried out in a polar solvent such as THF, in a range of temperature from 0 to 20° C. over a period of 1 to 4 hours. The acetyl ester of compounds of formula (XIV) may be easily hydrolyzed using standard conditions for the deacetylation of alcohols, treating for example the compound with a base such as sodium or potassium carbonate in a solvent such as methanol or ethanol. This reaction usually proceeds at low temperature, ranging from 0 to 20° C., over a period of 0.5 to 2 hours.

Route D—reaction of the intermediates of general formula (VI) with acyl chlorides, using procedures well known for those skilled in the art. The reaction is conveniently performed in DCM as solvent in the presence of a base such as triethylamine, at room temperatures over a period of 20 to 50 hours. This procedure may allow the preparation of compounds of formula (I') wherein $R1=(CH_2)_n$—Z—$(CH_2)_{n'}$—R4, wherein n=1, Z=O, R4 are as defined above.

Route E—one pot procedure for the synthesis of compounds of general formula (XV) and subsequent cycloaddition reaction to afford compounds of general formula (I'). The first step of this procedure entails the formation of the corresponding mesylate at C21, starting from the intermediate (VII), by the well known conditions with mesyl chloride and N,N-diisopropylethylamine (DIPEA) in dry acetonitrile. Then, introduction of fluorine atom can be conveniently performed by in situ addition of tetra-n-butylammonium fluoride (TBAF) and KI and heating over a period of 8 to 20 hours. Cycloaddition reaction of the obtained intermediate (XV) with hydroxylamines of formula (X) in the presence of paraformaldehyde, under the known conditions described in Route C, lead to the formation of compounds of general formula (I'), in which $R1=CH_2$—F and R2 as defined above.

Advantageously, the compounds of the invention may be administered for example, at a dosage comprised between 0.001 and 1000 mg/day, preferably between 0.1 and 500 mg/day.

When they are administered by inhalation route, the dosage of the compounds of general formula (I) and (I') is advantageously comprised between 0.01 and 20 mg/day, preferably between 0.1 and 10 mg/day.

Preferably, the compounds of the invention alone or combined with other active ingredients may be administered for the prevention and/or treatment of any obstructive respiratory disease such as asthma, chronic bronchitis and chronic obstructive pulmonary disease (COPD).

However the compounds of the invention may be administered for the prevention and/or treatment of any disease wherein the decrease in the number, activity and movement of inflammatory cells is involved.

Examples of such diseases include: diseases involving inflammation such as asthma and other allergic disorders, COPD, acute rhinitis; reverse acute transplant rejection and acute exacerbations of selected autoimmune disorders, graft-versus-host disease in bone-marrow transplantation; autoimmune disorders such as rheumatoid and other arthritis; skin conditions such as systemic lupus erythematosus, systemic dermatomyositis, psoriasis; inflammatory bowel disease, inflammatory ophthalmic diseases, autoimmune hematologic disorders, and acute exacerbations of multiple sclerosis; kidney, liver, heart, and other organ transplantation; Behçet's acute ocular syndrome, endogenous uveitis, atopic dermatitis, inflammatory bowel disease, and nephrotic syndrome; Hodgkin's disease and non-Hodgkin's lymphoma, multiple myeloma and chronic lymphocytic leukemia (CLL); autoimmune hemolytic anemia and thrombocytopenia associated with CLL; leukemia and malignant lymphoma.

Preferably the compounds of the invention may be administered for the prevention and/or treatment of respiratory diseases such as from mild to acute severe conditions of asthma and COPD.

Other features of the invention will become apparent in the course of the following descriptions of exemplary embodiments which are given for illustration of the invention and are not intended to be limiting thereof.

EXAMPLES

Example 1

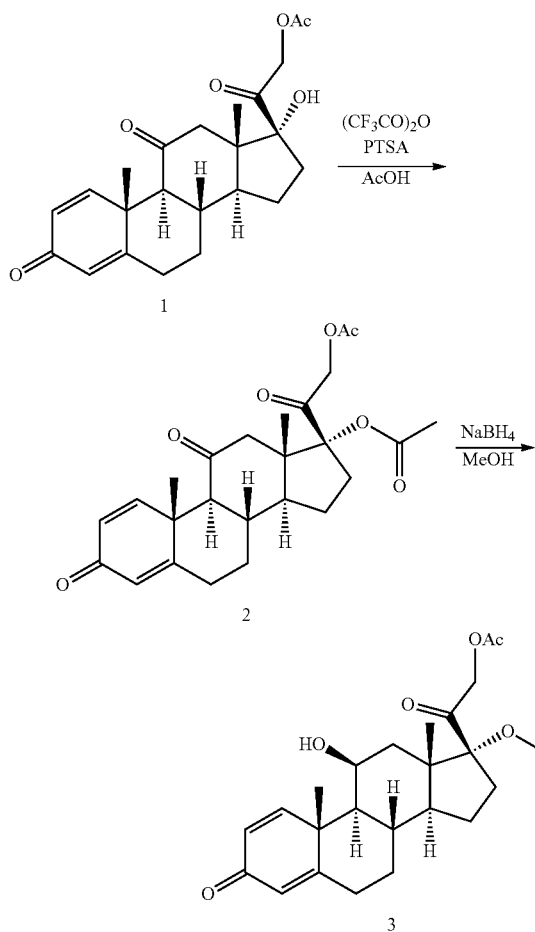

Preparation of acetic acid 2-((10R,13S,17R)-17-acetoxy-10,13-dimethyl-3,11-dioxo 6,7,8,9,10,11,12,13,14,15,16,17-dodecahydro-3H-cyclopenta[a]phenanthren-17-yl)-2-oxo-ethyl ester (Intermediate 2)

To a suspension of acetic acid 2-((10R,13S,17R)-17-hydroxy-10,13-dimethyl-3,11-dioxo-6,7,8,9,10,11,12,13,14,15,16,17-dodecahydro-3H-cyclopenta[a]phenanthren-17-yl)-2-oxo-ethyl ester (intermediate 1) (2 g, 4.99 mmol) and p-toluene sulphonic acid (PTSA) (200 mg, 1.051 mmol) in acetic acid (5 ml), at 0° C., trifluoroacetic anhydride (5 ml, 35.4 mmol) was slowly added over 10 minutes. After stirring at 0° C. for 20 minutes, the reaction mixture was stirred at RT for 3 hours.

The reaction mixture was poured in ice/water (130 ml) and the resulting mixture was extracted with DCM (2×100 ml) and AcOEt (2×100 ml). The combined organic extracts were dried over anhydrous $Na_2SO_4$ and concentrated. The crude product was purified by flash chromatography on silica gel, in gradient elution from DCM to DCM AcOEt 50:50 to give the title compound (2.64 g, quantitative yield).

LC-MS (ESI POS): 445.2 (MH+)

Preparation of acetic acid (10R,11S,13S,17R)-17-(2-acetoxy-acetyl)-11-hydroxy-10,13-dimethyl-3-oxo-6,7,8,9,10,11,12,13,14,15,16,17-dodecahydro-3H-cyclopenta[a]phenanthren-17-yl ester (Intermediate 3)

To an ice cooled solution of (intermediate 2) (2.64 g, 5.97 mmol) in THF (15 ml) and MeOH (15.00 ml), sodium borohydride (221 mg, 5.84 mmol) was added in portions over a period of 2.5 hours. The reaction mixture was poured into 1 N HCl and ice (150 ml). The formed precipitate was extracted with AcOEt (3×100 ml), and the combined organic layers were dried over anhydrous $Na_2SO_4$ and concentrated. The crude material was purified by flash chromatography on silica gel, in gradient elution from DCM to DCM/AcOEt 40:60 to afford the title compound (1.21 g, 45.6% yield).

$^1$H NMR (300 MHz, CHLOROFORM-d) ppm 7.28 (d, 1H), 6.30 (dd, 1H), 6.05 (t, 1H), 4.92 (d, 1H), 4.69 (d, 1H), 4.48-4.58 (m, 1H), 2.75-2.91 (m, 1H), 2.61 (m, 1H), 2.37 (ddd, 1H), 2.18-2.21 (m, 3H), 2.09-2.28 (m, 3H), 2.07 (s, 3H), 1.74-1.98 (m, 3H), 1.51-1.70 (m, 1H), 1.48 (s, 3H), 1.26-1.39 (m, 2H), 1.11-1.19 (m, 1H), 1.05 (s, 3H)

LC-MS (ESI POS): 445.2 (MH+)

Example 2

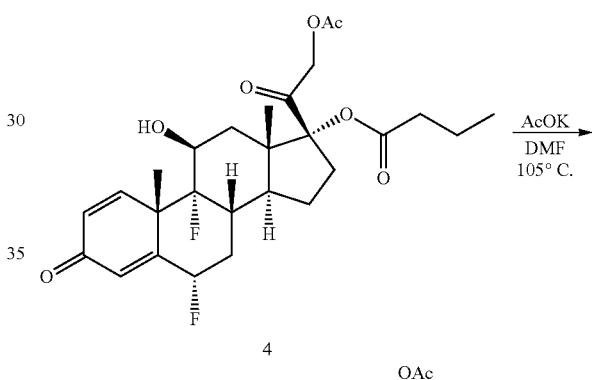

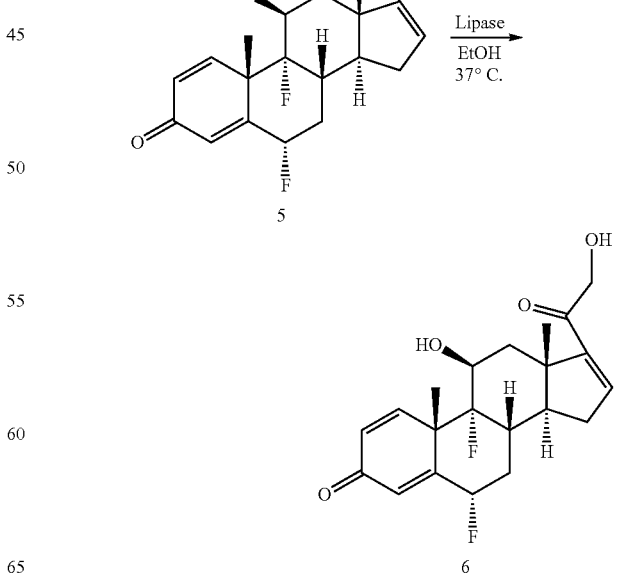

Preparation of acetic acid 2-((6S,9R,10S,11S,13S)-6,
9-difluoro-11-hydroxy-10,13-dimethyl-3-oxo-6,7,8,
9,10,11,12,13,14,15-decahydro-3H-cyclopenta[a]
phenanthren-17-yl)-2-oxo-ethyl ester (Intermediate
5)

To a solution of butyric acid (9R,10S,11S,13S,17R)-17-(2-acetoxy-acetyl)-9-chloro-11-hydroxy-10,13-dimethyl-3-oxo-6,7,8,9,10,11,12,13,14,15,16,17-dodecahydro-3H-cyclopenta[a]phenanthren-17-yl ester (intermediate 4) (2.48 g, 4.88 mmol) in anhydrous DMF (60 ml), under nitrogen atmosphere, potassium acetate (3.83 g, 39.0 mmol) was added, and the reaction mixture was stirred at 100° C. for 1.5 hours. The cooled reaction mixture was poured into ice and brine (200 ml), and the aqueous layer was extracted with AcOEt (3×150 ml). The combined organic extracts were washed with water and brine, dried over $Na_2SO_4$ and concentrated to afford 2.55 g of crude title compound which was used in the next step without further purification.

$^1$H NMR (300 MHz, DMSO-$d_6$): ppm 7.29 (dd, 1H), 6.99 (dd, 1H), 6.29 (dd, 1H), 5.98-6.15 (m, 1H), 5.68 (dddd, 1H), 5.56 (dd, 1H), 5.10 (d, 1H), 4.92 (d, 1H), 3.98-4.23 (m, 1H), 2.56-2.83 (m, 1H), 2.26-2.44 (m, 3H), 2.14-2.26 (m, 1H), 2.09 (s, 3H), 1.71-1.87 (m, 1H), 1.55-1.65 (m, 2H), 1.53 (s, 3H), 1.15 (s, 3H).

LC-MS (ESI POS): 421.97 (MH+)

Preparation of (6S,9R,10S,11S,13S)-6,9-Difluoro-
11-hydroxy-17-(2-hydroxy-acetyl)-10,13-dimethyl-
6,7,8,9,10,11,12,13,14,15-decahydro-cyclopenta[a]
phenanthren-3-one (Intermediate 6)

To a solution of (intermediate 5) (2.55 g, 6.06 mmol) in ethanol (100 ml), *Candida Antarctica* Lipase (2 U/mg) (510 mg, 6.06 mmol) was added and the reaction mixture was stirred at 37° C. overnight. The reaction mixture was filtered, washing with methanol, and the residue was purified by flash chromatography on silica gel, in gradient elution from DCM/AcOEt 90:10 to DCM/AcOEt 50:50, to afford 1.62 g of title compound (70.6% yield).

$^1$H NMR (300 MHz, DMSO-$d_6$): ppm 7.29 (dd, 1H), 6.87 (dd, 1H), 6.29 (dd, 1H), 6.09-6.17 (m, 1H), 5.67 (dddd, 1H), 5.53 (dd, 1H), 4.77 (t, 1H), 4.44 (dd, 1H), 4.26 (dd, 1H), 4.04-4.15 (m, 1H), 2.56-2.79 (m, 1H), 2.39 (dd, 1H), 2.25-2.35 (m, 2H), 2.09-2.25 (m, 1H), 1.76 (td, 1H), 1.55-1.66 (m, 2H), 1.53 (s, 3H), 1.17 (s, 3H).

LC-MS (ESI POS): 379.99 (MH+)

Intermediates 7 and 8 listed in Table 1 were prepared as previously described for intermediates 5 and 6, starting from intermediate 3.

TABLE 1

| Intermediate | Structure | Yield | Analytical |
|---|---|---|---|
| 7 | 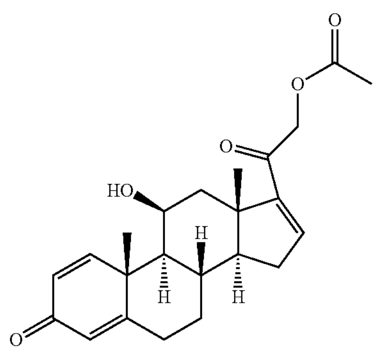 | 50% | LC-MS (ESI POS): 385.45 (MH+)<br>$^1$H NMR (300 MHz, CHLOROFORM-d) ppm 7.32 (d, 1 H), 6.74 (dd, 1 H), 6.29 (dd, 1 H), 6.03 (t, 1 H), 5.02 (d, 1 H), 4.88 (d, 1 H), 4.36-4.51 (m, 1 H), 2.55-2.73 (m, 1 H), 2.21-2.54 (m, 5 H), 2.19 (s, 3 H), 2.05-2.18 (m, 1 H), 1.66 (dd, 1 H), 1.51 (s, 3 H), 1.28 (s, 3 H), 1.04-1.44 (m, 4 H) |
| 8 | 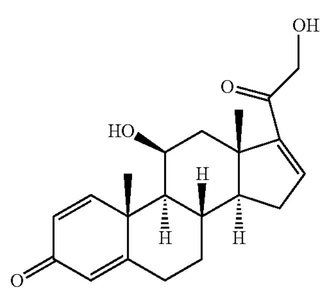 | 94% | LC-MS (ESI POS): 343.2 (MH+)<br>$^1$H NMR (300 MHz, DMSO-$d_6$) ppm 7.34 (d, 1 H), 6.83 (dd, 1 H), 6.16 (dd, 1 H), 5.92 (t, 1 H), 4.80 (d, 1 H), 4.74 (t, 1 H), 4.42 (dd, 1 H), 4.23 (dd, 1 H), 4.15-4.23 (m, 1 H), 2.53-2.67 (m, 1 H), 2.43 (dd, 1 H), 1.94-2.39 (m, 5 H), 1.42-1.48 (m, 1 H), 1.39 (dd, 1 H), 1.17 (s, 3 H), 0.74-1.33 (m, 5 H) |

Example 3

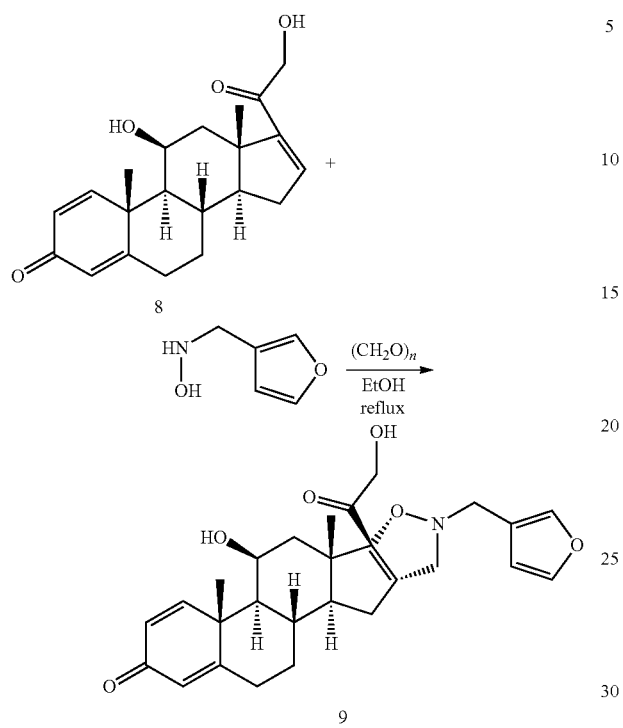

Preparation of (4aR,5S,6aS,6bR,9aS)-8-Furan-3-ylmethyl-5-hydroxy-6b-(2-hydroxy-acetyl)-4-a,6a-dimethyl-4-a,4b,5,6,6a,6b,8,9,9a,10,10a,10b,11,12-tetradecahydro-7-oxa-8-aza-pentaleno[2,1-a]phenanthren-2-one (Compound 9)

A mixture of (intermediate 8) (100 mg, 0.292 mmol), N-(furan-3-ylmethyl)-hydroxylamine (33 mg, 0.292 mmol) and paraformaldehyde (50 mg, 0.999 mmol) in ethanol (5 ml) was stirred at 105° C. overnight. The solvent was evaporated, and the residue was purified by preparative HPLC, to afford 58 mg of pure compound (42% yield).

$^1$H NMR (300 MHz, CHLOROFORM-d): ppm 7.38 (t, 1H), 7.32-7.36 (m, 1H), 7.25 (d, 1H), 6.36 (dd, 1H), 6.30 (dd, 1H), 6.05 (t, 1H), 4.45-4.63 (m, 1H), 4.45 (d, 1H), 4.10 (d, 1H), 3.76 (d, 1H), 3.70 (d, 1H), 3.38-3.61 (m, 2H), 2.90 (br. s., 1H), 2.48-2.69 (m, 1H), 2.36 (ddd, 1H), 2.14-2.29 (m, 1H), 2.03-2.14 (m, 2H), 1.99 (dd, 1H), 1.65-1.85 (m, 2H), 1.49-1.67 (m, 4H), 1.47 (s, 3H), 1.04-1.21 (m, 1H), 0.96 (s, 3H).

LC-MS (ESI POS): 468.18 (MH+)

The compounds listed in Table 2 were prepared as previously described for compound 9, by cycloaddition of intermediate 6 or 8 with a suitable hydroxylamine. Final compounds were purified by silica gel column chromatography or preparative HPLC.

TABLE 2

| Compound | Structure | Yield | Analytical |
|---|---|---|---|
| 10 | 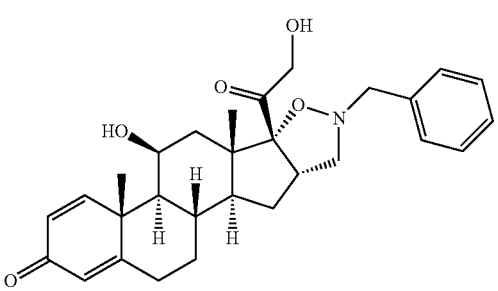 | 39% | LC-MS (ESI POS): 478.37 (MH+)<br>$^1$H NMR (300 MHz, CHLOROFORM-d) ppm 7.24-7.40 (m, 5 H), 7.25 (d, 1 H), 6.31 (dd, 1 H), 6.06 (t, 1 H), 4.39-4.56 (m, 1 H), 4.20-4.36 (m, 1 H), 3.99 (dd, 1 H), 3.89 (d, 1 H), 3.83 (d, 1 H), 3.36-3.64 (m, 2 H), 2.84 (t, 1 H), 2.51-2.70 (m, 1 H), 2.37 (ddd, 1 H), 2.17-2.29 (m, 1 H), 2.03 2.17 (m, 2 H), 1.98 (dd, 1 H), 1.64-1.85 (m, 1 H), 1.50-1.61 (m, 1 H), 1.47 (s, 3 H), 1.08-1.37 (m, 4 H), 0.95 (s, 3 H) |
| 11 | 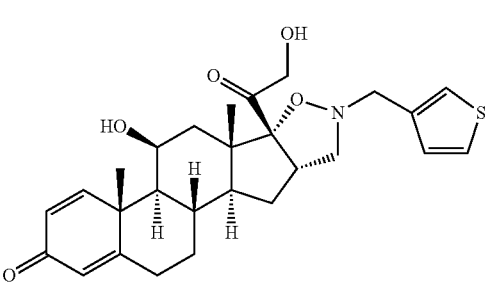 | 22% | LC-MS (ESI POS): 484.14 (MH+)<br>$^1$H NMR (300 MHz, CHLOROFORM-d) ppm 7.28 (dd, 4 H), 7.25 (d, 1 H), 7.14 (dd, 1 H), 7.02 (dd, 1 H), 6.30 (dd, 1 H), 6.05 (t, 1 H), 4.43-4.55 (m, 1 H), 4.35 (d, 1 H), 4.06 (dd, 1 H), 3.93 (d, 1 H), 3.86 (d, 1 H), 3.35-3.62 (m, 2 H), 2.76-3.04 (m, 1 H), 2.51-2.71 (m, 1 H), 2.37 (ddd, 1 H), 2.03-2.29 (m, 3 H), 1.99 (dd, 1 H), 1.50-1.82 (m, 3 H), 1.47 (s, 3 H), 1.16 (dd, 1 H), 0.95 (s, 3 H) |

TABLE 2-continued

| Compound | Structure | Yield | Analytical |
|---|---|---|---|
| 12 | 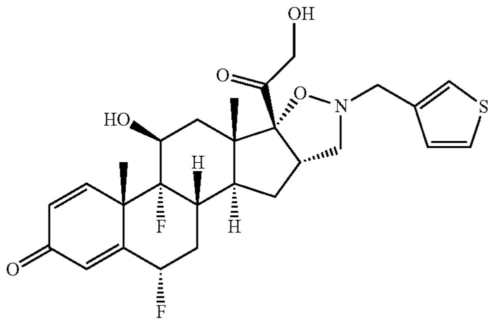 | 33% | LC-MS (ESI POS): 520.10 (MH+)<br>$^1$H NMR (300 MHz, CHLOROFORM-d) ppm 7.21-7.33 (m, 1 H), 7.15 (dd, 1 H), 7.11 (dd, 1 H), 7.02 (dd, 1 H), 6.44-6.50 (m, 1 H), 6.40 (dd, 1 H), 5.41 (dddd, 1 H), 4.23-4.53 (m, 1 H), 4.23-4.51 (m, 1 H), 4.07 (dd, 1 H), 3.96 (d, 1 H), 3.90 (d, 1 H), 3.33-3.66 (m, 2 H), 2.85 (t, 1 H), 2.20-2.67 (m, 4 H), 1.93-2.22 (m, 1 H), 1.62-1.92 (m, 2 H), 1.54 (s, 3 H), 1.42-1.57 (m, 2 H), 0.95 (s, 3 H) |
| 13 | 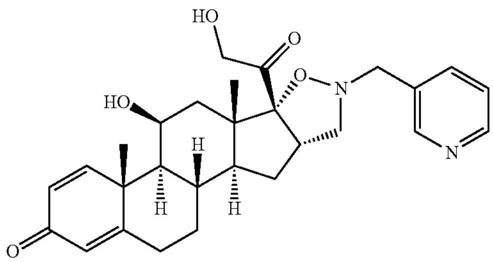 | 7% | LC-MS (ESI POS): 479.16 (MH+)<br>$^1$H NMR (300 MHz, DMSO-d6) ppm 8.36-8.55 (m, 2 H), 7.68 (dt, 1 H), 7.34 (ddd, 1 H), 7.31 (d, 1 H), 6.17 (dd, 1 H), 5.94 (t, 1 H), 4.70 (d, 1 H), 4.54-4.67 (m, 1 H), 4.15-4.40 (m, 1 H), 3.97 (d, 1 H), 3.75 (d, 1 H), 3.66-4.07 (m, 2 H), 3.44-3.63 (m, 1 H), 3.30-3.44 (m, 1 H), 2.53-2.64 (m, 1 H), 2.22-2.43 (m, 1 H), 1.91-2.21 (m, 3 H), 1.41-1.76 (m, 5 H), 1.38 (s, 3 H), 1.01-1.15 (m, 1 H), 0.97 (dd, 1 H), 0.79 (s, 3 H) |
| 14 | 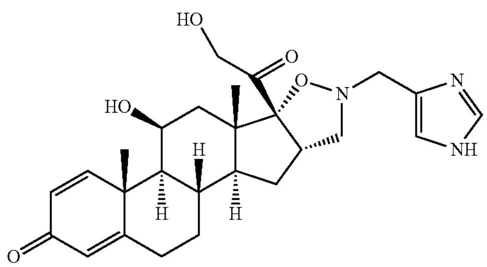 | 18% | LC-MS (ESI POS): 468.09 (MH+)<br>1H NMR (300 MHz, DMSO-d6) ppm 11.85 (br. s, 1 H), 7.50 (d, 1 H), 7.31 (d, 1 H), 6.17 (dd, 1 H), 5.93 (s, 1 H), 4.70 (d, 1 H), 4.55-4.67 (m, 1 H), 4.28 (br. s., 2 H), 4.13-4.37 (m, 1 H), 3.91-4.02 (m, 1 H), 3.54-4.01 (m, 2 H), 3.33-3.52 (m, 2 H), 2.54-2.62 (m, 1 H), 2.25-2.36 (m, 1 H), 1.92-2.12 (m, 4 H), 1.49-1.76 (m, 4 H), 1.39 (s, 3 H), 0.91-1.13 (m, 2 H), 0.81 (s, 3 H) |
| 15 | 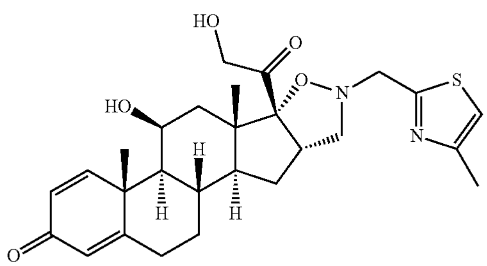 | 30% | LC-MS (ESI POS): 468.09 (MH+)<br>$^1$H NMR (300 MHz, DMSO-d6) ppm 11.85 (br. s., 1 H), 7.50 (d, 1 H), 7.31 (d, 1 H), 6.17 (dd, 1 H), 5.93 (s, 1 H), 4.70 (d, 1 H), 4.55-4.67 (m, 1 H), 4.28 (br. s., 2 H), 4.13-4.37 (m, 1 H), 3.91-4.02 (m, 1 H), 3.54-4.01 (m, 2 H), 3.33-3.52 (m, 2 H), 2.54-2.62 (m, 1 H), 2.25-2.36 (m, 1 H), 1.92-2.12 (m, 4 H), 1.49-1.76 (m, 4 H), 1.39 (s, 3 H), 0.91-1.13 (m, 2 H), 0.81 (s, 3 H) |
| 16 | 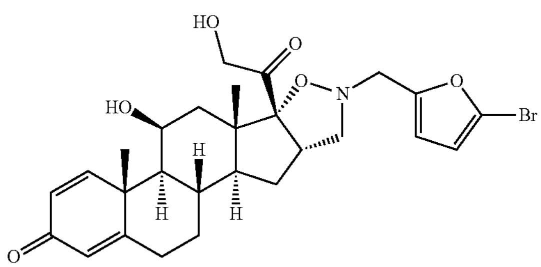 | 30% | LC-MS (ESI POS):<br>$^1$H NMR (300 MHz, DMSO-d6) ppm 7.30 (d, 1 H), 6.48 (d, 1 H), 6.37 (d, 1 H), 6.16 (dd, 1 H), 5.93 (s, 1 H), 4.70 (br. s., 1 H), 4.15-4.35 (m, 1 H), 4.28 (d, 1 H), 3.99 (d, 1 H), 3.96 (d, 1 H), 3.79 (d, 1 H), 3.15-3.41 (m, 2 H), 2.38-2.50 (m, 1 H), 2.21-2.38 (m, 1 H), 1.77-2.19 (m, 3 H), 1.67 (d, 2 H), 1.43-1.60 (m, 2 H), 1.38 (s, 3 H), 1.29-1.43 (m, 1 H), 0.98-1.11 (m, 1 H), 0.95 (dd, 1 H), 0.80 (s, 3 H) |

TABLE 2-continued

| Compound | Structure | Yield | Analytical |
|---|---|---|---|
| 17 | 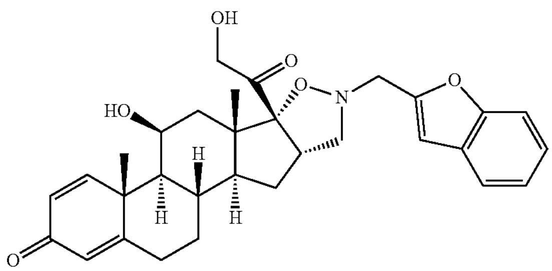 | 30% | LC-MS (ESI POS): 518.03 (MH+)<br>$^1$H NMR (300 MHz, DMSO-d6) ppm 7.51-7.60 (m, 1 H), 7.39-7.51 (m, 1 H), 7.28 (d, 1 H), 7.02-7.25 (m, 2 H), 6.78 (s, 1 H), 6.18 (dd, 1 H), 5.90 (s, 1 H), 4.66 (br. s., 1 H), 4.33 (d, 1 H), 4.20-4.27 (m, 1 H), 4.16 (d, 1 H), 3.43-3.61 (m, 1 H), 3.23-3.42 (m, 1 H), 2.39-2.50 (m, 4 H), 1.81-2.39 (m, 3 H), 1.37-1.79 (m, 5 H), 1.35 (s, 3 H), 0.78 (s, 3 H), 0.56-1.02 (m, 2 H) |
| 18 | 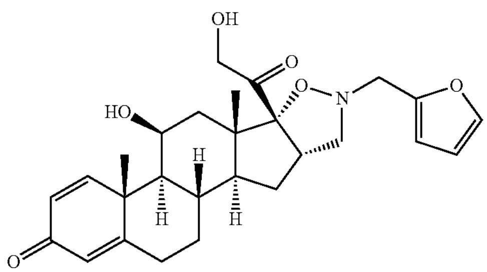 | 60% | LC-MS (ESI POS): 468.12 (MH+)<br>$^1$H NMR (300 MHz, CHLOROFORM-d) ppm 7.36 (dd, 1 H), 7.25 (d, 1 H), 6.34 (dd, 1 H), 6.30 (dd, 1 H), 6.24 (d, 1 H), 6.05 (t, 1 H), 4.46-4.63 (m, 1 H), 4.42 (dd, 1 H), 4.11 (dd, 1 H), 3.90 (s, 2 H), 3.20-3.73 (m, 2 H), 2.88 (t, 1 H), 2.48-2.69 (m, 1 H), 2.36 (ddd, 1 H), 1.87-2.30 (m, 5 H), 1.64-1.84 (m, 2 H), 1.50-1.64 (m, 2 H), 1.47 (s, 3 H), 1.14 (dd, 1 H), 0.96 (s, 3 H) |
| 19 | 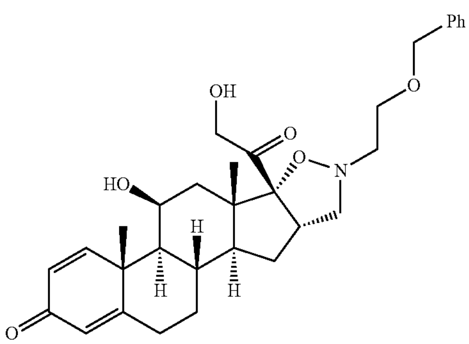 | 50% | LC-MS (ESI POS): 522.19 (MH+)<br>$^1$H NMR (300 MHz, CHLOROFORM-d) ppm 7.29-7.45 (m, 5 H), 6.34 (dd, 1 H), 6.09 (t, 1 H), 4.67 (d, 1 H), 4.55 (d, 1 H), 4.50 (d, 1 H), 4.48 (q, 1 H), 4.21 (d, 1 H), 3.29-3.89 (m, 3 H), 2.82-3.21 (m, 2 H), 2.03-2.77 (m, 7 H), 1.98 (dd, 1 H), 1.47 (s, 3 H), 1.37-1.84 (m, 4 H), 1.14 (dd, 2 H), 0.97 (s, 3 H) |
| 20 | 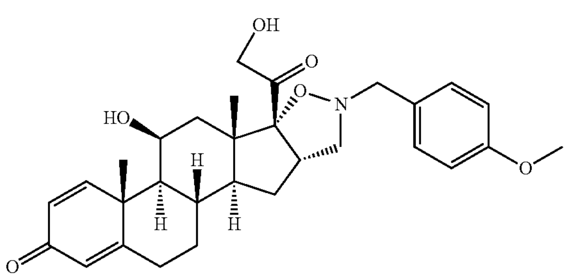 | 40% | LC-MS (ESI POS): 508.19 (MH+)<br>$^1$H NMR (300 MHz, DMSO-d6) ppm 7.31 (d, 1 H) 7.18 (m, 2 H) 6.84 (m, 2 H) 6.17 (dd, 1 H) 5.87-5.96 (m, 1 H) 4.69 (d, 1 H) 4.54-4.66 (m, 1 H) 4.23-4.34 (m, 1 H) 4.05-4.23 (m, 1 H) 3.65-3.95 (m, 6 H) 3.31-3.50 (m, 1 H) 2.54-2.67 (m, 2 H) 2.29-2.41 (m, 1 H) 1.99 (s, 3 H) 1.42-1.74 (m, 5 H) 1.38 (s, 3 H) 0.88-1.12 (m, 2 H) 0.79 (s, 3 H) |
| 21 | 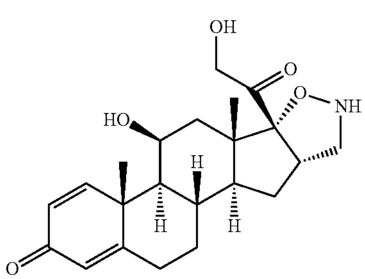 | 50% | LC-MS (ESI POS): 388.12 (MH+)<br>$^1$H NMR (300 MHz, DMSO-d6) ppm 7.31 (d, 1 H), 6.16 (dd, 1 H), 5.93 (s, 1 H), 4.48 (d, 1 H), 4.22-4.39 (m, 1 H), 4.10 (d, 1 H), 3.25-3.62 (m, 2 H), 2.68-2.90 (m, 1 H), 2.54-2.67 (m, 1 H), 2.23-2.42 (m, 1 H), 1.90-2.21 (m, 2 H), 1.41-1.90 (m, 4 H), 1.38 (s, 3 H), 0.96-1.22 (m, 2 H), 0.92 (dd, 1 H), 0.87 (s, 3 H) |

TABLE 2-continued

| Compound | Structure | Yield | Analytical |
|---|---|---|---|
| 22 | 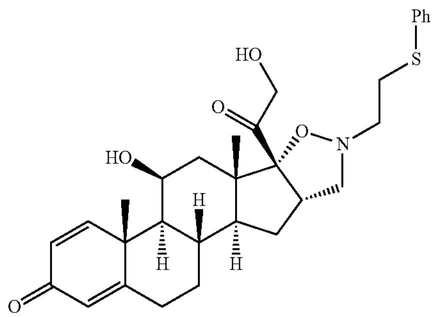 | 23% | LC-MS (ESI POS): 524.07 (MH+)<br>$^1$H NMR (300 MHz, CHLOROFORM-d) ppm 7.25-7.40 (m, 5 H), 7.08-7.24 (m, 1 H), 6.35 (dd, 1 H), 6.09 (t, 1 H), 4.73 (d, 1 H), 4.41-4.57 (m, 1 H), 4.25 (d, 1 H), 3.33-3.78 (m, 2 H), 3.07-3.23 (m, 2 H), 2.95-3.05 (m, 2 H), 2.51-2.71 (m, 1 H), 2.33-2.44 (m, 1 H), 2.03-2.32 (m, 3 H), 1.99 (dd, 1 H), 1.68-1.83 (m, 2 H), 1.64 (dd, 1 H), 1.47 (s, 3 H), 1.44-1.57 (m, 1 H), 1.10-1.25 (m, 1 H), 1.15 (dd, 1 H), 0.97 (s, 3 H) |
| 23 | 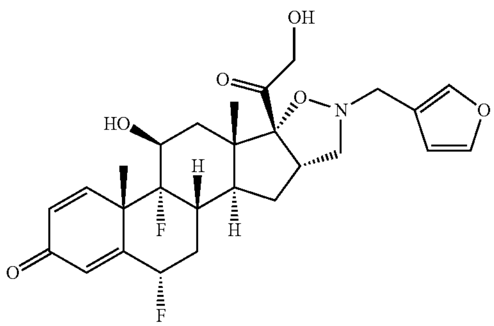 | 47% | LC-MS (ESI POS): 504.07 (MH+)<br>$^1$H NMR (300 MHz, DMSO-d6) ppm 7.59 (t, 1 H), 7.55 (s, 1 H), 7.26 (dd, 1 H), 6.40 (dd, 1 H), 6.30 (dd, 1 H), 6.12 (s, 1 H), 5.63 (dddd, 1 H), 5.44 (d, 1 H), 4.70 (br. s., 1 H), 4.32 (dd, 1 H), 4.10-4.23 (m, 1 H), 4.01 (dd, 1 H), 3.76 (d, 1 H), 3.65 (d, 1 H), 3.30-3.55 (m, 2 H), 2.56-2.75 (m, 1 H), 2.02-2.29 (m, 3 H), 1.91-2.00 (m, 1 H), 1.50-1.78 (m, 3 H), 1.49 (s, 3 H), 1.42 (dd, 1 H), 0.81 (s, 3 H) |
| 24 | 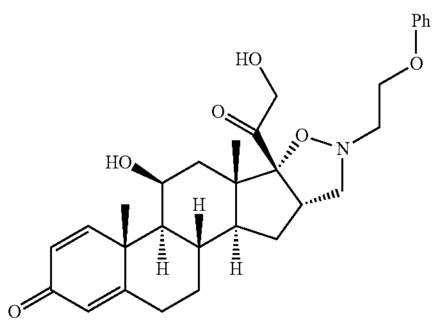 | 31% | LC-MS (ESI POS): 508.18 (MH+)<br>$^1$H NMR (300 MHz, DMSO-d6) ppm 7.38-7.52 (m, 1 H), 7.17-7.37 (m, 3 H), 6.73-7.07 (m, 3 H), 6.16 (dd, 1 H), 5.92 (s, 1 H), 4.45 (d, 1 H), 4.21-4.33 (m, 1 H), 3.98-4.20 (m, 3 H), 3.26-3.41 (m, 2 H), 3.06-3.21 (m, 1 H), 2.85-3.04 (m, 1 H), 2.55-2.63 (m, 1 H), 2.20-2.38 (m, 1 H), 1.85-2.20 (m, 2 H), 1.41-1.77 (m, 5 H), 1.38 (s, 3 H), 0.99-1.14 (m, 1 H), 0.93 (dd, 1 H), 0.82 (s, 3 H) |
| 25 | 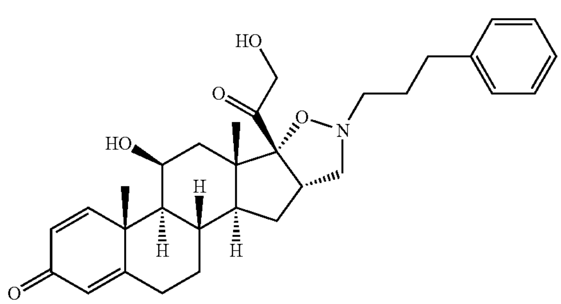 | 24% | LC-MS (ESI POS): 506.09 (MH+)<br>$^1$H NMR (300 MHz, DMSO-d6) ppm 7.12-7.33 (m, 6 H), 6.16 (dd, 1 H), 5.92 (s, 1 H), 4.69 (s, 1 H), 4.49 (d, 1 H), 4.21-4.35 (m, 1 H), 4.10 (d, 1 H), 3.42-3.53 (m, 1 H), 3.21-3.42 (m, 1 H), 2.54-2.71 (m, 5 H), 2.26-2.39 (m, 1 H), 1.84-2.14 (m, 3 H), 1.48-1.80 (m, 6 H), 1.38 (s, 3 H), 1.35-1.45 (m, 1 H), 0.98-1.13 (m, 1 H), 0.94 (dd, 1 H), 0.82 (s, 3 H) |
| 26 | 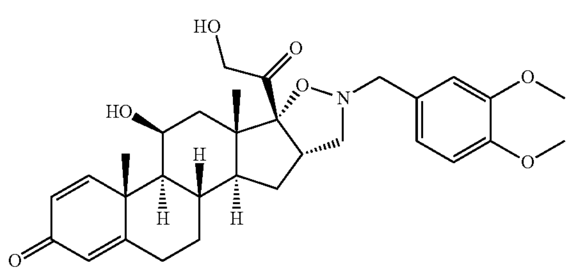 | 49% | LC-MS (ESI POS): 538.21 (MH+)<br>$^1$H NMR (300 MHz, DMSO-d$_6$) ppm 7.31 (d, 1 H), 6.82-6.90 (m, 2 H), 6.78 (dd, 1 H), 6.17 (dd, 1 H), 5.93 (s, 1 H), 4.27 (d, 1 H), 4.21 (d, 1 H), 3.89 (d, 1 H), 3.85 (d, 1 H), 3.72 (s, 3 H), 3.70 (s, 3 H), 3.64-3.71 (m, 1 H), 3.29-3.54 (m, 2 H), 2.52-2.67 (m, 1 H), 2.22-2.40 (m, 1 H), 1.91-2.20 (m, 3 H), 1.50-1.81 (m, 4 H), 1.29-1.50 (m, 4 H), 0.99-1.13 (m, 1 H), 0.95 (dd, 1 H), 0.80 (s, 3 H) |

TABLE 2-continued

| Compound | Structure | Yield | Analytical |
|---|---|---|---|
| 27 | 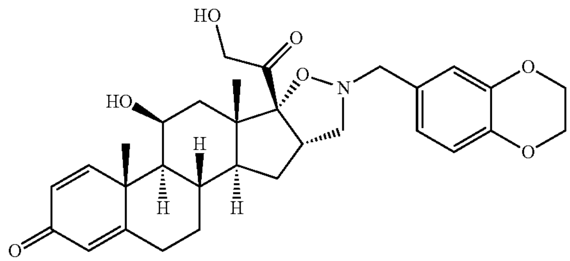 | 16% | LC-MS (ESI POS): 536.19 (MH+)<br>$^1$H NMR (300 MHz, CHLOROFORM-d) ppm 7.34 (d, 1 H), 6.82 (d, 1 H), 6.82 (d, 1 H), 6.74 (dd, 1 H), 6.39 (dd, 1 H), 6.13 (t, 1 H), 4.41-4.66 (m, 2 H), 4.13-4.33 (m, 4 H), 4.11 (d, 1 H), 3.96 (d, 1 H), 3.89 (d, 1 H), 3.61 (br. s., 2 H), 2.48-2.73 (m, 1 H), 2.32-2.48 (m, 1 H), 1.90-2.28 (m, 3 H), 1.73 (br. s., 1 H), 1.64 (dd, 2 H), 1.47 (s, 2 H), 1.33-1.58 (m, 3 H), 1.02-1.21 (m, 2 H), 0.95 (s, 3 H) |
| 28 | 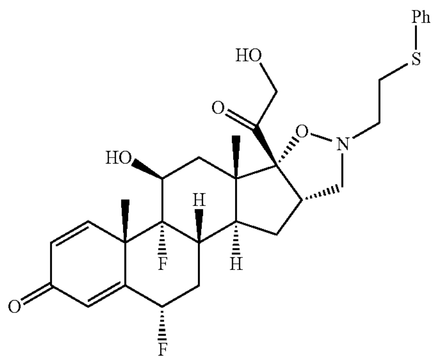 | 18% | LC-MS (ESI POS): 560.07 (MH+)<br>$^1$H NMR (300 MHz, DMSO-d6) ppm 7.12-7.35 (m, 6 H), 6.30 (dd, 1 H), 6.11 (s, 1 H), 5.49-5.76 (m, 1 H), 5.45 (d, 1 H), 4.55 (d, 1 H), 4.13-4.19 (m, 1 H), 4.16 (d, 1 H), 3.42-3.56 (m, 2 H), 3.06-3.20 (m, 2 H), 2.78-3.05 (m, 2 H), 2.55-2.68 (m, 1 H), 1.83-2.32 (m, 3 H), 1.51-1.70 (m, 3 H), 1.49 (s, 3 H), 1.41 (dd, 1 H), 0.82 (s, 3 H) |
| 29 | 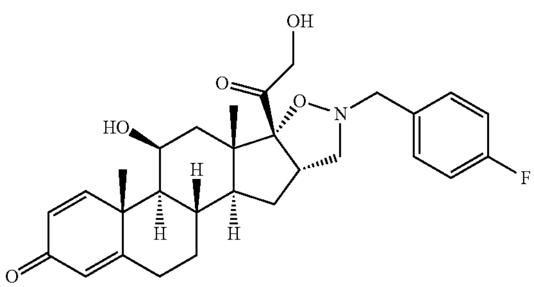 | 12% | LC-MS (ESI POS): 496.28 (MH+)<br>$^1$H NMR (300 MHz, CHLOROFORM-d) ppm 7.16-7.28 (m, 3 H), 6.95-7.10 (m, 2 H), 6.31 (dd, 1 H), 6.06 (t, 1 H), 4.50 (q, 1 H), 4.26 (d, 1 H), 3.99 (d, 1 H), 3.78-3.97 (m, 2 H), 3.38-3.71 (m, 2 H), 2.51-2.68 (m, 1 H), 2.37 (m, 1 H), 2.03-2.30 (m, 3 H), 1.95 (dd, 1 H), 1.50-1.82 (m, 5 H), 1.47 (s, 3 H), 1.09-1.34 (m, 1 H), 0.95 (s, 3 H) |
| 30 | 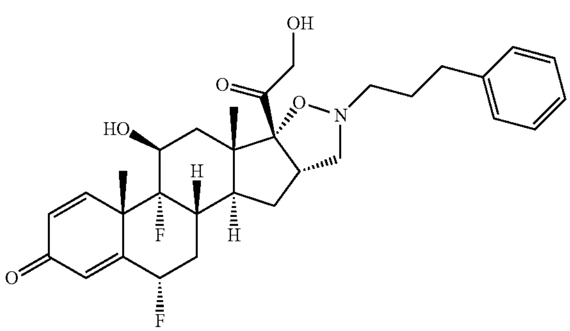 | 60% | LC-MS (ESI POS): 546.31 (MH+)<br>$^1$H NMR (300 MHz, DMSO-d6) ppm 7.10-7.34 (m, 6 H), 6.29 (dd, 1 H), 6.11 (s, 1 H), 5.63 (dddd, 1 H), 5.44 (d, 1 H), 4.81 (t, 1 H), 4.51 (dd, 1 H), 4.14-4.22 (m, 1 H), 4.13 (dd, 1 H), 3.32-3.61 (m, 2 H), 2.54-2.71 (m, 4 H), 2.18-2.34 (m, 1 H), 2.03-2.18 (m, 1 H), 1.86-2.03 (m, 2 H), 1.69-1.86 (m, 2 H), 1.52-1.69 (m, 3 H), 1.49 (s, 3 H), 1.32-1.46 (m, 2 H), 0.82 (s, 3 H) |
| 31 | 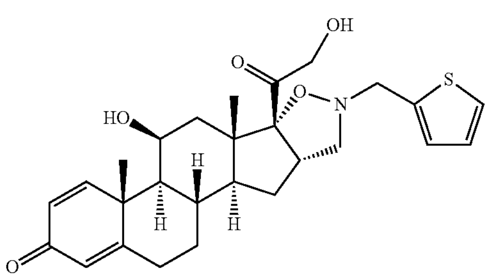 | 60% | LC-MS (ESI POS): 484.13 (MH+)<br>1H NMR (300 MHz, CHLOROFORM-d) ppm 7.18-7.28 (m, 2 H), 6.90-7.03 (m, 2 H), 6.31 (dd, 1 H), 6.05 (s, 1 H), 4.54 (d, 1 H), 4.46-4.55 (m, 1 H), 4.09-4.27 (m, 2 H), 4.11 (d, 1 H), 3.39-3.69 (m, 2 H), 2.59 (m, 1 H), 2.36 (ddd, 1 H), 2.19 (br. s., 1 H), 1.96-2.15 (m, 2 H), 1.56-1.76 (m, 3 H), 1.47 (s, 3 H), 1.02-1.34 (m, 4 H), 0.96 (s, 3 H) |

TABLE 2-continued

| Compound | Structure | Yield | Analytical |
|---|---|---|---|
| 32 | 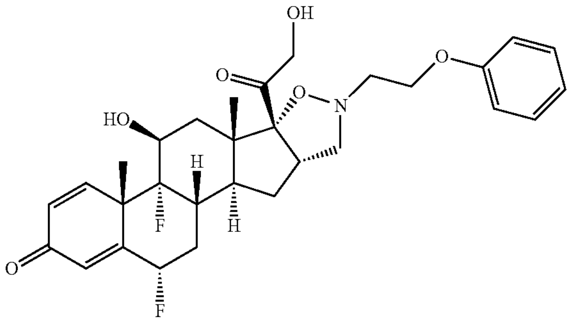 | 52% | LC-MS (ESI POS): 544.22 (MH+)<br>$[a]_D^{25} = +152.9°$ (c = 0.30, CHCl$_3$)<br>$^1$H NMR (300 MHz, DMSO-d6) ppm 7.12-7.41 (m, 3 H), 6.80-7.04 (m, 3 H), 6.29 (dd, 1 H), 6.11 (s, 1 H), 5.51-5.86 (m, 1 H), 5.28-5.49 (m, 1 H), 4.72 (t, 1 H), 4.47 (dd, 1 H), 3.94-4.27 (m, 4 H), 3.55 (br. s., 1 H), 3.34-3.46 (m, 1 H), 3.06-3.22 (m, 1 H), 2.97 (dt, 1 H), 2.60-2.71 (m, 1 H), 2.04-2.34 (m, 3 H), 1.81-2.04 (m, 1 H), 1.52-1.69 (m, 3 H), 1.49 (s, 3 H), 1.37-1.47 (m, 1 H), 0.83 (s, 3 H) |
| 33 | 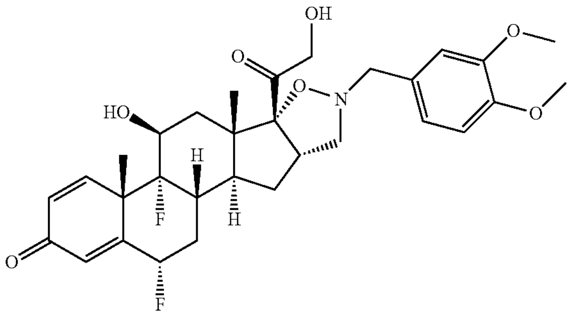 | 87% | LC-MS (ESI POS): 574.21 (MH+)<br>$[a]_D^{25} = +167.9°$ (c = 0.30, CHCl$_3$)<br>$^1$H NMR (300 MHz, DMSO-d6) ppm 7.26 (dd, 1 H), 6.86 (d, 1 H), 6.86 (d, 1 H), 6.77 (dd, 1 H), 6.30 (dd, 1 H), 6.13 (s, 1 H), 5.49-5.79 (m, 1 H), 5.43 (dd, 1 H), 4.68 (br. s., 1 H), 4.06-4.35 (m, 2 H), 3.92 (dd, 1 H), 3.83 (d, 1 H), 3.73 (s, 3 H), 3.71 (s, 3 H), 3.69 (d, 1 H), 3.33-3.57 (m, 2 H), 2.55-2.70 (m, 1 H), 2.05-2.36 (m, 3 H), 1.85-1.99 (m, 1 H), 1.52-1.70 (m, 3 H), 1.49 (s, 3 H), 1.37-1.47 (m, 1 H), 0.81 (s, 3 H) |
| 34 | 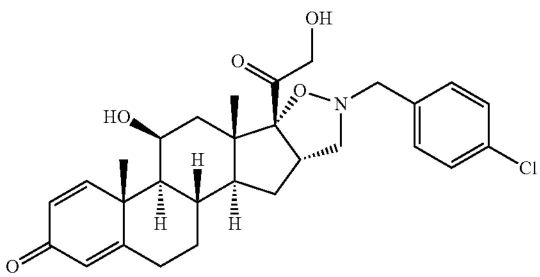 | 52% | LC-MS (ESI POS): 512.17 (MH+)<br>$[a]_D^{25} = +217.5°$ (c = 0.30, CHCl$_3$)<br>1H NMR (300 MHz, DMSO-d6) ppm 7.24-7.42 (m, 5 H), 6.17 (dd, 1 H), 5.93 (s, 1 H), 4.69 (d, 1 H), 4.64 (t, 1 H), 4.21-4.37 (m, 1 H), 3.98-4.20 (m, 1 H), 3.90 (d, 1 H), 3.86 (dd, 1 H), 3.73 (d, 1 H), 3.31-3.59 (m, 2 H), 2.53-2.61 (m, 1 H), 2.22-2.40 (m, 1 H), 1.89-2.22 (m, 3 H), 1.49-1.70 (m, 4 H), 1.41-1.48 (m, 1 H), 1.38 (s, 3 H), 1.01-1.11 (m, 1 H), 0.95 (dd, 1 H), 0.80 (s, 3 H) |
| 35 | 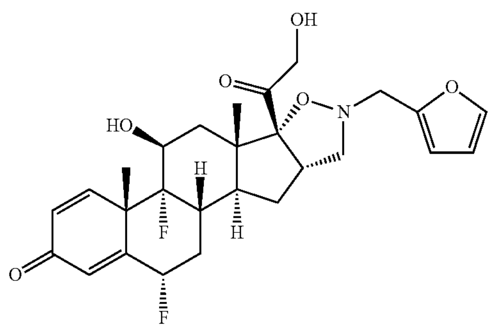 | 59% | LC-MS (ESI POS): 504.02 (MH+)<br>$[a]_D^{25} = +133.1°$ (c = 0.30, CHCl$_3$)<br>$^1$H NMR (300 MHz, DMSO-d6) ppm 7.55 (dd, 1 H), 7.26 (dd, 1 H), 6.40 (dd, 1 H), 6.22-6.35 (m, 2 H), 6.12 (s, 1 H), 5.49-5.78 (m, 1 H), 5.43 (d, 1 H), 4.71 (s br, 1 H), 4.27 (d, 1 H), 3.99 (d, 1 H), 3.92 (d, 1 H), 3.82 (d, 1 H), 3.35-3.54 (m, 3 H), 2.55-2.71 (m, 1 H), 2.01-2.31 (m, 3 H), 1.84-1.98 (m, 1 H), 1.51-1.68 (m, 3 H), 1.49 (s, 3 H), 1.42 (dd, 1 H), 0.81 (s, 3 H) |
| 36 | 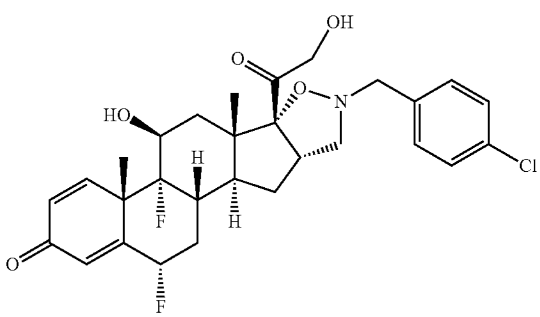 | 84% | LC-MS (ESI POS): 547.99 (MH+)<br>$^1$H NMR (300 MHz, DMSO-d$_6$) ppm 7.20-7.43 (m, 5 H), 6.30 (dd, 1 H), 6.12 (s, 1 H), 5.50-5.81 (m, 1 H), 5.43 (dd, 1 H), 4.54-4.78 (m, 1 H), 4.00-4.23 (m, 2 H), 3.81-3.97 (m, 2 H), 3.74 (d, 1 H), 3.33-3.59 (m, 2 H), 2.55-2.63 (m, 1 H), 2.01-2.35 (m, 3 H), 1.77-1.96 (m, 1 H), 1.51-1.69 (m, 3 H), 1.49 (s, 3 H), 1.35-1.46 (m, 1 H), 0.80 (s, 3 H) |

TABLE 2-continued

| Compound | Structure | Yield | Analytical |
|---|---|---|---|
| 37 | 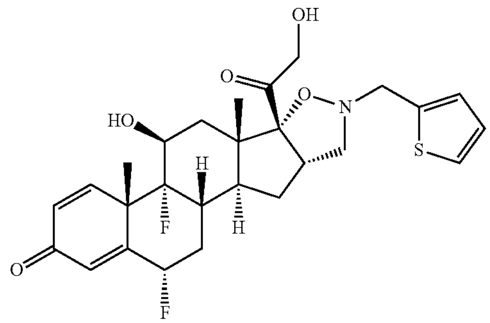 | 43% | LC-MS (ESI POS): 519.98 (MH+)<br>$[a]_D^{25}$ = +129.9° (c = 0.63, CHCl$_3$)<br>$^1$H NMR (300 MHz, DMSO-d$_6$) ppm 7.40-7.47 (m, 1 H), 7.26 (dd, 1 H), 6.83-7.03 (m, 2 H), 6.30 (dd, 1 H), 6.12 (s, 1 H), 5.49-5.80 (m, 1 H), 5.45 (dd, 1 H), 4.72 (br. s., 1 H), 4.33 (dd, 1 H), 4.09-4.24 (m, 2 H), 3.88-4.07 (m, 2 H), 3.43-3.60 (m, 1 H), 3.34-3.43 (m, 1 H), 2.55-2.70 (m, 1 H), 2.04-2.39 (m, 3 H), 1.90-2.03 (m, 1 H), 1.51-1.71 (m, 3 H), 1.49 (s, 3 H), 1.37-1.47 (m, 1 H), 0.81 (s, 3 H) |
| 38 | 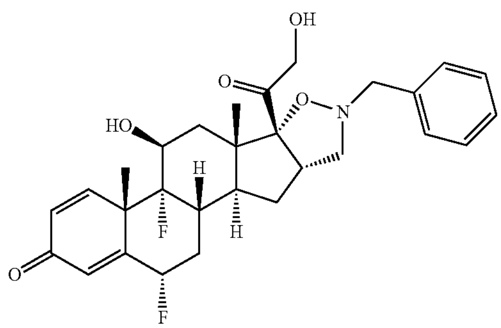 | 21% | LC-MS (ESI POS): 514.25 (MH+)<br>$[a]_D^{25}$ = +146.1° (c = 0.28, CHCl$_3$)<br>$^1$H NMR (300 MHz, DMSO-d$_6$) ppm 7.12-7.44 (m, 6 H), 6.30 (dd, 1 H), 6.13 (s, 1 H), 5.48-5.85 (m, 1 H), 5.43 (dd, 1 H), 4.46-4.78 (m, 1 H), 4.04-4.29 (m, 2 H), 3.84-3.96 (m, 2 H), 3.78 (d, 1 H), 3.44-3.55 (m, 1 H), 3.33-3.44 (m, 1 H), 2.56-2.69 (m, 1 H), 2.02-2.39 (m, 3 H), 1.80-1.96 (m, 1 H), 1.52-1.69 (m, 3 H), 1.49 (s, 3 H), 1.36-1.47 (m, 1 H), 0.80 (s, 3 H) |
| 39 | 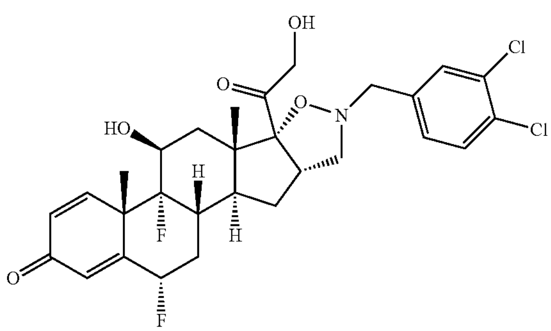 | 65% | LC-MS (ESI POS): 581.91 (MH+)<br>$[a]_D^{25}$ = +188.3° (c = 0.53, CHCl$_3$)<br>$^1$H NMR (300 MHz, DMSO-d$_6$) ppm 7.57 (d, J = 8.22 Hz, 1 H), 7.53 (d, J = 2.05 Hz, 1 H), 7.27 (dd, J = 8.22, 1.76 Hz, 1 H), 7.25 (dd, J = 9.98, 1.17 Hz, 1 H), 6.30 (dd, J = 10.12, 1.91 Hz, 1 H), 6.12 (s, 1 H), 5.48-5.80 (m, 1 H), 5.44 (dd, J = 4.25, 1.32 Hz, 1 H), 4.73 (t, J = 4.84 Hz, 1 H), 4.01-4.28 (m, 2 H), 3.86-4.03 (m, 2 H), 3.76 (d, J = 14.09 Hz, 1 H), 3.46-3.60 (m, 1 H), 3.35-3.45 (m, 1 H), 2.55-2.69 (m, 1 H), 2.06-2.37 (m, 3 H), 1.79-1.96 (m, 1 H), 1.52-1.71 (m, 3 H), 1.49 (s, 3 H), 1.39-1.47 (m, 1 H), 0.80 (s, 3 H) |
| 40 | 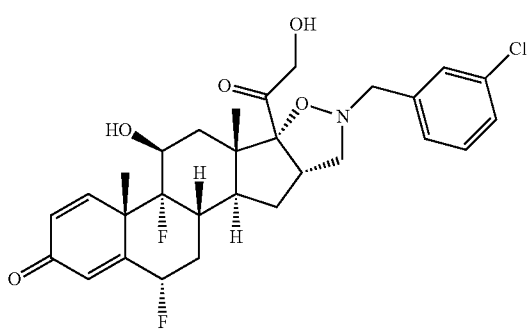 | 61% | LC-MS (ESI POS): 548.19 (MH+)<br>$[a]_D^{25}$ = +176.9° (c = 0.55, CHCl$_3$)<br>$^1$H NMR (300 MHz, DMSO-d$_6$) ppm 7.14-7.41 (m, 5 H), 6.30 (dd, 1 H), 6.13 (s, 1 H), 5.50-5.81 (m, 1 H), 5.44 (dd, 1 H), 4.48-4.82 (m, 1 H), 4.03-4.29 (m, 2 H), 3.85-4.01 (m, 2 H), 3.78 (d, 1 H), 3.45-3.57 (m, 1 H), 3.35-3.42 (m, 1 H), 2.57-2.71 (m, 1 H), 2.03-2.40 (m, 3 H), 1.80-1.96 (m, 1 H), 1.53-1.73 (m, 3 H), 1.49 (s, 3 H), 1.39-1.47 (m, 1 H), 0.80 (s, 3 H) |

TABLE 2-continued

| Compound | Structure | Yield | Analytical |
|---|---|---|---|
| 41 | 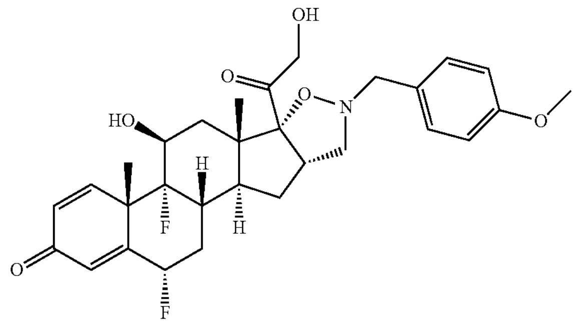 | 71% | LC-MS (ESI POS): 544.00 (MH+)<br>$[a]_D^{25} = +175.8$ (c = 0.50, CHCl$_3$)<br>$^1$H NMR (300 MHz, DMSO-d$_6$) ppm 7.26 (d, 1 H), 7.18 (m, 2 H), 6.85 (m, 2 H), 6.30 (dd, 1 H), 6.13 (s, 1 H), 5.47-5.84 (m, 1 H), 5.43 (d, 1 H), 4.54-4.80 (m, 1 H), 4.07-4.28 (m, 2 H), 3.92 (dd, 1 H), 3.81 (d, 1 H), 3.73 (s, 3 H), 3.72 (d, 1 H), 3.33-3.53 (m, 2 H), 2.56-2.70 (m, 1 H), 1.99-2.35 (m, 3 H), 1.84-1.96 (m, 1 H), 1.51-1.67 (m, 3 H), 1.49 (s, 3 H), 1.32-1.47 (m, 1 H), 0.80 (s, 3 H) |
| 42 | 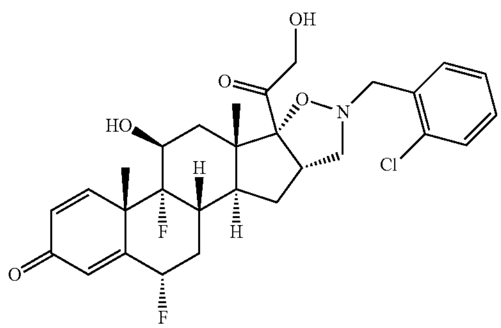 | 59% | LC-MS (ESI POS): 547.99 (MH+)<br>$[a]_D^{25} = +139.0$ (c = 0.58, CHCl$_3$)<br>$^1$H NMR (300 MHz, DMSO-d$_6$) d ppm 7.09-7.62 (m, 5 H), 6.30 (dd, 1 H), 6.13 (s, 1 H), 5.49-5.83 (m, 1 H), 5.43 (dd, 1 H), 4.69 (t, 1 H), 4.00-4.24 (m, 2 H), 3.95-4.00 (m, 2 H), 3.89 (dd, 1 H), 3.45-3.58 (m, 1 H), 3.35-3.45 (m, 1 H), 2.57-2.69 (m, 1 H), 2.11-2.36 (m, 3 H), 1.85-2.02 (m, 1 H), 1.52-1.68 (m, 3 H), 1.49 (s, 3 H), 1.40-1.47 (m, 1 H), 0.80 (s, 3 H) |
| 43 | 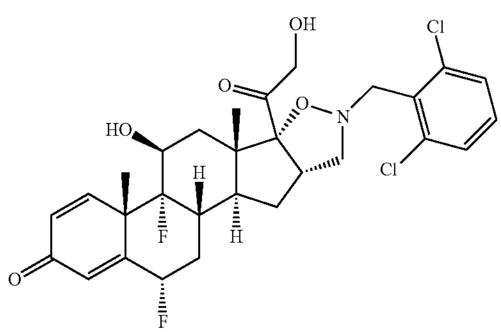 | 60% | LC-MS (ESI POS): 581.99 (MH+)<br>$[a]_D^{25} = +168.4$ (c = 0.57, CHCl$_3$)<br>$^1$H NMR (300 MHz, DMSO-d$_6$) ppm 7.42-7.53 (m, 2 H), 7.35 (dd, 1 H), 7.26 (d, 1 H), 6.30 (dd, 1 H), 6.12 (s, 1 H), 5.50-5.80 (m, 1 H), 5.42 (dd, 1 H), 4.60 (t, 1 H), 4.03-4.25 (m, 3 H), 3.77-3.89 (m, 2 H), 3.47-3.64 (m, 1 H), 3.32-3.40 (m, 1 H), 2.56-2.71 (m, 1 H), 2.11-2.37 (m, 3 H), 1.89-2.08 (m, 1 H), 1.52-1.67 (m, 3 H), 1.48 (s, 3 H), 1.41-1.46 (m, 1 H), 0.79 (s, 3 H) |
| 44 | 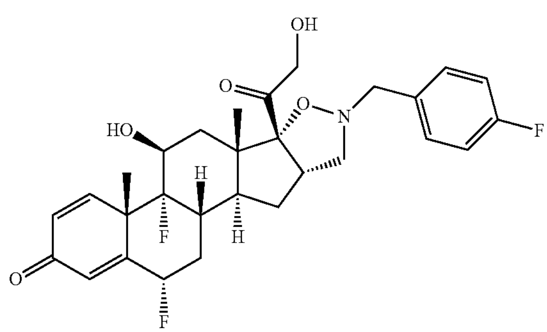 | 88% | LC-MS (ESI POS): 532.03 (MH+)<br>$[a]_D^{25} = +175.3$ (c = 0.22, CHCl$_3$)<br>$^1$H NMR (300 MHz, DMSO-d$_6$) ppm 7.28-7.37 (m, 2 H), 7.26 (dd, 1 H), 7.01-7.18 (m, 2 H), 6.30 (dd, 1 H), 6.12 (s, 1 H), 5.50-5.78 (m, 1 H), 5.43 (dd, 1 H), 4.57-4.77 (m, 1 H), 3.99-4.26 (m, 2 H), 3.89 (d, 1 H), 3.83-3.95 (m, 1 H), 3.75 (d, 1 H), 3.43-3.60 (m, 1 H), 3.34-3.43 (m, 1 H), 2.57-2.69 (m, 1 H), 2.04-2.36 (m, 3 H), 1.78-1.99 (m, 1 H), 1.52-1.72 (m, 3 H), 1.49 (s, 3 H), 1.38-1.48 (m, 1 H), 0.80 (s, 3 H) |

TABLE 2-continued

| Compound | Structure | Yield | Analytical |
|---|---|---|---|
| 45 | 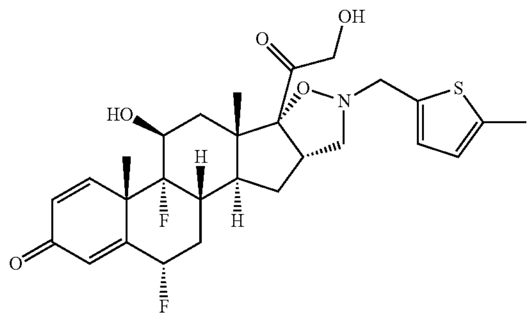 | 98% | LC-MS (ESI POS): 534.16 (MH+)<br>$[a]_D^{25}$ = +141.6 (c = 0.2 CHCl$_3$)<br>$^1$H NMR (300 MHz, DMSO-d$_6$) ppm 7.26 (dd, 1 H), 6.73 (d, 1 H), 6.62 (dd, 1 H), 6.30 (dd, 1 H), 6.11 (s, 1 H), 5.51-5.78 (m, 1 H), 5.42-5.50 (m, 1 H), 4.60-4.83 (m, 1 H), 4.28-4.45 (m, 1 H), 4.11-4.22 (m, 1 H), 3.96-4.12 (m, 2 H), 3.89 (d, 1 H), 3.36-3.53 (m, 2 H), 2.54-2.60 (m, 1 H), 2.37 (s, 3 H), 1.91-2.22 (m, 4 H), 1.51-1.65 (m, 3 H), 1.48 (s, 3 H), 1.34-1.45 (m, 1 H), 0.80 (s, 3 H) |
| 46 | 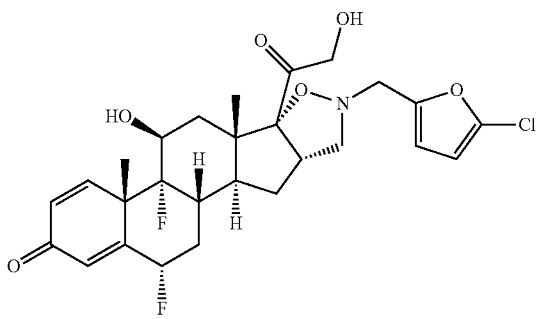 | 75% | LC-MS (ESI POS): 538.13 (MH+)<br>$[a]_D^{25}$ = +129.2 (c = 0.2 CHCl$_3$)<br>$^1$H NMR (300 MHz, DMSO-d$_6$) ppm 7.26 (dd, 1 H), 6.36-6.47 (m, 2 H), 6.30 (dd, 1 H), 6.07-6.17 (m, 1 H), 5.51-5.80 (m, 1 H), 5.47 (dd, 1 H), 4.63-4.87 (m, 1 H), 4.21-4.32 (m, 1 H), 4.11-4.20 (m, 1 H), 4.00 (dd, 1 H), 3.92 (d, 1 H), 3.78 (d, 1 H), 3.42-3.57 (m, 1 H), 3.35-3.42 (m, 1 H), 2.57-2.63 (m, 1 H), 2.02-2.26 (m, 3 H), 1.79-1.98 (m, 1 H), 1.52-1.70 (m, 3 H), 1.48 (s, 3 H), 1.38-1.47 (m, 1 H), 0.80 (s, 3 H) |
| 47 | 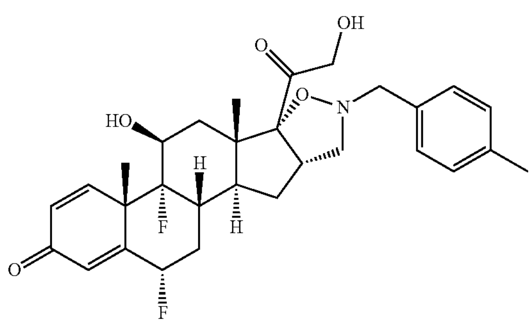 | 58% | LC-MS (ESI POS): 528.11 (MH+)<br>$[a]_D^{25}$ = +163.1° (c = 0.50, CHCl$_3$)<br>$^1$H NMR (300 MHz, DMSO-d$_6$) ppm 7.26 (dd, 1 H), 7.02-7.20 (m, 4 H), 6.30 (dd, 1 H), 6.13 (s, 1 H), 5.51-5.74 (m, 1 H), 5.44 (dd, 1 H), 4.67 (br. s., 1 H), 4.10-4.27 (m, 2 H), 3.91 (dd, 1 H), 3.83 (d, 1 H), 3.74 (d, 1 H), 3.42-3.56 (m, 1 H), 3.34-3.43 (m, 1 H), 2.54-2.68 (m, 1 H), 2.28 (s, 3 H), 2.02-2.25 (m, 3 H), 1.82-1.97 (m, 1 H), 1.51-1.69 (m, 3 H), 1.49 (s, 3 H), 1.35-1.48 (m, 1 H), 0.80 (s, 3 H) |
| 48 | 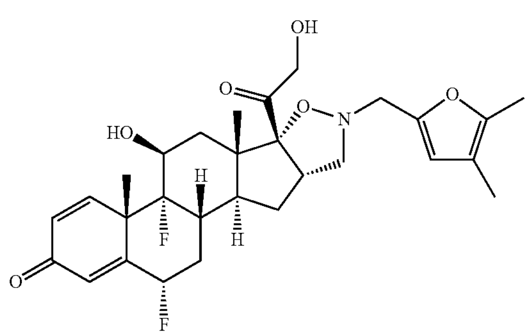 | 48% | LC-MS (ESI POS): 532.03 MH+<br>$[a]_D^{25}$ = +124.7 (c = 0.2, CHCl$_3$)<br>$^1$H NMR (300 MHz, DMSO-d$_6$) ppm 7.26 (dd, 1 H), 6.30 (dd, 1 H), 6.12 (s, 1 H), 6.04 (s, 1 H), 5.48-5.74 (m, 1 H), 5.44 (dd, 1 H), 4.73 (t, 1 H), 4.38 (dd, 1 H), 4.10-4.23 (m, 1 H), 4.03 (dd, 1 H), 3.77 (s, 2 H), 3.34-3.50 (m, 2 H), 2.57-2.68 (m, 1 H), 2.13-2.25 (m, 2 H), 2.11 (s, 3 H), 1.89-2.08 (m, 2 H), 1.84 (s, 3 H), 1.52-1.66 (m, 3 H), 1.49 (s, 3 H), 1.33-1.45 (m, 1 H), 0.81 (s, 3 H) |

TABLE 2-continued

| Compound | Structure | Yield | Analytical |
|---|---|---|---|
| 49 | 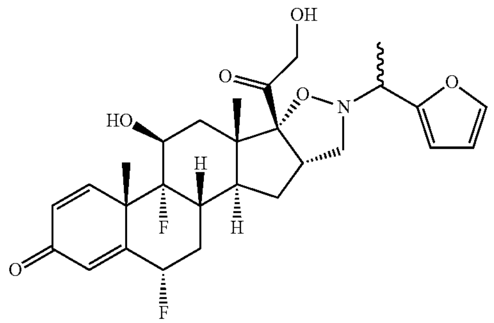 | 44% | LC-MS (ESI POS): 518.07 MH+<br>$[a]_D^{25}$ = +49.55 (c = 0.35, MeOH)<br>$^1$H NMR (300 MHz, DMSO-d$_6$) ppm 7.51 and 7.54 (dd, 1 H), 7.26 (dd, 1 H), 6.20-6.41 (m, 3 H), 6.12 (s, 1 H), 5.49-5.74 (m, 1 H), 5.41 and 5.45 (dd, 1 H), 4.67 and 4.81 (t, 1 H), 4.06-4.28 (m, 2 H), 3.92 and 4.48 (dd, 1 H), 3.76-3.98 (m, 1 H), 3.39-3.52 and 3.00-3.15 (m, 1 H), 3.33-3.41 (m, 1 H), 2.58-2.69 (m, 1 H), 1.83-2.25 (m, 3 H), 1.51-1.71 (m, 3 H), 1.48 and 1.49 (s, 3 H), 1.35-1.42 (m, 2 H), 1.31 and 1.40 (d, 3 H), 0.78 and 0.81 (s, 3 H) |
| 50 | 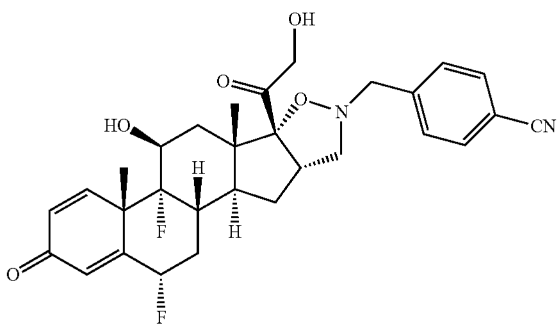 | 37% | LC-MS (ESI POS): 539.12 MH+<br>$^1$H NMR (300 MHz, DMSO-d$_6$) ppm 7.79 (m, 2 H), 7.48 (m, 2 H), 7.25 (dd, 1 H), 6.30 (dd, 1 H), 6.13 (s, 1 H), 5.49-5.82 (m, 1 H), 5.43 (dd, 1 H), 4.55-4.83 (m, 1 H), 4.11-4.21 (m, 1 H), 3.93-4.11 (m, 2 H), 3.74-3.94 (m, 2 H), 3.48-3.65 (m, 1 H), 3.35-3.48 (m, 1 H), 2.57-2.72 (m, 1 H), 2.07-2.35 (m, 3 H), 1.76-1.96 (m, 1 H), 1.51-1.72 (m, 3 H), 1.49 (s, 3 H), 1.38-1.47 (m, 1 H), 0.80 (s, 3 H) |
| 51 | 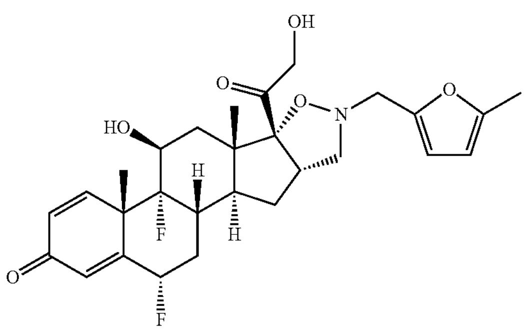 | 78% | LC-MS (ESI POS): 518.13 MH+<br>$^1$H NMR (300 MHz, DMSO-d$_6$) ppm 7.26 (dd, 1 H), 6.30 (dd, 1 H), 6.14 (d, 1 H), 6.09-6.13 (m, 1 H), 5.98 (dq, 1 H), 5.49-5.77 (m, 1 H), 5.44 (dd, 1 H), 4.73 (t, 1 H), 4.34 (dd, 1 H), 4.11-4.22 (m, 1 H), 4.01 (dd, 1 H), 3.83 (d, 1 H), 3.78 (d, 1 H), 3.34-3.52 (m, 2 H), 2.58-2.69 (m, 1 H), 2.22-2.31 (m, 1 H), 2.20 (d, 3 H), 1.99-2.17 (m, 2 H), 1.85-1.98 (m, 1 H), 1.51-1.67 (m, 3 H), 1.49 (s, 3 H), 1.42 (dd, 1 H), 0.81 (s, 3 H) |
| 52 | 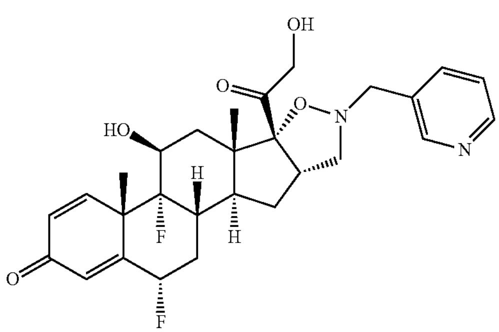 | 73% | LC-MS (ESI POS): 515.33 MH+<br>$[a]_D^{25}$ = +178.7 (c = 0.25, MeOH)<br>$^1$H NMR (300 MHz, DMSO-d$_6$) ppm 8.41-8.54 (m, 2 H), 7.68 (dt, 1 H), 7.35 (ddd, 1 H), 7.26 (dd, 1 H), 6.30 (dd, 1 H), 6.13 (s, 1 H), 5.49-5.84 (m, 1 H), 5.45 (dd, 1 H), 4.68 (br. s., 1 H), 4.11-4.24 (m, 1 H), 3.81-4.07 (m, 3 H), 3.76 (d, 1 H), 3.46-3.62 (m, 1 H), 3.34-3.46 (m, 1 H), 2.56-2.67 (m, 1 H), 2.06-2.26 (m, 3 H), 1.80-1.98 (m, 1 H), 1.53-1.72 (m, 3 H), 1.49 (s, 3 H), 1.37-1.47 (m, 1 H), 0.80 (s, 3 H) |

TABLE 2-continued

| Compound | Structure | Yield | Analytical |
|---|---|---|---|
| 53 | 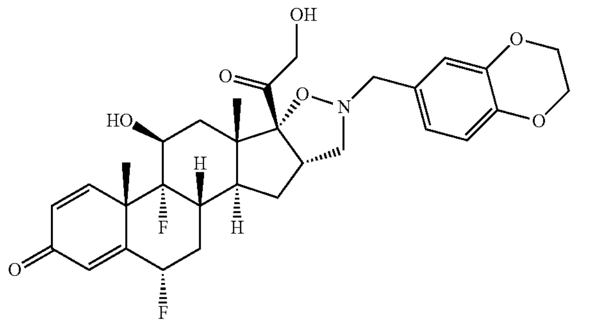 | 64% | LC-MS (ESI POS): 572.08 MH+<br>$[a]_D^{25}$ = +145.2 (c = 0.2, CHCl$_3$)<br>$^1$H NMR (300 MHz, DMSO-d$_6$) ppm 7.26 (dd, 1 H), 6.64-6.83 (m, 3 H), 6.30 (dd, 1 H), 6.12 (s, 1 H), 5.50-5.74 (m, 1 H), 5.44 (d, 1 H), 4.59-4.91 (m, 1 H), 4.11-4.32 (m, 6 H), 3.96 (dd, 1 H), 3.74 (d, 1 H), 3.69 (d, 1 H), 3.33-3.54 (m, 2 H), 2.57-2.70 (m, 1 H), 1.83-2.35 (m, 4 H), 1.51-1.68 (m, 3 H), 1.49 (s, 3 H), 1.42 (dd, 1 H), 0.80 (s, 3 H) |
| 54 | 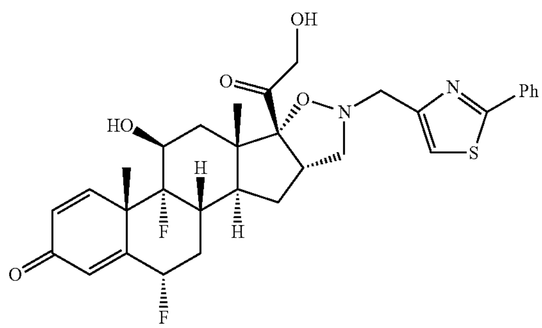 | 54% | LC-MS (ESI POS): 597.07 MH+<br>$[a]_D^{25}$ = +144.2 (c = 0.28, CHCl$_3$)<br>$^1$H NMR (300 MHz, DMSO-d$_6$) ppm 7.83-7.99 (m, 2 H), 7.51 (s, 1 H), 7.43-7.51 (m, 3 H), 7.25 (dd, 1 H), 6.30 (dd, 1 H), 6.12 (s, 1 H), 5.51-5.74 (m, 1 H), 5.43 (dd, 1 H), 4.37 (d, 1 H), 4.13-4.22 (m, 1 H), 4.09 (d, 1 H), 4.00 (d, 1 H), 3.99 (d, 1 H), 3.49-3.64 (m, 1 H), 3.37-3.47 (m, 1 H), 2.56-2.68 (m, 1 H), 2.08-2.34 (m, 3 H), 1.86-1.99 (m, 1 H), 1.51-1.68 (m, 3 H), 1.49 (s, 3 H), 1.39-1.47 (m, 1 H), 0.82 (s, 3 H) |
| 55 | 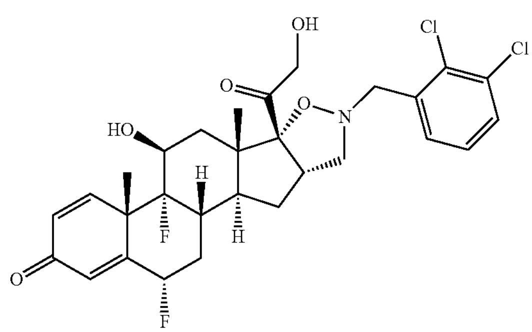 | 23% | LC-MS (ESI POS): 582.2 MH+<br>$[a]_D^{25}$ = +146 (c = 0.2, CHCl$_3$)<br>$^1$H NMR (300 MHz, DMSO-d$_6$) ppm 7.58 (dd, 1 H), 7.41 (dd, 1 H), 7.33 (t, 1 H), 7.26 (dd, 1 H), 6.30 (dd, 1 H), 6.13 (s, 1 H), 5.51-5.77 (m, 1 H), 5.44 (dd, 1 H), 4.73 (t, 1 H), 4.13-4.24 (m, 1 H), 4.06 (d, 1 H), 4.06 (dd, 1 H), 3.98 (d, 1 H), 3.89 (dd, 1 H), 3.46-3.60 (m, 1 H), 3.37-3.46 (m, 1 H), 2.56-2.70 (m, 1 H), 2.13-2.33 (m, 3 H), 1.78-1.98 (m, 1 H), 1.52-1.68 (m, 3 H), 1.49 (s, 3 H), 1.41-1.48 (m, 1 H), 0.80 (s, 3 H) |
| 56 | 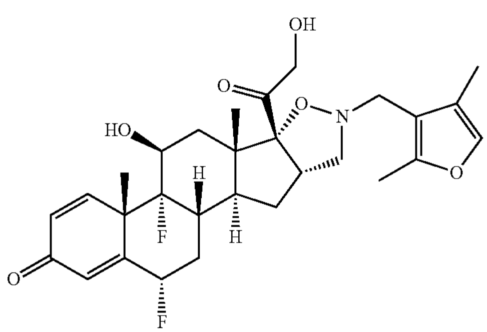 | 76% | LC-MS (ESI POS): 533.1 MH+<br>$[a]_D^{25}$ = +120.1 (c = 0.16, CHCl$_3$)<br>$^1$H NMR (300 MHz, DMSO-d$_6$) ppm 7.26 (dd, 1 H), 6.30 (dd, 1 H), 6.12 (s, 1 H), 5.50-5.81 (m, 1 H), 5.46 (d, 1 H), 4.70 (t, 1 H), 4.10-4.25 (m, 1 H), 4.01 (dd, 1 H), 3.92 (dd, 1 H), 3.74 (d, 1 H), 3.51 (d, 1 H), 3.43-3.48 (m, 1 H), 3.34-3.40 (m, 1 H), 2.55-2.71 (m, 1 H), 2.29 (s, 3 H), 2.16-2.27 (m, 2 H), 2.13 (s, 3 H), 2.02-2.10 (m, 1 H), 1.80-1.95 (m, 1 H), 1.52-1.68 (m, 3 H), 1.49 (s, 3 H), 1.38-1.47 (m, 1 H), 0.80 (s, 3 H) |

TABLE 2-continued

| Compound | Structure | Yield | Analytical |
|---|---|---|---|
| 57 | 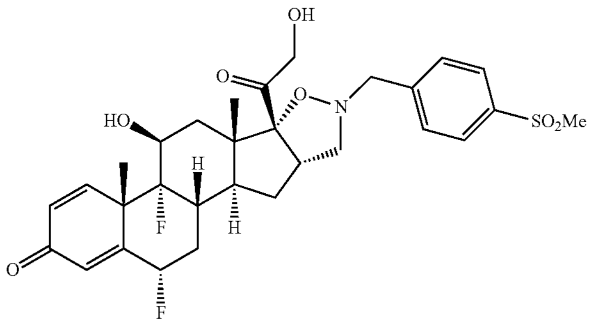 | 75% | LC-MS (ESI POS): 592.41 MH+<br>[a]$_D^{25}$ = +175.6 (c = 0.2, MeOH)<br>$^1$H NMR (300 MHz, DMSO-d$_6$) ppm 7.72-7.96 (m, 2 H), 7.45-7.60 (m, 2 H), 7.25 (d, 1 H), 6.30 (dd, 1 H), 6.12 (s, 1 H), 5.51-5.74 (m, 1 H), 5.44 (d, 1 H), 4.75 (br. s., 1 H), 4.00-4.23 (m, 3 H), 3.81-3.96 (m, 2 H), 3.47-3.63 (m, 1 H), 3.36-3.47 (m, 1 H), 3.18 (s, 3 H), 2.63 (br. s., 1 H), 2.05-2.26 (m, 3 H), 1.81-1.95 (m, 1 H), 1.52-1.72 (m, 3 H), 1.49 (s, 3 H), 1.38-1.47 (m, 1 H), 0.80 (s, 3 H) |
| 58 | 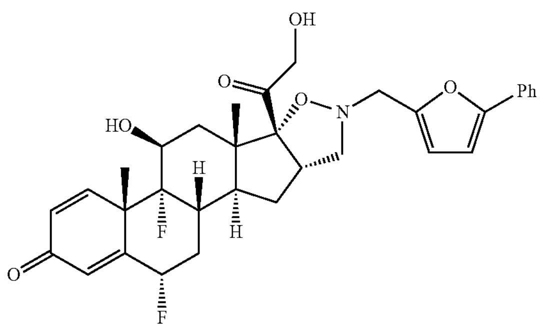 | 93% | LC-MS (ESI POS): 580.46 MH+<br>[a]$_D^{25}$ = +120.8 (c = 0.2, CHCl$_3$)<br>$^1$H NMR (300 MHz, DMSO-d$_6$) ppm 7.56-7.70 (m, 2 H), 7.33-7.45 (m, 2 H), 7.18-7.33 (m, 2 H), 6.86 (d, 1 H), 6.41 (d, 1 H), 6.30 (dd, 1 H), 6.12 (s, 1 H), 5.50-5.74 (m, 1 H), 5.44 (dd, 1 H), 4.70 (br. s., 1 H), 4.33 (dd, 1 H), 4.10-4.23 (m, 1 H), 3.95-4.10 (m, 2 H), 3.88 (m, 1 H), 3.46-3.62 (m, 1 H), 3.34-3.46 (m, 1 H), 2.56-2.67 (m, 1 H), 2.06-2.31 (m, 3 H), 1.87-2.02 (m, 1 H), 1.52-1.70 (m, 3 H), 1.49 (s, 3 H), 1.38-1.47 (m, 1 H), 0.82 (s, 3 H) |
| 59 | 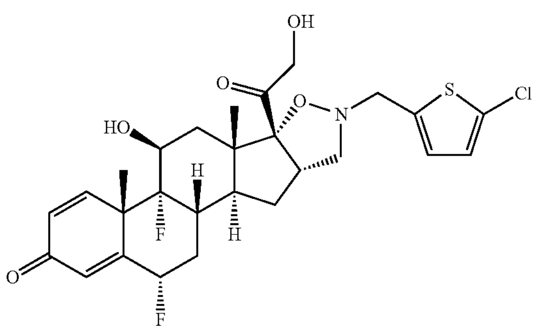 | 64% | LC-MS (ESI POS): 554.36 MH+<br>[a]$_D^{25}$ = +174.0 (c = 0.2, CHCl$_3$)<br>$^1$H NMR (300 MHz, DMSO-d$_6$) ppm 7.26 (dd, 1 H), 6.95 (d, 1 H), 6.84 (d, 1 H), 6.30 (dd, 1 H), 6.12 (s, 1 H), 5.49-5.74 (m, 1 H), 5.45 (d, 1 H), 4.79 (t, 1 H), 4.35 (dd, 1 H), 4.10-4.24 (m, 2 H), 4.03 (m, 1 H), 3.90 (d, 1 H), 3.45-3.58 (m, 1 H), 3.35-3.46 (m, 1 H), 2.58-2.70 (m, 1 H), 2.03-2.25 (m, 3 H), 1.90-1.99 (m, 1 H), 1.52-1.72 (m, 3 H), 1.49 (s, 3 H), 1.42 (dd, 1 H), 0.81 (s, 3 H) |
| 60 | 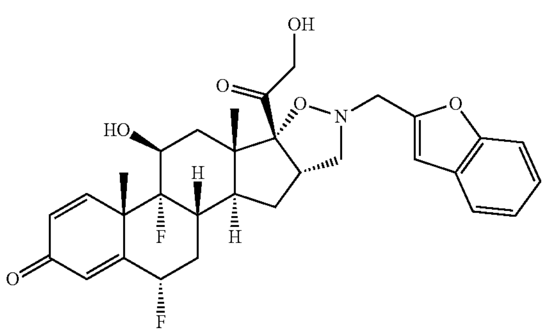 | 63% | LC-MS (ESI POS): 554.2 MH+<br>[a]$_D^{25}$ = +159.9 (c = 0.2, CHCl$_3$)<br>$^1$H NMR (300 MHz, DMSO-d$_6$) ppm 7.55-7.64 (m, 1 H), 7.50 (d, 1 H), 7.13-7.37 (m, 3 H), 6.78 (s, 1 H), 6.30 (dd, 1 H), 6.12 (s, 1 H), 5.50-5.80 (m, 1 H), 5.44 (d, 1 H), 4.62-4.83 (m, 1 H), 4.23-4.42 (m, 1 H), 4.09-4.23 (m, 2 H), 3.89-4.04 (m, 2 H), 3.48-3.63 (m, 1 H), 3.36-3.48 (m, 1 H), 2.56-2.67 (m, 1 H), 2.10-2.35 (m, 3 H), 1.82-2.01 (m, 1 H), 1.52-1.72 (m, 3 H), 1.49 (s, 3 H), 1.36-1.48 (m, 1 H), 0.81 (s, 3 H) |

TABLE 2-continued

| Compound | Structure | Yield | Analytical |
|---|---|---|---|
| 61 | 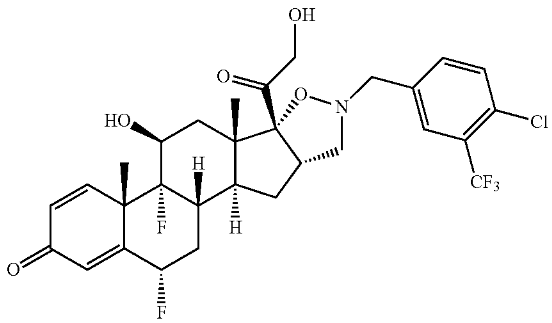 | 50% | LC-MS (ESI POS): 615.97 MH+<br>[a]$_D^{25}$ = +185.7 (c = 0.2, CHCl$_3$)<br>$^1$H NMR (300 MHz, DMSO-d$_6$) ppm 7.75 (d, 1 H), 7.68 (d, 1 H), 7.59 (dd, 1 H), 7.25 (dd, 1 H), 6.30 (dd, 1 H), 6.12 (s, 1 H), 5.49-5.80 (m, 1 H), 5.44 (d, 1 H), 4.60-4.84 (m, 1 H), 4.10-4.28 (m, 1 H), 3.94-4.10 (m, 2 H), 3.75-3.94 (m, 2 H), 3.48-3.60 (m, 1 H), 3.37-3.47 (m, 1 H), 2.58-2.68 (m, 1 H), 2.08-2.25 (m, 3 H), 1.76-2.00 (m, 1 H), 1.51-1.72 (m, 3 H), 1.48 (s, 3 H), 1.39-1.46 (m, 1 H), 0.80 (s, 3 H) |
| 62 | 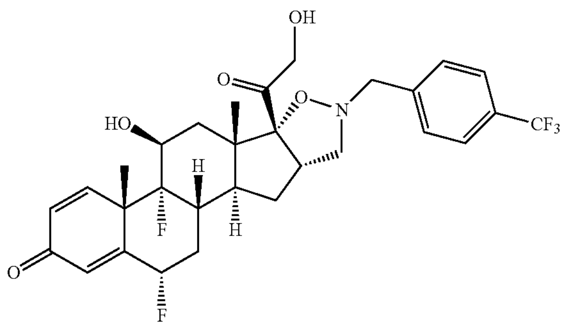 | 51% | LC-MS (ESI POS): 582.27 MH+<br>[a]$_D^{25}$ = +171.5 (c = 0.2, CHCl$_3$)<br>$^1$H NMR (300 MHz, DMSO-d$_6$) ppm 7.59-7.76 (m, 2 H), 7.41-7.57 (m, 2 H), 7.25 (dd, 1 H), 6.30 (dd, 1 H), 6.06-6.16 (m, 1 H), 5.50-5.77 (m, 1 H), 5.44 (d, 1 H), 4.72 (br. s., 1 H), 4.09-4.24 (m, 1 H), 3.97-4.11 (m, 2 H), 3.76-3.97 (m, 2 H), 3.48-3.66 (m, 1 H), 3.38-3.48 (m, 1 H), 2.55-2.61 (m, 1 H), 2.03-2.27 (m, 2 H), 1.79-1.94 (m, 1 H), 1.51-1.67 (m, 4 H), 1.48 (s, 3 H), 1.37-1.46 (m, 1 H), 0.80 (s, 3 H) |
| 63 | 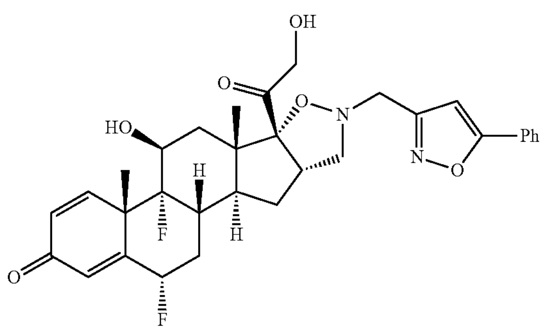 | 70% | LC-MS (ESI POS): 581.08 MH+<br>[a]$_D^{25}$ = +120.9 (c = 0.2, CHCl$_3$)<br>$^1$H NMR (300 MHz, DMSO-d$_6$) ppm 7.71-7.90 (m, 2 H), 7.45-7.59 (m, 3 H), 7.26 (dd, 1 H), 6.88 (s, 1 H), 6.31 (dd, 1 H), 6.10 (s, 1 H), 5.50-5.73 (m, 1 H), 5.39-5.48 (m, 1 H), 4.77 (dd, 1 H), 4.32-4.44 (m, 1 H), 4.09-4.25 (m, 2 H), 3.79-4.09 (m, 2 H), 3.51-3.67 (m, 1 H), 3.38-3.51 (m, 1 H), 2.60 (d, 1 H), 2.08-2.25 (m, 3 H), 1.87-2.06 (m, 1 H), 1.53-1.69 (m, 3 H), 1.49 (s, 3 H), 1,39-1.46 (m, 1 H), 0.82 (s, 3 H) |
| 64 | 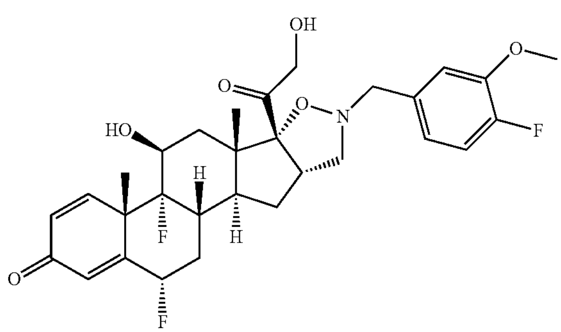 | 37% | LC-MS (ESI POS): 562.07 MH+<br>[a]$_D^{25}$ = +185.6 (c = 0.2, CHCl$_3$)<br>$^1$H NMR (300 MHz, DMSO-d$_6$) ppm 7.25 (dd, 1 H), 7.12 (dd, 1 H), 7.06 (dd, 1 H), 6.82 (ddd, 1 H), 6.30 (dd, 1 H), 6.12 (s, 1 H), 5.51-5.78 (m, 1 H), 5.43 (br. s., 1 H), 4.58-4.81 (m, 1 H), 4.08-4.31 (m, 2 H), 3.84-4.01 (m, 2 H), 3.80 (s, 3 H), 3.71 (d, 1 H), 3.45-3.56 (m, 1 H), 3.34-3.44 (m, 1 H), 2.55-2.62 (m, 1 H), 2.07-2.26 (m, 3 H), 1.82-1.98 (m, 1 H), 1.52-1.68 (m, 3 H), 1.49 (s, 3 H), 1.39-1.47 (m, 1 H), 0.80 (s, 3 H) |

TABLE 2-continued

| Compound | Structure | Yield | Analytical |
|---|---|---|---|
| 65 | 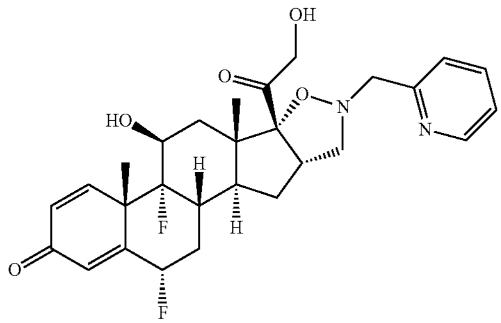 | 21% | LC-MS (ESI POS): 515.29 MH+<br>$[a]_D^{25}$ = +129.7 (c = 0.2, CHCl$_3$)<br>$^1$H NMR (300 MHz, DMSO-d$_6$) ppm 8.42-8.54 (m, 1 H) 7.75 (td, 1 H) 7.36 (d, 1 H) 7.21-7.31 (m, 2 H) 6.30 (dd, 1 H) 6.12 (s, 1 H) 5.48-5.75 (m, 1 H) 5.43 (d, 1 H) 4.64-4.80 (m, 1 H) 4.09-4.28 (m, 2 H) 3.99-4.09 (m, 1 H) 3.82-3.96 (m, 2 H) 3.37-3.61 (m, 2 H) 2.57 (br. s., 1 H) 2.08-2.26 (m, 2 H) 1.80-1.94 (m, 1 H) 1.52-1.69 (m, 2 H) 1.48 (s, 3 H) 1.40-1.53 (m, 2 H) 0.80 (s, 3 H) |
| 66 | 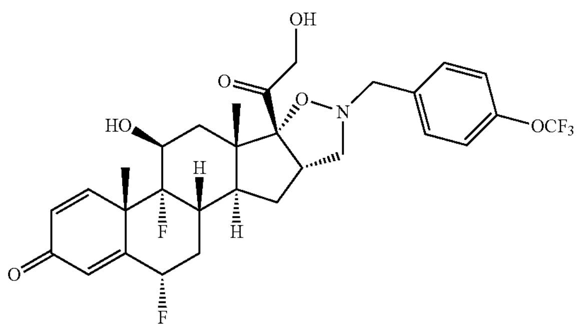 | 65% | LC-MS (ESI POS): 597.99 MH+<br>$[a]_D^{25}$ = +174.3 (c = 0.2, CHCl$_3$)<br>$^1$H NMR (300 MHz, DMSO-d$_6$) ppm 7.34-7.46 (m, 2 H), 7.26-7.34 (m, 2 H), 7.26 (dd, 1 H), 6.30 (dd, 1 H), 6.12 (s, 1 H), 5.49-5.76 (m, 1 H), 5.40-5.47 (m, 1 H), 4.69 (br. s., 1 H), 4.04-4.23 (m, 2 H), 3.96 (d, 1 H), 3.90 (dd, 1 H), 3.80 (d, 1 H), 3.44-3.57 (m, 1 H), 335-3.44 (m, 1 H), 2.54-2.66 (m, 1 H), 2.04-2.27 (m, 3 H), 1.82-1.96 (m, 1 H), 1.51-1.69 (m, 3 H), 1.49 (s, 3 H), 1.43 (dd, 1 H), 0.80 (s, 3 H) |
| 67 | 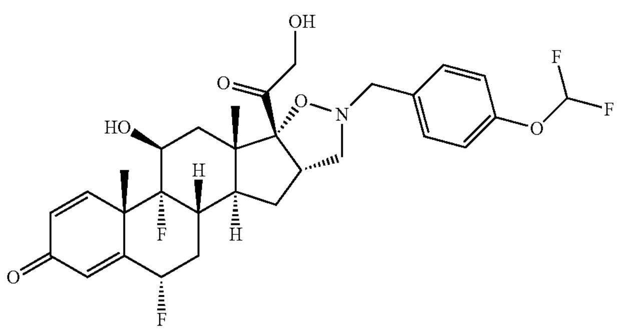 | 37% | LC-MS (ESI POS): 580.47 MH+<br>$[a]_D^{25}$ = +178.2 (c = 0.2, CHCl$_3$)<br>$^1$H NMR (300 MHz, DMSO-d$_6$) ppm 7.29-7.36 (m, 2 H), 7.26 (dd, 1 H), 7.07-7.14 (m, 2 H), 7.19 (t, 1 H), 6.30 (dd, 1 H), 6.12 (s, 1 H), 5.50-5.75 (m, 1 H), 5.44 (d, 1 H), 4.57-4.75 (m, 1 H), 4.06-4.27 (m, 2 H), 3.91 (dd, 1 H), 3.90 (d, 1 H), 3.77 (d, 1 H), 3.43-3.56 (m, 1 H), 3.34-3.42 (m, 1 H), 2.55-2.63 (m, 1 H), 2.04-2.26 (m, 3 H), 1.82-1.97 (m, 1 H), 1.51-1.68 (m, 3 H), 1.49 (s, 3 H), 1.44 (dd, 1 H), 0.80 (s, 3 H) |
| 68 | 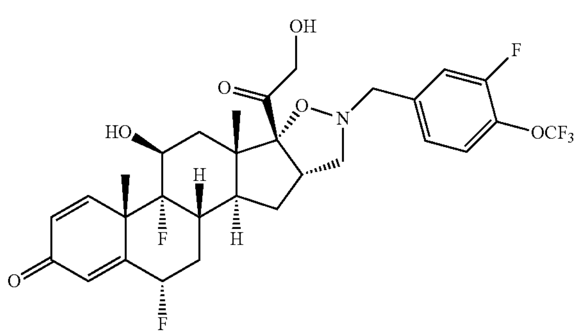 | 65% | LC-MS (ESI POS): 616.41 MH+<br>$[a]_D^{25}$ = +173.3 (c = 0.2, CHCl$_3$)<br>$^1$H NMR (300 MHz, DMSO-d$_6$) ppm 7.45-7.60 (m, 1 H), 7.38 (dd, 1 H), 7.14-7.32 (m, 2 H), 6.30 (dd, 1 H), 6.12 (s, 1 H), 5.50-5.79 (m, 1 H), 5.44 (d, 1 H), 4.64-4.83 (m, 1 H), 4.05-4.26 (m, 2 H), 4.00 (d, 1 H), 3.92 (dd, 1 H), 3.80 (d, 1 H), 3.45-3.58 (m, 1 H), 3.34-3.45 (m, 1 H), 2.56-2.69 (m, 1 H), 2.01-2.26 (m, 3 H), 1.77-1.98 (m, 1 H), 1.50-1.69 (m, 3 H), 1.48 (s, 3 H), 1.43 (dd, 1 H), 0.80 (s, 3 H) |

TABLE 2-continued

| Compound | Structure | Yield | Analytical |
|---|---|---|---|
| 69 | 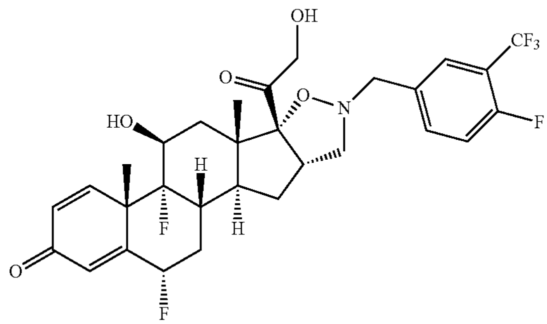 | 53% | LC-MS (ESI POS): 600.25 MH+<br>[a]$_D^{25}$ = +178.9 (c = 0.2, CHCl$_3$)<br>$^1$H NMR (300 MHz, DMSO-d$_6$) ppm 7.59-7.71 (m, 2 H), 7.39-7.53 (m, 1 H), 7.25 (dd, 1 H), 6.30 (dd, 1 H), 6.12 (s, 1 H), 5.49-5.79 (m, 1 H), 5.44 (br. s., 1 H), 4.49-4.82 (m, 1 H), 3.75-4.30 (m, 5 H), 3.45-3.60 (m, 1 H), 3.34-3.44 (m, 1 H), 2.56-2.63 (m, 1 H), 2.07-2.25 (m, 3 H), 1.81-1.96 (m, 1 H), 1.52-1.71 (m, 3 H), 1.49 (s, 3 H), 1.37-1.47 (m, 1 H), 0.80 (s, 3 H) |
| 70 | 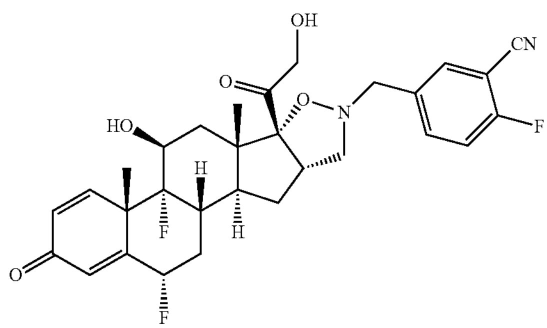 | 61% | LC-MS (ESI POS): 557.44 MH+<br>[a]$_D^{25}$ = +208.6 (c = 0.2, CHCl$_3$)<br>$^1$H NMR (300 MHz, DMSO-d$_6$) ppm 7.80 (dd, 1 H), 7.69 (ddd, 1 H), 7.48 (dd, 1 H), 7.25 (dd, 1 H), 6.30 (dd, 1 H), 6.12 (s, 1 H), 5.51-5.74 (m, 1 H), 5.44 (br. s., 1 H), 4.63-4.78 (m, 1 H), 4.10-4.24 (m, 1 H), 3.86-4.09 (m, 3 H), 3.71-3.89 (m, 1 H), 3.44-3.55 (m, 1 H), 3.34-3.44 (m, 1 H), 2.57-2.67 (m, 1 H), 2.02-2.26 (m, 3 H), 1.81-1.94 (m, 1 H), 1.52-1.70 (m, 3 H), 1.49 (s, 3 H), 1.34-1.47 (m, 1 H), 0.80 (s, 3 H) |
| 71 | 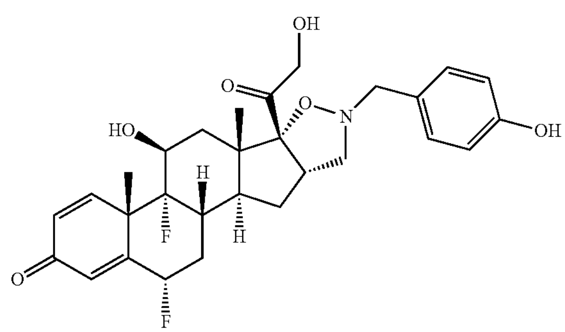 | 38% | LC-MS (ESI POS): 530.34 MH+<br>[a]$_D^{25}$ = +168.8 (c = 0.2, MeOH)<br>$^1$H NMR (300 MHz, DMSO-d$_6$) ppm 9.27 (s, 1 H), 7.18-7.34 (m, 1 H), 6.98-7.10 (m, 2 H), 6.61-6.75 (m, 2 H), 6.30 (dd, 1 H), 6.12 (q, 1 H), 5.50-5.73 (m, 1 H), 5.43 (d, 1 H), 4.50-4.75 (m, 1 H), 4.10-4.28 (m, 2 H), 3.86-3.99 (m, 1 H), 3.62-3.80 (m, 2 H), 3.33-3.52 (m, 2 H), 2.55-2.63 (m, 1 H), 1.84-2.23 (m, 3 H), 1.52-1.69 (m, 3 H), 1.49 (s, 3 H), 1.36-1.47 (m, 1 H), 0.80 (s, 3 H) |

TABLE 2-continued

| Compound | Structure | Yield | Analytical |
|---|---|---|---|
| 72 | 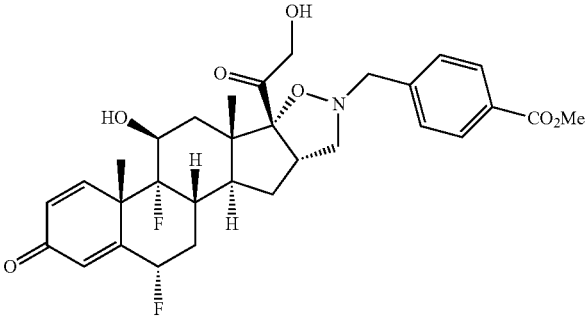 | 47% | LC-MS (ESI POS): 572.44 MH+<br>$[\alpha]_D^{25}$ = +216.1 (c = 0.2, MeOH)<br>$^1$H NMR (300 MHz, DMSO-d6) ppm 7.83-8.01 (m, 2 H), 7.36-7.54 (m, 2 H), 7.25 (dd, 1 H), 6.30 (dd, 1 H), 6.13 (s, 1 H), 5.48-5.78 (m, 1 H), 5.43 (dd, 1 H), 4.70 (t, 1 H), 4.11-4.25 (m, 1 H), 3.94-4.13 (m, 2 H), 3.87-3.92 (m, 1 H), 3.85 (s, 3 H), 3.71-3.83 (m, 1 H), 3.46-3.57 (m, 1 H), 3.34-3.46 (m, 1 H), 2.56-2.69 (m, 1 H), 2.04-2.34 (m, 3 H), 1.81-2.00 (m, 1 H), 1.52-1.70 (m, 3 H), 1.49 (s, 3 H), 1.37-1.47 (m, 1 H), 0.80 (s, 3 H) |
| 73 | 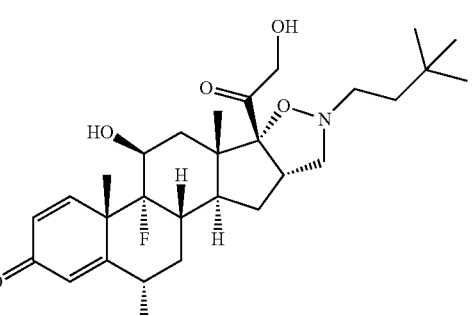 | 48% | LC-MS (ESI POS): 508.26 MH+<br>$[\alpha]_D^{25}$ = +131.4 (c 0.213; CHCl$_3$)<br>$^1$H NMR (300 MHz, DMSO-d6) ppm 7.25 (dd, 1 H) 6.29 (dd, 1 H) 6.11 (s, 1 H) 5.49-5.79 (m, 1 H) 5.44 (d, 1 H) 4.77 (t, 1 H) 4.48 (dd, 1 H) 4.12-4.24 (m, 1 H) 4.12 (dd, 1 H) 3.43-3.60 (m, 1 H) 3.31-3.43 (m, 1 H) 2.54-2.72 (m, 3 H) 2.08-2.34 (m, 2 H) 1.80-2.01 (m, 2 H) 1.51-1.71 (m, 3 H) 1.49 (s, 3 H) 1.18-1.46 (m, 3 H) 0.86 (s, 9 H) 0.81 (s, 3 H) |

Example 4

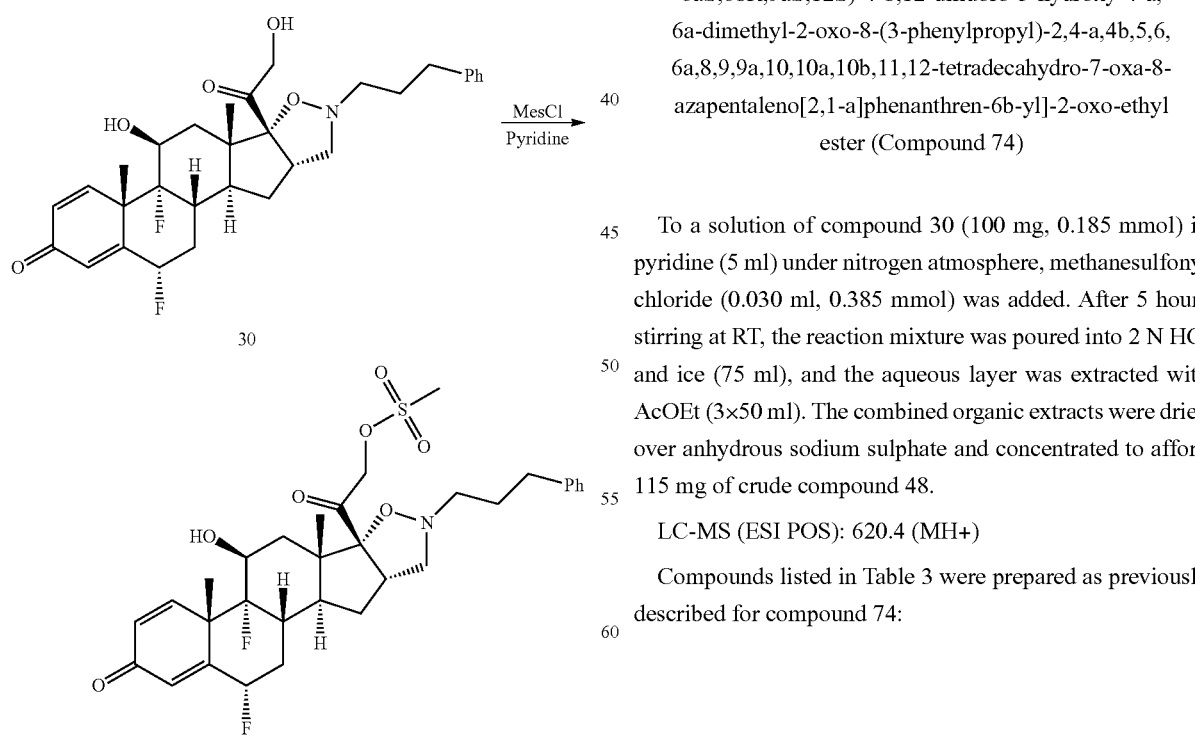

Preparation of methanesulfonic acid 2-[(4aS,4bR,5S,6aS,6bR,9aS,12S)-4-b,12-difluoro-5-hydroxy-4-a,6a-dimethyl-2-oxo-8-(3-phenylpropyl)-2,4-a,4b,5,6,6a,8,9,9a,10,10a,10b,11,12-tetradecahydro-7-oxa-8-azapentaleno[2,1-a]phenanthren-6b-yl]-2-oxo-ethyl ester (Compound 74)

To a solution of compound 30 (100 mg, 0.185 mmol) in pyridine (5 ml) under nitrogen atmosphere, methanesulfonyl chloride (0.030 ml, 0.385 mmol) was added. After 5 hours stirring at RT, the reaction mixture was poured into 2 N HCl and ice (75 ml), and the aqueous layer was extracted with AcOEt (3×50 ml). The combined organic extracts were dried over anhydrous sodium sulphate and concentrated to afford 115 mg of crude compound 48.

LC-MS (ESI POS): 620.4 (MH+)

Compounds listed in Table 3 were prepared as previously described for compound 74:

TABLE 3

| Compound | Structure | Yield | Analytical |
|---|---|---|---|
| 75 | 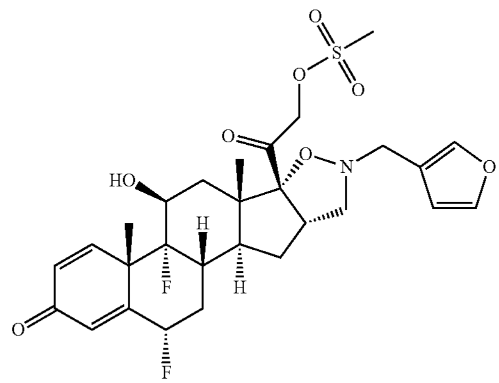 | 95% | LC-MS (ESI POS): 582.3 (MH+) |
| 76 | 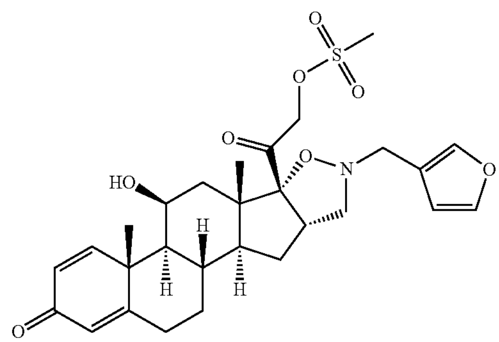 | 77% | LC-MS (ESI POS): 546.2 (MH+) |
| 77 | 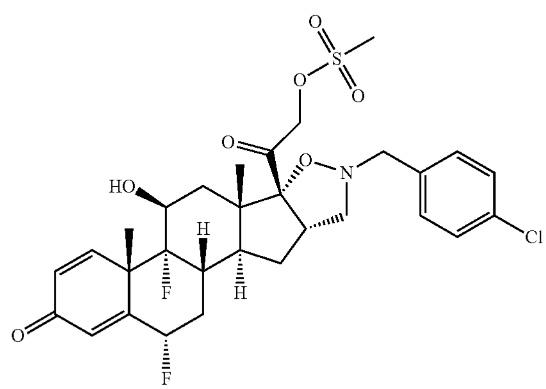 | 99% | LC-MS (ESI POS): 626.3 (MH+) |
| 78 | 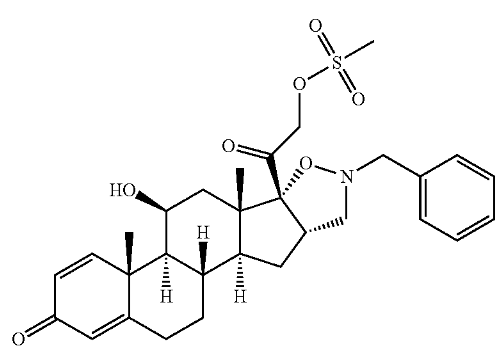 | 99% | LC-MS (ESI POS): 556.18 (MH+) |

TABLE 3-continued
| Compound | Structure | Yield | Analytical |
|---|---|---|---|
| 79 | 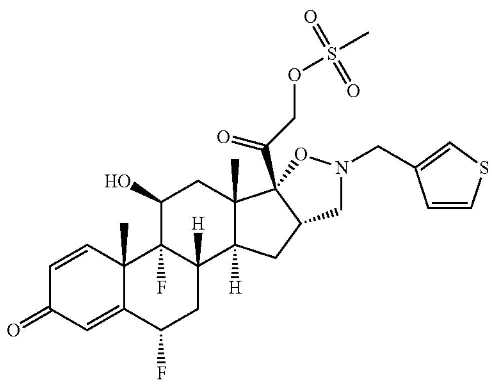 | 67% | LC-MS (ESI POS): 598.1 (MH+) |
| 80 | 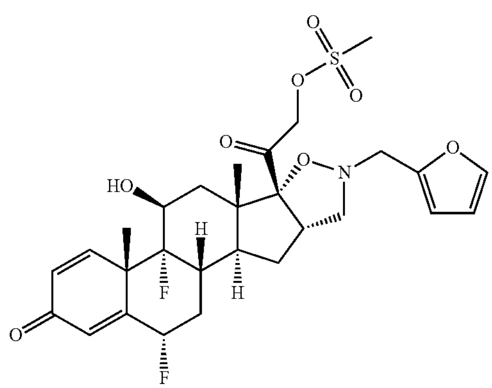 | 97% | LC-MS (ESI POS): 582.3 (MH+) |
Example 5
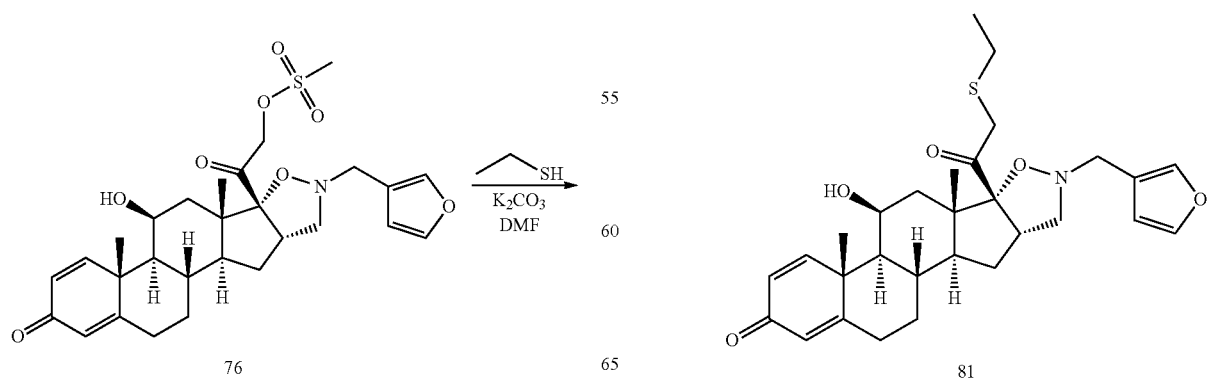
-continued

Preparation of (4aR,5S,6aS,6bR,9aS)-6b-(2-Ethyl-sulfanyl-acetyl)-8-furan-3-ylmethyl-5-hydroxy-4-a,6a-dimethyl-4-a,4b,5,6,6a,6b,8,9,9a,10,10a,10b,11,12-tetradecahydro-7-oxa-8-aza-pentaleno[2,1-a]phenanthren-2-one (Compound 81)

To a dispersion of K$_2$CO$_3$ (41 mg, 0.297 mmol) in anhydrous DMF (1 ml), under nitrogen atmosphere, ethane thiol (15 ml, 0.196 mmol) was added. After 10 minutes stirring, compound 76 (107 mg, 0.196 mmol) dissolved in anhydrous DMF (2 ml) was dropped therein. The reaction mixture was stirred at RT for 1.5 hours and then poured into 2 N HCl (20 ml) and ice. The aqueous layer was extracted with AcOEt (3×30 ml), and the combined organic extracts were dried over anhydrous sodium sulphate and concentrated. The crude material was purified by column chromatography on silica gel, in gradient elution from AcOEt/Petroleum ether 10:90 to AcOEt/Petroleum ether 40:60, to afford 68 mg of the title compound (68% yield).

$^1$H NMR (300 MHz, CHLOROFORM-d) ppm 7.38 (t, 1H), 7.33-7.36 (m, 1H), 7.26 (d, 1H), 6.37 (dd, 1H), 6.30 (dd, 1H), 6.05 (t, 1H), 4.50 (quin, 1H), 3.73 (s, 2H), 3.44 (d, 1H), 3.35-3.61 (m, 2H), 3.40 (d, 1H), 2.43-2.73 (m, 3H), 2.36 (ddd, 1H), 1.92-2.28 (m, 4H), 1.60-1.91 (m, 3H), 1.47 (s, 3H), 1.41-1.54 (m, 1H), 1.23 (t, 3H), 1.08-1.38 (m, 3H), 0.99 (s, 3H).

LC-MS (ESI POS): 512.09 (MH+)

The compounds listed in Table 4 were prepared as previously described for compound 81.

TABLE 4

| Compound | Structure | Yield | Analytical |
|---|---|---|---|
| 82 | 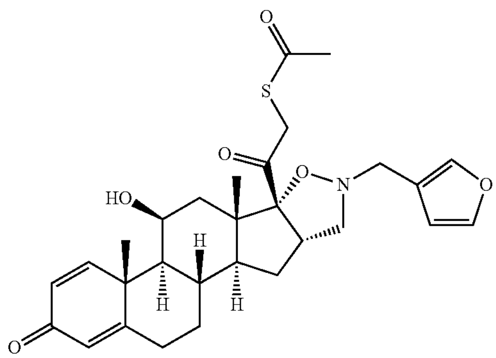 | 66% | LC-MS (ESI POS): 526.12 (MH+)<br>$^1$H NMR (300 MHz, CHLOROFORM-d) ppm 7.34-7.43 (m, 1 H), 7.30 (d, 1 H), 6.38 (t, 1 H), 6.32 (dd, 1 H), 6.06 (t, 1 H), 4.52 (q, 1 H), 3.95 (d, 1 H), 3.65-3.86 (m, 2 H), 3.36-3.63 (m, 1 H), 2.47-2.76 (m, 1 H), 2.31-2.46 (m, 1 H), 2.38 (s, 3 H), 1.91-2.31 (m, 5 H), 1.59-1.87 (m, 5 H), 1.48 (s, 3 H), 1.39-1.59 (m, 1 H), 1.08-1.38 (m, 3 H), 0.98 (s, 3 H) |
| 83 | 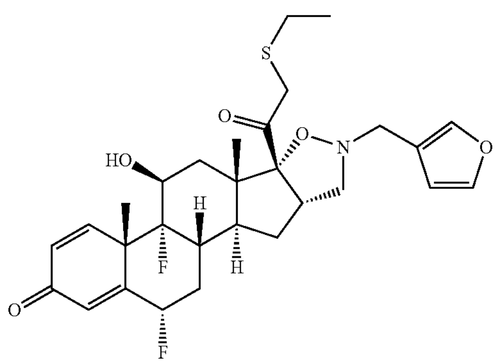 | 77% | LC-MS (ESI POS): 548.11 (MH+)<br>$^1$H NMR (300 MHz, CHLOROFORM-d) ppm 7.32-7.48 (m, 2 H), 7.12 (dd, 1 H), 6.46 (s, 1 H), 6.40 (dd, 1 H), 6.35-6.38 (m, 1 H), 5.41 (dddd, 1 H), 4.29-4.56 (m, 1 H), 3.78 (s, 2 H), 3.48-3.65 (m, 2 H), 3.48 (d, 1 H), 3.39 (d, 1 H), 2.18-2.72 (m, 6 H), 2.10 (br. s, 1 H), 1.63-1.94 (m, 3 H), 1.55 (s, 3 H), 1.35-1.64 (m, 2 H), 1.23 (t, 3 H), 1.00 (s, 3 H) |
| 84 | 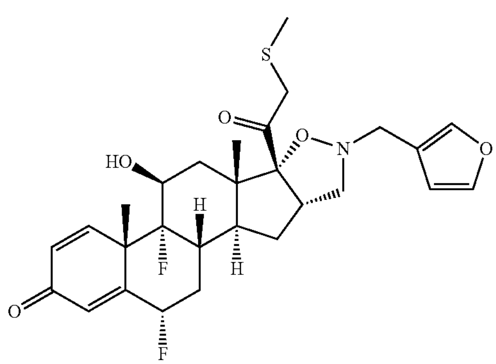 | 63% | LC-MS (ESI POS): 534.16 (MH+)<br>$^1$H NMR (300 MHz, CHLOROFORM-d) ppm 7.38 (t, 1 H), 7.34-7.36 (m, 1 H), 7.12 (dd, 1 H), 6.43-6.49 (m, 1 H), 6.40 (dd, 1 H), 6.36 (dd, 1 H), 5.41 (dddd, 1 H), 4.32-4.52 (m, 1 H), 3.77 (s, 2 H), 3.38-3.67 (m, 3 H), 3.28 (d, 1 H), 2.25-2.57 (m, 4 H), 2.01-2.14 (m, 1 H), 2.09 (s, 3 H), 1.64-1.92 (m, 3 H), 1.55 (s, 3 H), 1.37-1.52 (m, 2 H), 1.00 (s, 3 H) |

TABLE 4-continued

| Compound | Structure | Yield | Analytical |
|---|---|---|---|
| 85 | 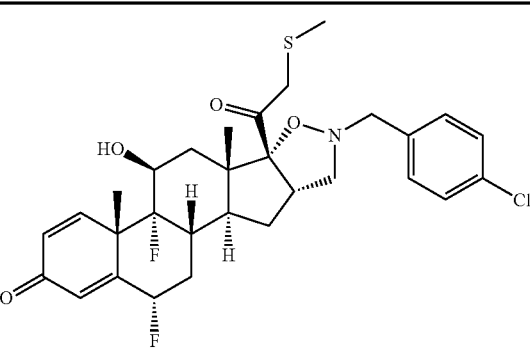 | 69% | LC-MS (ESI POS): 578.34 MH+<br>$[\alpha]_D^{25}$ = +169.3 (c = 0.2, MeOH)<br>$^1$H NMR (300 MHz, DMSO-d$_6$) ppm 7.28-7.45 (m, 4 H), 7.26 (dd, 1 H), 6.30 (dd, 1 H), 6.13 (s, 1 H), 5.50-5.74 (m, 1 H), 5.43 (dd, 1 H), 4.16 (m, 1 H), 3.94 (d, 1 H), 3.75 (d, 1 H), 3.43-3.64 (m, 1 H), 3.31-3.43 (m, 1 H), 3.26 (s, 2 H), 2.54-2.68 (m, 1 H), 2.04-2.35 (m, 3 H), 1.84-1.99 (m, 1 H), 1.92 (s, 3 H), 1.51-1.78 (m, 3 H), 1.49 (s, 3 H), 1.36-1.51 (m, 1 H), 0.82 (s, 3 H) |
| 86 | 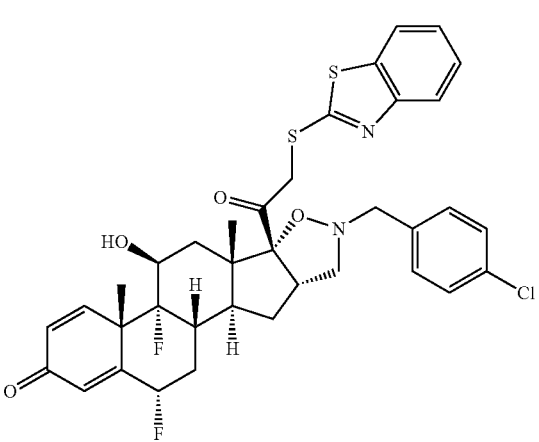 | 26% | LC-MS (ESI POS): 697.16 MH+<br>$[\alpha]_D^{25}$ = +200.1 (c = 0.265, CHCl$_3$)<br>$^1$H NMR (300 MHz, CHLOROFORM-d) ppm 7.70-7.87 (m, 2 H), 7.38-7.46 (m, 1 H) 7.31-7.35 (m, 1 H) 7.24-7.30 (m , 4 H) 7.14 (dd, 1 H) 6.45-6.51 (m, 1 H) 6.42 (dd, 1 H) 5.41 (dddd, 1 H) 4.41-4.53 (m, 1 H) 4.34 (d, 1 H) 4.03 (d, 1 H) 3.90 (s, 2 H) 3.47-3.68 (m, 2 H) 2.24-2.62 (m, 4 H) 1.96 (d, 1 H) 1.73-1.90 (m, 3 H) 1.56 (s, 3 H) 1.50 (dd, 1 H) 1.02 (s, 3 H) |
| 87 | 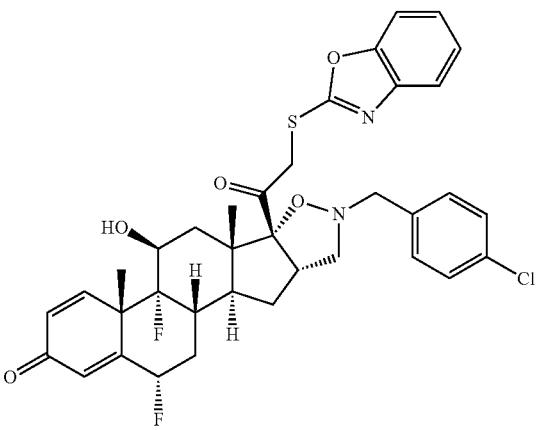 | 68% | LC-MS (ESI POS): 681.32 MH+<br>$[\alpha]_D^{25}$ = +173.5 (c = 0.44, CHCl$_3$)<br>$^1$H NMR (300 MHz, CHLOROFORM-d) ppm 7.37-7.59 (m, 2 H) 7.20-7.37 (m, 6 H) 7.16 (dd, 1 H) 6.48 (s, 1 H) 6.41 (dd, 1 H) 5.41 (dddd, 1 H) 4.37-4.53 (m, 1 H) 4.25 (d, 1 H) 4.12 (d, 1 H) 3.94 (s, 2 H) 3.41-3.73 (m, 2 H) 2.17-2.58 (m, 5 H) 1.92-2.17 (m, 1 H) 1.66-1.92 (m, 2 H) 1.56 (s, 3 H) 1.43-1.54 (m, 1 H) 1.03 (s, 3 H) |

Example 6

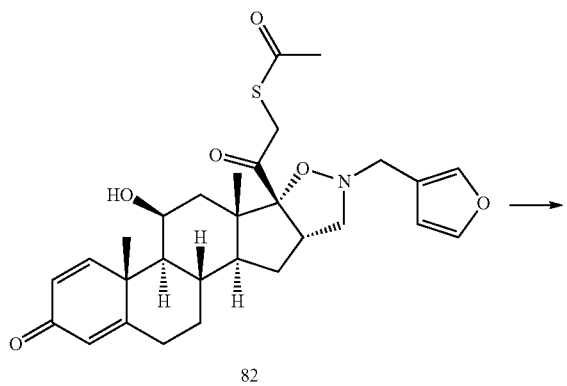

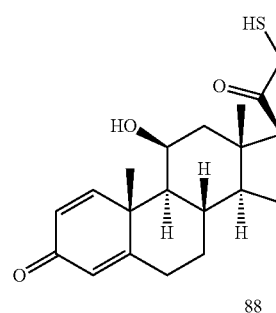

Preparation of (4aR,5S,6aS,6bR,9aS)-8-Furan-3-ylmethyl-5-hydroxy-6b-(2-mercapto-acetyl)-4-a,6a-dimethyl-4-a,4b,5,6,6a,6b,8,9,9a,10,10a, 10b,11,12-tetradecahydro-7-oxa-8-aza-pentaleno[2,1-a]phenanthren-2-one (Compound 88)

To a solution of compound 82 (63 mg, 0.120 mmol) in degassed ethanol (7 ml) and water (3 ml), at 0° C. under nitrogen atmosphere, 1 N NaOH (120 µl, 0.120 mmol) was added. After stirring at 0° C. for 3.5 hours, the reaction mixture was poured into 2 N HCl (1 ml) and brine (10 ml). The aqueous layer was extracted with AcOEt (3×20 ml), and the combined organic extracts were dried ($Na_2SO_4$) and concentrated. The crude material was purified by column chromatography on silica gel, in gradient elution from DCM to DCM/AcOEt 80:20, to afford 20 mg of pure compound (34% yield).

$^1$H NMR (300 MHz, DMSO-d6) ppm 7.58 (t, 1H), 7.52-7.57 (m, 1H), 7.31 (d, 1H), 6.41 (dd, 1H), 6.17 (dd, 1H), 5.93 (t, 1H), 4.70 (d, 1H), 4.14-4.44 (m, 1H), 3.76 (d, 1H), 3.66 (d, 1H), 3.62 (dd, 1H), 3.34 (dd, 1H), 3.29-3.53 (m, 2H), 2.52-2.62 (m, 1H), 2.34-2.44 (m, 1H), 2.20-2.35 (m, 1H), 1.87-2.22 (m, 3H), 1.73 (d, 2H), 1.50-1.71 (m, 2H), 1.38 (s, 3H), 1.30-1.51 (m, 1H), 0.99-1.13 (m, 1H), 0.95 (dd, 1H), 0.81 (s, 3H).

LC-MS (ESI POS): 484.09 (MH+)

Example 7

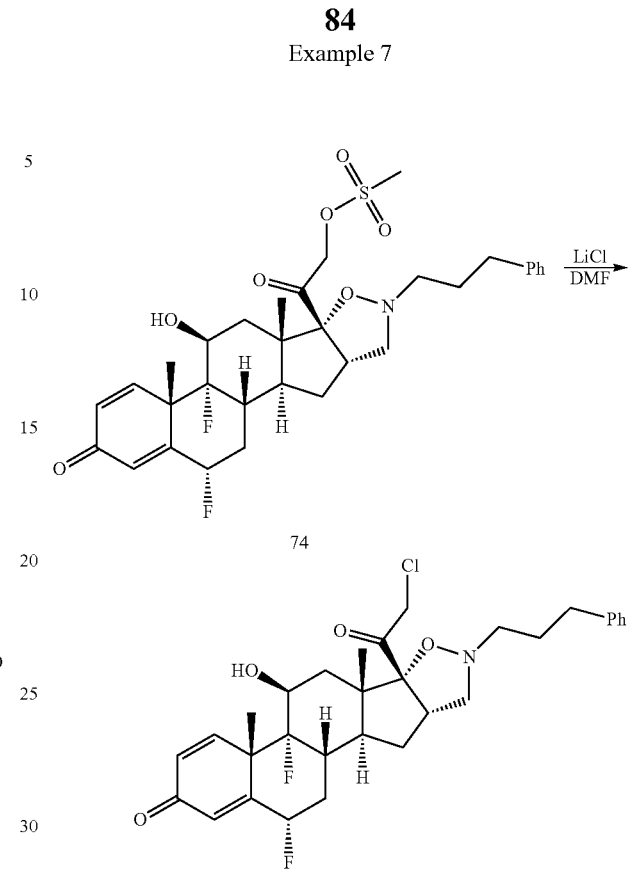

Preparation of (4aS,4bR,5S,6aS,6bR,9aS,10aS,10bS,12S)-6b-(2-Chloro-acetyl)-4-b,12-difluoro-5-hydroxy-4-a,6a-dimethyl-8-(3-phenyl-propyl)-4-a,4b,5,6,6a,6b,8,9,9a,10,10a,10b,11,12-tetradecahydro-7-oxa-8-aza-pentaleno[2,1-a]phenanthren-2-one (Compound 89)

To a solution of lithium chloride (97 mg, 2.285 mmol) in anhydrous DMF (1 ml) under nitrogen atmosphere, compound 74 (118 mg, 0.190 mmol) dissolved in anhydrous DMF (2 ml) was added. The reaction mixture was stirred at 65° C. for 3.5 hours. The reaction mixture was poured into 2N HCl and ice (20 ml), and the aqueous layer was extracted with AcOEt (3×50 ml). The combined organic extracts were washed with water (2×40 ml), brine, dried over anhydrous sodium sulphate and concentrated. The crude material was purified by column chromatography on silica gel, in gradient elution from DCM to DCM/AcOEt 85:15, to afford 78 mg of title compound (73.1% yield).

$^1$H NMR (300 MHz, DMSO-$d_6$) ppm 7.03-7.34 (m, 6H), 6.29 (dd, J=10.12, 1.91 Hz, 1H), 6.11 (s, 1H), 5.49-5.78 (m, 1H), 5.45 (d, J=2.93 Hz, 1H), 4.69 (d, J=17.31 Hz, 1H), 4.54 (d, J=17.31 Hz, 1H), 3.98-4.24 (m, 1H), 3.45-3.62 (m, 1H), 3.33-3.45 (m, 1H), 2.70 (t, J=7.19 Hz, 2H), 2.59 (t, J=7.63 Hz, 2H), 2.05-2.35 (m, 2H), 1.97 (br. s., 2H), 1.54-1.85 (m, 6H), 1.49 (s, 3H), 1.39-1.46 (m, 1H), 0.84 (s, 3H).

LC-MS (ESI POS) 560.0 (MH+)

The compounds listed in Table 5 were prepared as previously described for compound 89.

TABLE 5
| Compound | Structure | Yield | Analytical |
|---|---|---|---|
| 90 | 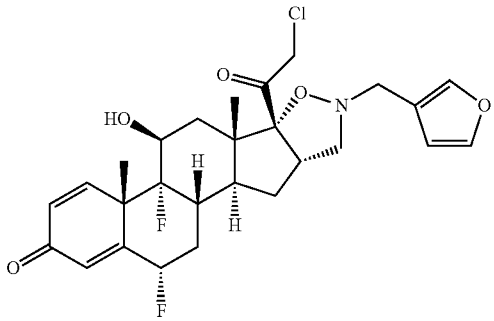 | 66% | LC-MS (ESI POS): 522.05 (MH+)<br>$^1$H NMR (300 MHz, DMSO-$d_6$) ppm 7.61 (t, 1 H), 7.58 (s, 1 H), 7.27 (dd, 1 H), 6.42 (dd, 1 H), 6.30 (dd, 1 H), 6.12 (s, 1 H), 5.50-5.80 (m, 1 H), 5.45 (d, 1 H), 4.50 (d, 1 H), 4.38 (d, 1 H), 4.05-4.24 (m, 1 H), 3.81 (d, 1 H), 3.70 (d, 1 H), 3.43-3.55 (m, 1 H), 3.31-3.43 (m, 1 H), 2.55-2.70 (m, 1 H), 2.02-2.36 (m, 3 H), 1.86-2.02 (m, 1 H), 1.52-1.78 (m, 3 H), 1.49 (s, 3 H), 1.33-1.48 (m, 1 H), 0.83 (s, 3 H) |
| 91 | 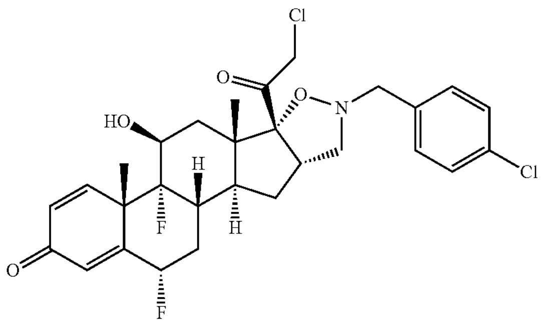 | 46% | LC-MS (ESI POS): 566.02 (MH+)<br>$^1$H NMR (300 MHz, DMSO-$d_6$) ppm 7.18-7.45 (m, 5 H), 6.30 (dd, 1 H), 6.13 (s, 1 H), 5.50-5.82 (m, 1 H), 5.45 (d, 1 H), 4.25 (s, 2 H), 4.08-4.21 (m, 1 H), 3.96 (d, 1 H), 3.79 (d, 1 H), 3.45-3.60 (m, 1 H), 3.33-3.45 (m, 1 H), 2.56-2.69 (m, 1 H), 2.08-2.33 (m, 3 H), 1.79-1.98 (m, 1 H), 1.51-1.74 (m, 3 H), 1.48 (s, 3 H), 1.40-1.48 (m, 1 H), 0.81 (s, 3 H) |
| 92 | 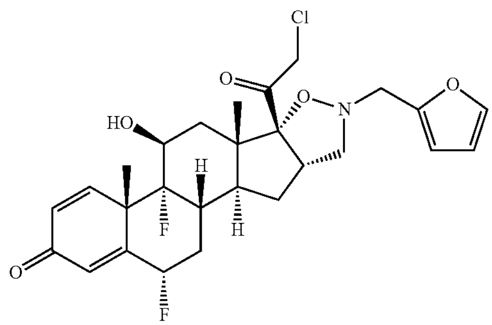 | 73% | LC-MS (ESI POS): 522.2 MH+<br>$^1$H NMR (300 MHz, DMSO-$d_6$) ppm 7.57 (dd, 1 H), 7.27 (dd, 1 H), 6.41 (dd, 1 H), 6.26-6.33 (m, 2 H), 6.07-6.16 (m, 1 H), 5.63 (dddd, 1 H), 5.45 (dd, 1 H), 4.45 (d, 1 H), 4.34 (d, 1 H), 4.11-4.23 (m, 1 H), 3.99 (d, 1 H), 3.86 (d, 1 H), 3.43-3.61 (m, 1 H), 3.32-3.43 (m, 1 H), 2.56-2.73 (m, 1 H), 2.07-2.37 (m, 3 H), 1.85-2.00 (m, 1 H), 1.51-1.71 (m, 3 H), 1.49 (s, 3 H), 1.44 (dd, 1 H), 0.82 (s, 3 H) |
Example 8
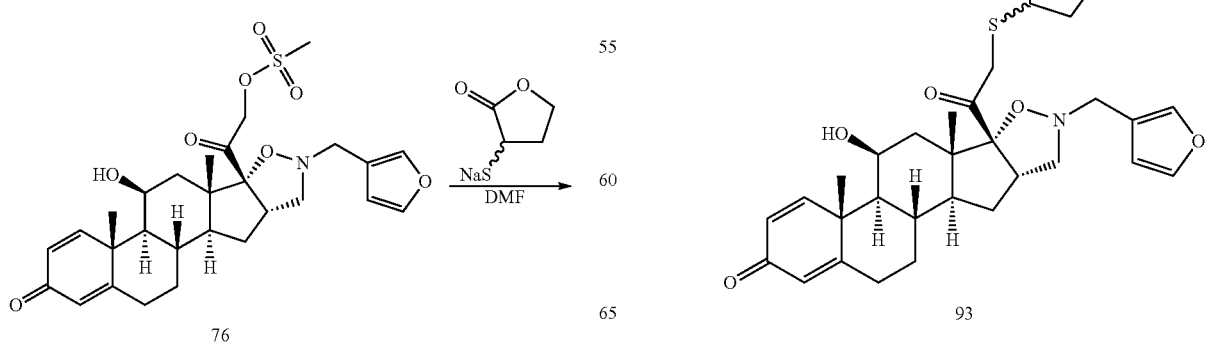

Preparation of (4aR,5S,6aS,6bR,9aS)-8-Furan-3-ylmethyl-5-hydroxy-4-a,6a-dimethyl-6b-[2-(2-oxo-tetrahydro-furan-3-ylsulfanyl)-acetyl]-4-a,4b,5,6,6a,6b,8,9,9a,10,10a,10b,11,12-tetradecahydro-7-oxa-8-aza-pentaleno[2,1-a]phenanthren-2-one (Compound 93)

A solution of 3-mercapto-dihydro-furan-2-one (37 mg, 0.312 mmol) in anhydrous THF (1 ml) was added dropwise to a stirring suspension of NaH (13 mg, 0.325 mmol, 60% suspension in mineral oil) in anhydrous THF (1.5 ml) at 0° C. The resulting solution was stirred at 0° C. for 30 minutes. A solution of compound 76 (170 mg, 0.312 mmol) in anhydrous THF (2 ml) was slowly added dropwise and the mixture was stirred at 0° C. for 2 hours and at RT for 3 hours. The reaction mixture was poured into water (20 ml) and ice, and the aqueous layer was extracted with AcOEt (3×20 ml) and the combined organic extracts were washed with brine, dried (Na$_2$SO$_4$) and concentrated. The crude material was purified by column chromatography on silica gel, in gradient elution from DCM to DCM/AcOEt 25:75, to afford 97 mg of pure compound (55% yield).

$^1$H NMR (300 MHz, CHLOROFORM-d) ppm 7.32-7.43 (m, 2H), 7.18-7.32 (m, 2H), 6.33-6.43 (m, 1H), 6.26-6.34 (m, 1H), 5.82-6.13 (m, 1H), 4.46-4.58 (m, 1H), 4.24-4.69 (m, 2H), 3.31-4.21 (m, 7H), 2.48-2.87 (m, 2H), 2.30-2.49 (m, 1H), 1.86-2.29 (m, 5H), 1.60-1.86 (m, 2H), 1.47 (s, 3H), 1.38-1.63 (m, 1H), 1.25-1.37 (m, 1H), 1.06-1.20 (m, 2H), 0.98 (s, 3H).

LC-MS (ESI POS): 568.11 (MH+)

The compounds listed in Table 6 were prepared as previously described for compound 93:

TABLE 6

| Compound | Structure | Yield | Analytical |
| --- | --- | --- | --- |
| 94 | 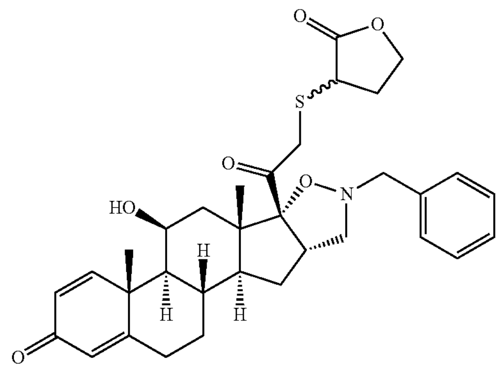 | 10% | LC-MS (ESI POS): 578.19 (MH+)<br>$^1$H NMR (300 MHz, CHLOROFORM-d) ppm 7.18-7.41 (m, 6 H), 6.32 (dd, 1 H), 6.07 (t, 1 H), 4.25-4.54 (m, 3 H), 3.68-3.98 (m, 4 H), 3.31-3.64 (m, 3 H), 2.51-2.76 (m, 2 H), 2.30-2.45 (m, 1 H), 2.03-2.29 (m, 5 H), 1.85-2.01 (m, 2 H), 1.59-1.83 (m, 2 H), 1.48-1.54 (m, 1 H), 1.47 (s, 3 H), 1.06-1.24 (m, 2 H), 0.98 (s, 3 H) |
| 95 | 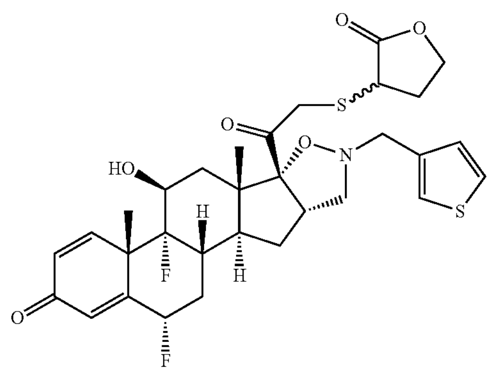 | 30% | LC-MS (ESI POS): 620.06 (MH+)<br>$^1$H NMR (300 MHz, CHLOROFORM-d) ppm 7.22-7.28 (m, 1 H), 7.09-7.21 (m, 2 H), 7.02 (dd, 1 H), 6.46 (s, 1 H), 6.40 (dd, 1 H), 5.40 (dddd, 1 H), 4.14-4.60 (m, 3 H), 3.66-4.13 (m, 4 H), 3.32-3.67 (m, 3 H), 2.59-2.79 (m, 1 H), 2.04-2.59 (m, 6 H), 1.90-2.03 (m, 2 H), 1.59-1.89 (m, 2 H), 1.54 (s, 3 H), 1.47 (dd, 1 H), 0.98 (s, 3 H) |
| 96 | 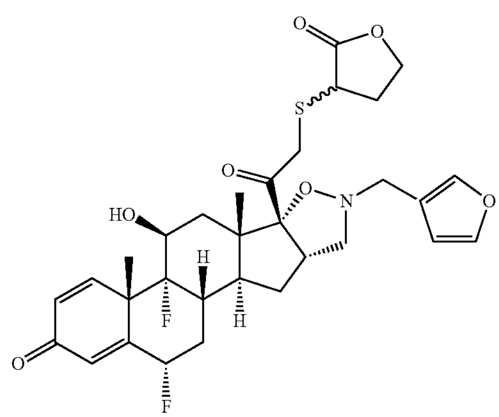 | 76% | LC-MS (ESI POS): 604.07 (MH+)<br>$^1$H NMR (300 MHz, CHLOROFORM-d) ppm 7.32-7.43 (m, 2 H), 7.07-7.18 (m, 1 H), 6.46 (s,1 H), 6.32-6.43 (m, 2 H), 4.99-5.71 (m, 1 H), 4.24-4.62 (m, 3 H), 3.36-4.02 (m, 7 H), 1.96-2.88 (m, 5 H), 1.54 (s, 3 H), 1.37-1.93 (m ,4 H), 1.25-1.40 (m, 1 H), 0.94-1.05 (m, 3 H), 0.73-0.94 (m, 1 H) |

Example 9

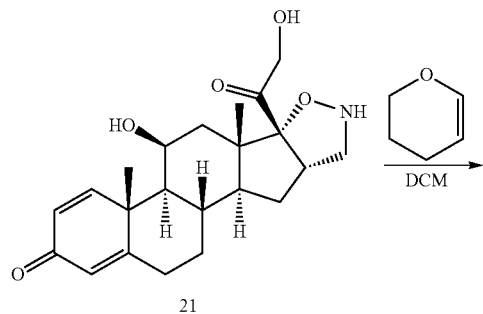

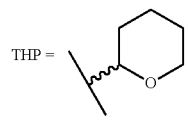

Preparation of (4aR,5S,6aS,6bR,9aS)-5-Hydroxy-4-a,6a-dimethyl-6b-[2-(tetrahydro-pyran-2-yloxy)-acetyl]-4-a,4b,5,6,6a,6b,8,9,9a,10,10a,10,11,12-tetradecahydro-7-oxa-8-aza-pentaleno[2,1-a]phenanthren-2-one (Intermediate 97)

To a solution of (4aR,5S,6aS,6bR,9aS)-5-hydroxy-6b-(2-hydroxy-acetyl)-4-a,6a-dimethyl-4-a,4b,5,6,6a,6b,8,9,9a,10,10a,10b,11,12-tetradecahydro-7-oxa-8-aza-pentaleno[2,1-a]phenanthren-2-one (intermediate 21) (250 mg, 0.64 mmol) in DCM (10 ml), at 0° C. under nitrogen atmosphere, DHP (161 µl, 1.9 mmol) was added, and the reaction mixture was stirred at RT for 1 hour. Solvent was evaporated, and the residue was purified by flash chromatography on silica gel in DCM/AcOEt 80:20, to afford 260 mg of the title compound (86% yield).

LC-MS (ESI POS): 444.2 (MH+)

Example 10

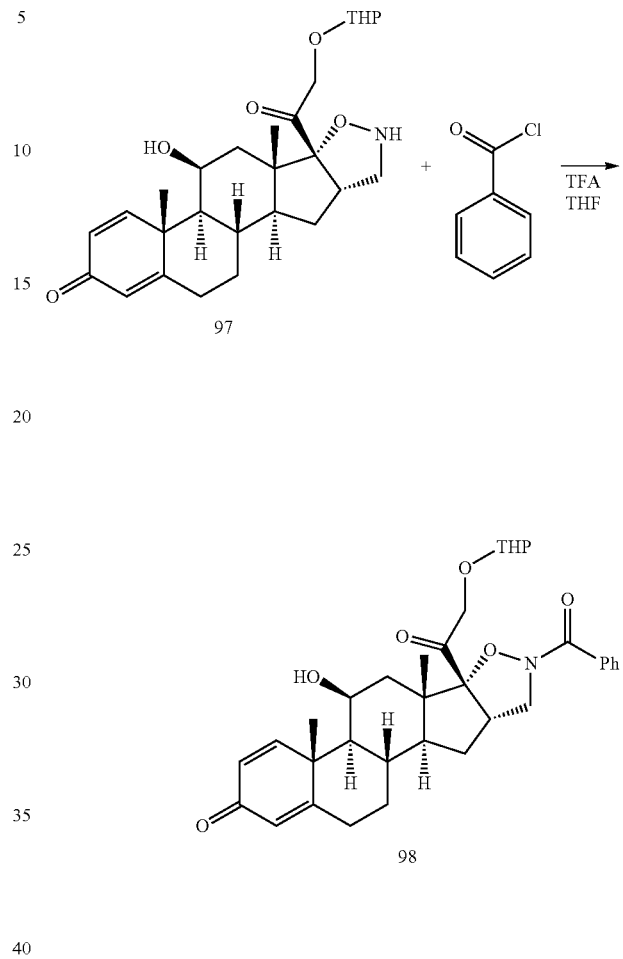

Preparation of (4aR,5S,6aS,6bR,9aS)-8-Benzoyl-5-hydroxy-4-a,6a-dimethyl-6b-[2-(tetrahydro-pyran-2-yloxy)-acetyl]-4-a,4b,5,6,6a,6b,8,9,9a,10,10a,10b,11,12-tetradecahydro-7-oxa-8-aza-pentaleno[2,1-a]phenanthren-2-one (Intermediate 98)

To a solution of intermediate 97 (130 mg, 0.27 mmol) in anhydrous THF (2.7 ml) at 0° C. under nitrogen atmosphere, triethylamine (75 µl, 0.54 mmol) was added, and the mixture stirred for 15 minutes at 0° C. Benzoyl chloride was added (63 µl, 0.54 mmol), and the mixture stirred for further 15 minutes. The mixture was diluted with AcOEt (20 ml), and the organic layer was washed with water and brine, dried (Na$_2$SO$_4$) and concentrated. The crude material was purified by flash chromatography on silica gel in DCM/AcOEt 80:20, to afford 120 mg of the title compound as colorless oil (77% yield).

LC-MS (ESI POS): 576.15 (MH+)

The intermediate listed in Table 7 were prepared as previously described for intermediate 98, reacting intermediate 97 with a suitable acyl chloride.

TABLE 7

| Intermediate | Structure | Yield | Analytical |
|---|---|---|---|
| 99 | 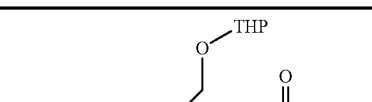 | 71% | LC-MS (ESI POS): 602.1 (MH+) |

Example 11

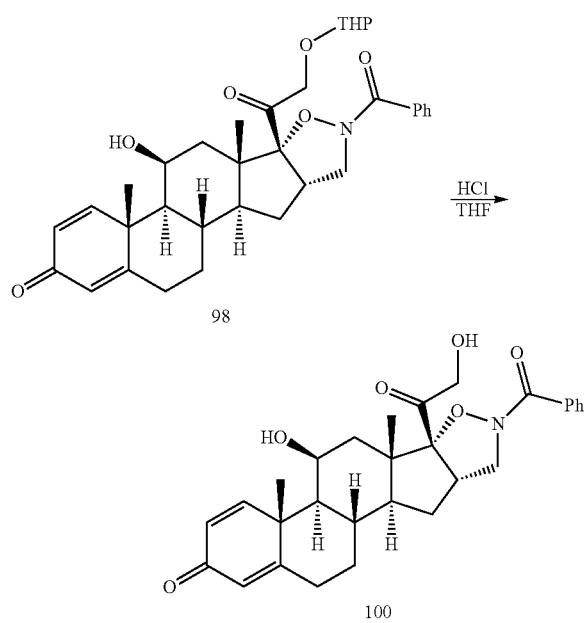

Preparation of (4aR,5S,6aS,6bR,9aS)-8-Benzoyl-5-hydroxy-6b-(2-hydroxy-acetyl)-4-a,6a-dimethyl-4-a, 4b,5,6,6a,6b,8,9,9a,10,10a,10b,11,12-tetradecahydro-7-oxa-8-aza-pentaleno[2,1-a]phenanthren-2-one (Compound 100)

To a solution of intermediate 98 (120 mg, 0.20 mmol) in THF (6 ml), 1N HCl (3 ml) was added, and the mixture was stirred at RT for 14 hours. The mixture was diluted with AcOEt (30 ml), and the organic layer was washed with water and brine, dried ($Na_2SO_4$) and concentrated. Crude was purified by preparative HPLC, to afford 41.3 mg of the title compound (42% yield).

$^1$H NMR (300 MHz, CHLOROFORM-d) ppm 7.57-7.71 (m, 2H), 7.47-7.56 (m, 1H), 7.37-7.46 (m, 2H), 7.30 (d, 1H), 6.39 (dd, 1H), 6.15 (t, 1H), 4.44-4.56 (m, 1H), 4.42 (d, 1H), 4.21 (dd, 1H), 4.16 (d, 1H), 3.73 (td, 1H), 3.53 (dd, 1H), 2.53-2.72 (m, 1H), 2.42 (ddd, 1H), 2.17-2.30 (m, 1H), 2.06-2.17 (m, 1H), 1.96-2.06 (m, 1H), 1.85 (ddd, 1H), 1.67-1.79 (m, 2H), 1.62 (dd, 1H), 1.47 (s, 3H), 1.09-1.33 (m, 1H), 1.04 (dd, 1H), 1.01 (s, 3H).

LC-MS (ESI POS): 492.10 (MH+)

Compound 101 was prepared as previously described for compound 100:

TABLE 8

| Compound | Structure | Yield | Analytical |
|---|---|---|---|
| 101 | 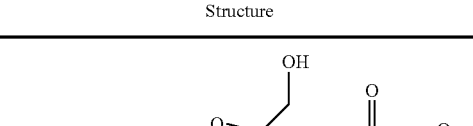 | 55% | LC-MS (ESI POS): 518.05 (MH+)<br>$^1$H NMR (300 MHz, DMSO-d6) ppm 7.92 (d, 1 H), 7.27 (dd, 1 H), 7.19 (d, 1 H), 6.67 (dd, 1 H), 6.29 (dd, 1 H), 6.11 (s, 1 H), 5.52-5.57 (m, 1 H), 5.44-5.83 (m, 1 H), 5.03 (t, 1 H), 4.48 (d, 1 H), 4.06-4.34 (m, 3 H), 3.58-3.75 (m, 1 H), 3.52 (dd, 1 H), 2.60-2.80 (m, 1 H), 1.97-2.26 (m, 3 H), 1.67-1.91 (m, 2 H), 1.51-1.66 (m, 2 H), 1.49 (s, 3 H), 0.92 (s, 3 H) |

Example 12

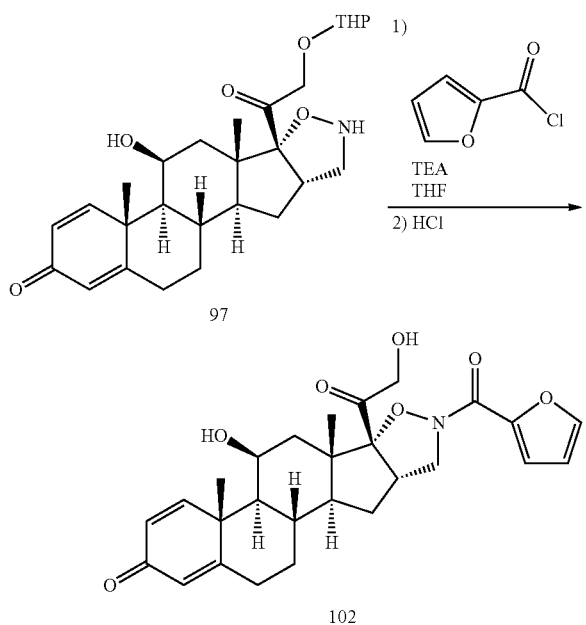

Preparation of (4aR,5S,6aS,6bR,9aS)-8-(Furan-2-carbonyl)-5-hydroxy-6b-(2-hydroxy-acetyl)-4-a,6a-dimethyl-4-a,4b,5,6,6a,6b,8,9,9a,10,10a,10b,11,12-tetradecahydro-7-oxa-8-aza-pentaleno[2,1-a]phenanthren-2-one (Compound 102)

To a solution of intermediate 97 and triethylamine (117 ml, 0.84 mmol), in dry THF, under nitrogen atmosphere at 0° C., 2-furoyl chloride (76 µl, 0.77 mmol) was added, and the reaction mixture was stirred for 5 minutes. The solvent was removed under vacuum, and the residue was dissolved in THF (2 ml), acetonitrile (2 ml) and water (10 ml). 1 N HCl was added to this mixture, and it was stirred at RT for 30 minutes. DCM (15 ml) was added, the phases were separated, and the aqueous layer was extracted with DCM (2×15 ml). The combined organic layers were dried ($Na_2SO_4$) and concentrated. The crude material was purified by preparative HPLC to afford 40 mg of the title compound (11% yield).

$^1$H NMR 1H NMR (300 MHz, DMSO-d6) ppm 7.90 (dd, 1H), 7.31 (d, 1H), 7.20 (dd, 1H), 6.67 (dd, 1H), 6.16 (dd, 1H), 5.91 (s, 1H), 4.80 (br. s., 1H), 4.45 (d, 1H), 4.27-4.38 (m, 1H), 4.20 (dd, 1H), 4.19 (d, 1H), 3.53-3.67 (m, 1H), 3.46 (dd, 1H), 2.53-2.61 (m, 1H), 2.22-2.39 (m, 2H), 1.94-2.17 (m, 2H), 1.82-1.92 (m, 2H), 1.50-1.82 (m, 3H), 1.39 (s, 3H), 0.99-1.15 (m, 1H), 0.92-1.00 (m, 1H), 0.92 (s, 3H).

LC-MS (ESI POS): 482.00 (MH+)

The compounds listed in Table 9 were prepared as previously described for compound 102:

TABLE 9

| Compound | Structure | Yield | Analytical |
|---|---|---|---|
| 103 | (structure) | 12% | LC-MS (ESI POS): 498.08 (MH+)<br>$^1$H NMR (300 MHz, DMSO-d6) ppm 7.89 (dd, 1 H), 7.80 (dd, 1 H), 7.30 (d, 1 H), 7.19 (dd, 1 H), 6.15 (dd, 1 H), 5.91 (s, 1 H), 4.81 (br. s, 1 H), 4.37 (d, 1 H), 4.27-4.37 (m, 1 H), 4.20 (d, 1 H), 4.11 (dd, 1 H), 3.48-3.72 (m, 2 H), 2.55-2.67 (m ,1 H), 2.21-2.39 (m, 1 H), 1.84-2.17 (m, 5 H), 1.53-1.84 (m, 3 H), 1.38 (s, 3 H), 0.93 (s, 3 H), 0.91 (dd, 1 H) |
| 104 | (structure) | 15% | LC-MS (ESI POS): 498.14 (MH+)<br>$^1$H NMR (300 MHz, DMSO-d6) ppm 8.15 (dd, 1 H), 7.57 (dd, 1 H), 7.39 (dd, 1 H), 7.30 (d, 1 H), 6.17 (dd, 1 H), 5.92 (s, 1 H), 4.77 (br. s, 1 H), 4.20-4.40 (m, 2 H), 3.97-4.19 (m, 2 H), 3.45-3.64 (m, 2 H), 2.54-2.61 (m, 1 H), 2.28-2.43 (m, 1 H), 1.91-2.16 (m, 2 H), 1.51-1.84 (m, 5 H), 1.38 (s, 3 H), 0.94-1.14 (m, 1 H), 0.90 (s, 3 H), 0.87 (dd, 1 H) |
| 105 | (structure) | 8% | LC-MS (ESI POS): 506.23 (MH+)<br>$^1$H NMR (300 MHz, CHLOROFORM-d) ppm 7.10-7.39 (m, 6 H), 6.36 (dd, 1 H), 6.09 (t, 1 H), 4.35-4.63 (m, 2 H), 4.26 (d, 1 H), 3.81-3.97 (m, 1 H), 3.44-3.81 (m, 4 H), 2.44-2.66 (m, 1 H), 2.26-2.42 (m, 1 H), 2.05-2.18 (m, 2 H), 1.81-2.04 (m, 2 H), 1.64 (dd, 2 H), 1.49-1.59 (m, 2 H), 1.43 (s, 3 H), 1.01 (s, 3 H), 0.72-0.97 (m, 1 H) |

Example 13

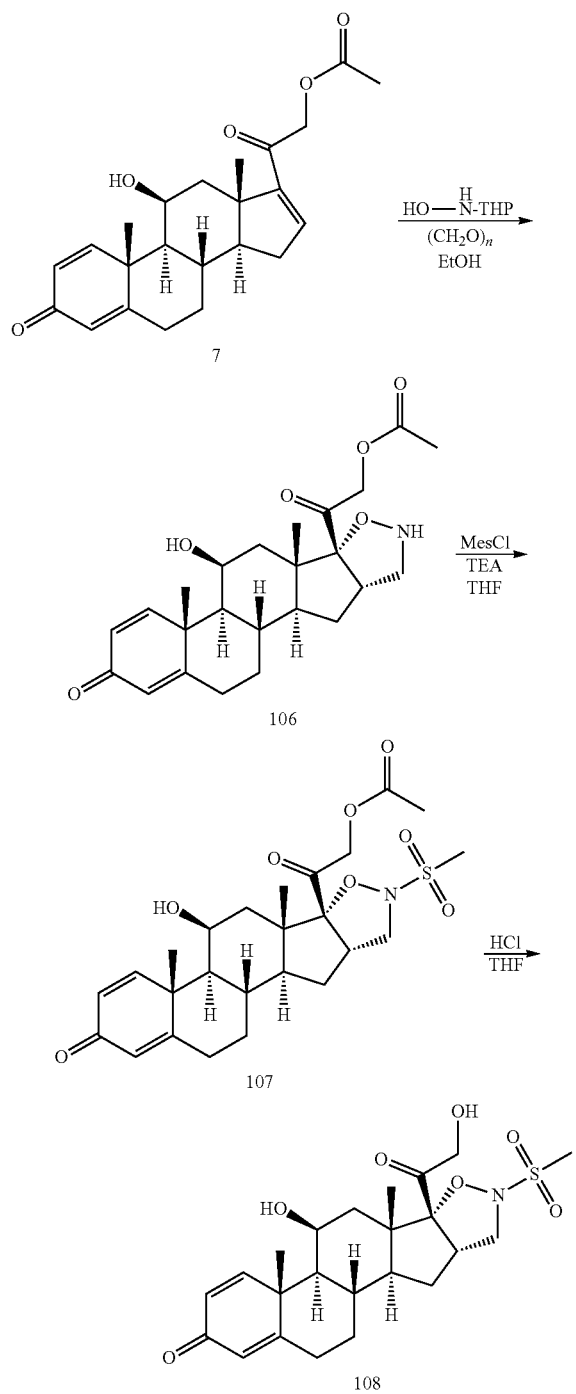

Preparation of acetic acid 2-((4aR,5S,6aS,6bR,9aS)-5-hydroxy-4-a,6a-dimethyl-2-oxo-2,4-a,4b,5,6,6a,8,9,9a,10,10a,10b,11,12-tetradecahydro-7-oxa-8-aza-pentaleno[2,1-a]phenanthren-6b-yl)-2-oxo-ethyl ester (Compound 106)

The title compound was obtained in 55% yield, starting from intermediate 7, as previously described for compound 9 (Example 3).

LC-MS (ESI POS): 430.3 (MH+)

Preparation of acetic acid 2-((4aR,5S,6aS,6bR,9aS)-5-hydroxy-8-methanesulfonyl-4-a,6a-dimethyl-2-oxo-2,4-a,4b,5,6,6a,8,9,9a,10,10a,10,11,12-tetradecahydro-7-oxa-8-aza-pentaleno[2,1-a]phenanthren-6b-yl)-2-oxo-ethyl ester (Compound 107)

Compound 106 (120 mg, 0.28 mmol) was dissolved in anhydrous DCM (5 ml) under nitrogen atmosphere. Triethylamine (75 µl, 0.54 mmol) and methanesulfonyl chloride (75 µl, 0.54 mmol) were added, and the reaction mixture was stirred at RT for 3 days. The mixture was diluted with DCM (20 ml), and the organic phase was washed with water, dried (Na₂SO₄) and concentrated. The crude material was purified by flash chromatography on silica gel, in gradient elution from DCM/AcOEt 90:10 to DCM/AcOEt 50:50, to afford 74 mg of pure compound (52% yield).

LC-MS (ESI POS): 508.3 (MH+)

Preparation of (4aR,5S,6aS,6bR,9aS)-5-Hydroxy-6b-(2-hydroxy-acetyl)-8-methanesulfonyl-4-a,6a-dimethyl 4a,4b,5,6,6a,6b,8,9,9a,10,10a,10b,11,12-tetradecahydro-7-oxa-8-aza-pentaleno[2,1-a]phenanthren-2-one (Compound 108)

To a solution of acetic acid 2-((4aR,5S,6aS,6bR,9aS)-5-hydroxy-8-methanesulfonyl-4-a,6a-dimethyl-2-oxo-2,4-a,4b,5,6,6a,8,9,9a,10,10a,10b,11,12-tetradecahydro-7-oxa-8-aza-pentaleno[2,1-a]phenanthren-6b-yl)-2-oxo-ethyl ester (compound 107) (74 mg, 0.16 mmol) in degassed methanol (5 ml) and water (5 ml), at 0° C. under nitrogen atmosphere, 1 N NaOH (180 µl) was added, and the reaction mixture was stirred at 0° C. for 10 minutes. The reaction mixture was acidified to pH 2, concentrated, and the residue was purified by preparative LC-MS to afford 11.5 mg of the title compound (17% yield).

$^1$H NMR (300 MHz, CHLOROFORM-d): ppm 7.26 (d, 1H), 6.33 (dd, 1H), 6.08 (t, 1H), 4.72 (d, 1H), 4.54 (q, 1H), 4.23 (d, 1H), 4.03 (dd, 1H), 3.78 (td, 1H), 3.06 (s, 3H), 3.00 (dd, 1H), 2.51-2.71 (m, 1H), 2.39 (ddd, 1H), 2.17-2.31 (m, 1H), 2.01-2.17 (m, 3H), 1.77-1.95 (m, 1H), 1.58-1.76 (m, 2H), 1.47 (s, 3H), 1.09-1.32 (m, 2H), 1.01 (s, 3H)

LC-MS (ESI POS): 466.09 (MH+)

Example 14

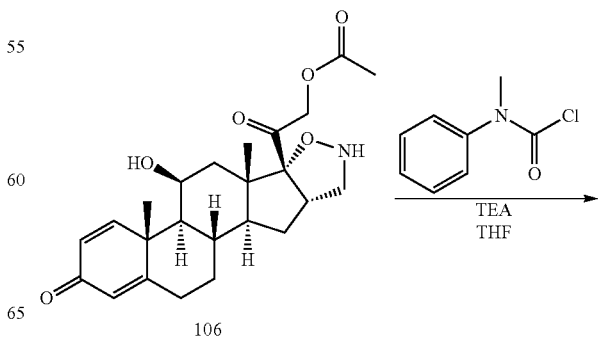

-continued

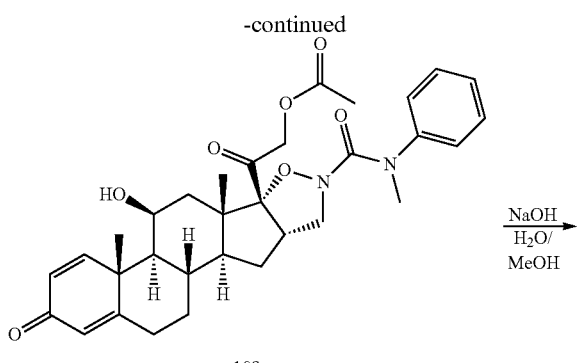

109

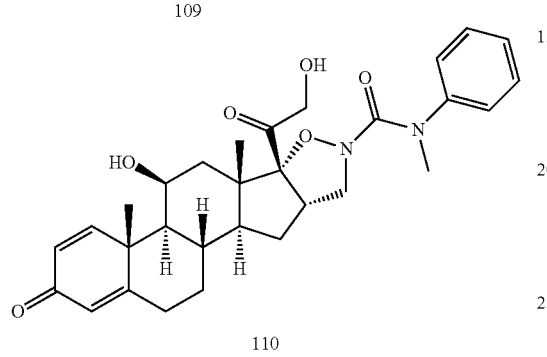

110

Preparation of acetic acid 2-[(4aR,5S,6aS,6bR,9aS)-5-hydroxy-4-a,6a-dimethyl-8-(methyl-phenyl-carbamoyl)-2-oxo-2,4-a,4b,5,6,6a,8,9,9a,10,10a,10b,11,12-tetradecahydro-7-oxa-8-aza-pentaleno[2,1-a]phenanthren-6b-yl]-2-oxo-ethyl ester (Compound 109)

Compound 106 (200 mg, 0.50 mmol) was dissolved in anhydrous DCM (7 ml) under nitrogen atmosphere. Triethylamine (71 μl, 0.51 mmol) and N-Methyl-N-phenylcarbamoyl chloride (87 mg, 0.51 mmol) were added and, the reaction mixture was stirred at 0° C. for 3 hours and at RT for 3 days. The mixture was diluted with water (15 ml), and 1 N HCl was added. The aqueous layer was extracted with DCM (3×20 ml). The combined organic layers were dried ($Na_2SO_4$) and concentrated. The crude material was purified by preparative HPLC, to afford 66 mg of pure compound (23% yield).

LC-MS (ESI POS): 563.7 (MH+)

Preparation of (4aR,5S,6aS,6bR,9aS)-5-Hydroxy-6b-(2-hydroxy-acetyl)-4-a,6a-dimethyl-2-oxo-2,4-a,4b,5,6,6a,6b,9,9a,10,10a,10b,11,12-tetradecahydro-7-oxa-8-aza-pentaleno[2,1-a]phenanthrene-8-carboxylic acid methyl-phenyl-amide (Compound 110)

To a solution of compound 109 (66 mg, 0.12 mmol) in degassed methanol (1.5 ml) and water (1.5 ml), at 0° C. under nitrogen atmosphere, 1 N NaOH (117 μl) was added, and the reaction mixture was stirred at 0° C. for 10 minutes. The reaction mixture was acidified to pH 2, concentrated, and the residue was purified by preparative LC-MS to afford 21 mg of the title compound (33% yield).

$^1$H NMR (300 MHz, DMSO-$d_6$) ppm 7.25-7.38 (m, 3H), 7.17-7.25 (m, 2H), 7.06-7.17 (m, 1H), 6.20 (dd, 1H), 5.94 (s, 1H), 4.64 (br. s., 1H), 4.36 (d, 1H), 4.04-4.25 (m, 1H), 3.89 (d, 1H), 3.65 (dd, 1H), 3.40-3.46 (m, 1H), 3.14 (s, 3H), 2.98 (dd, 1H), 2.53-2.65 (m, 1H), 2.20-2.35 (m, 1H), 1.84-2.13 (m, 2H), 1.47-1.69 (m, 2H), 1.37-1.47 (m, 1H), 1.35 (s, 3H), 1.13-1.37 (m, 3H), 0.92-1.12 (m, 1H), 0.84 (dd, 1H), 0.78 (s, 3H).

LC-MS (ESI POS): 521.24 (MH+)

Example 15

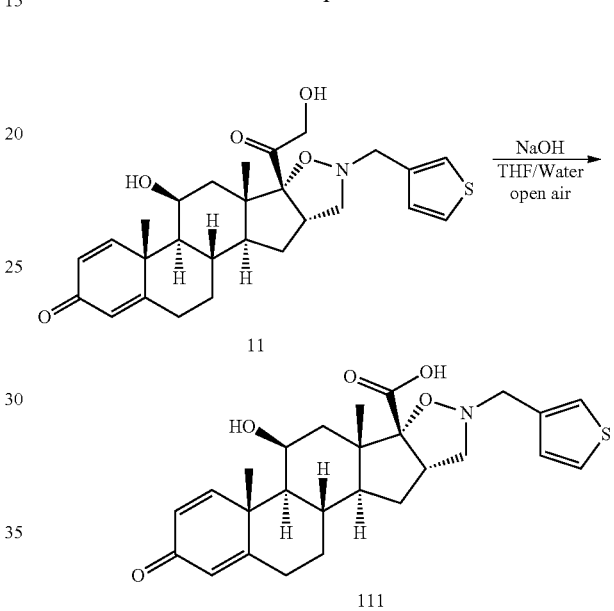

Preparation of (4aR,5S,6aS,6bR,9aS)-5-Hydroxy-4-a,6a-dimethyl-2-oxo-8-thiophen-3-ylmethyl-2,4-a,4b,5,6,6a,8,9,9a,10,10a,10b,11,12-tetradecahydro-7-oxa-8-aza-pentaleno[2,1-a]phenanthrene-6b-carboxylic acid (Compound 111)

To a solution of 11 (202 mg, 0.418 mmol) in THF (3 ml) and water (1 ml), 1 N NaOH (836 μl, 0.836 mmol) was added, and the reaction mixture was stirred at RT in an open vessel for 24 hours. The reaction mixture was poured into 2 N HCl and ice (30 ml), and the aqueous layer was extracted with AcOEt (3×30 ml). The combined organic extracts were washed with brine, dried over anhydrous sodium sulphate and concentrated to give 202 mg of crude material (quantitative yield) which was used as such without further purification.

1H NMR (300 MHz, DMSO-d6) ppm 7.42 (dd, 1H), 7.31-7.35 (m, 1H), 7.31 (d, 1H), 7.04 (dd, 1H), 6.16 (dd, 1H), 5.92 (s, 1H), 4.20-4.35 (m, 1H), 3.89 (br. s., 2H), 3.31-3.58 (m, 2H), 2.53-2.60 (m, 1H), 2.22-2.37 (m, 1H), 1.93-2.20 (m, 3H), 1.81 (d, 1H), 1.49-1.71 (m, 3H), 1.35-1.48 (m, 1H), 1.39 (s, 3H), 0.97-1.15 (m, 1H), 0.96 (s, 3H), 0.91 (dd, 1H).

LC-MS (ESI POS): 470.13 (MH+)

Compounds listed in Table 10 were prepared as previously described for compound 111:

TABLE 10
| Compound | Structure | Analytical |
|---|---|---|
| 112 | 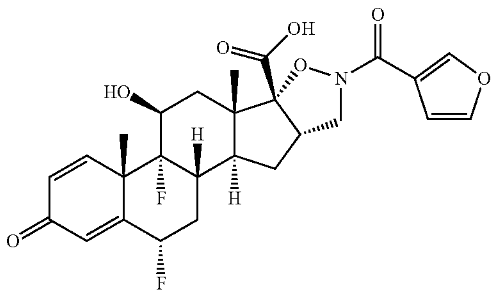 | LC-MS (ESI POS): 490.2 (MH+) |
| 113 | 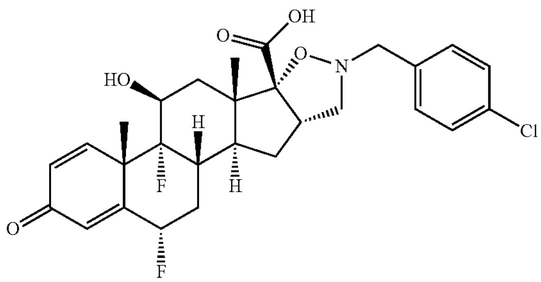 | LC-MS (ESI POS): 548.3 (MH+) |
| 114 | 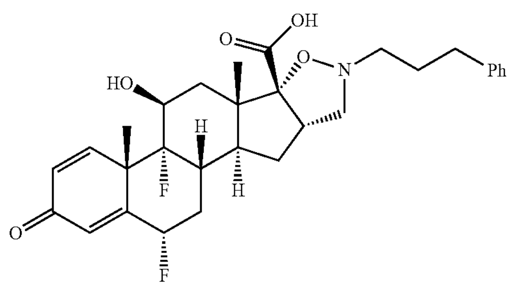 | LC-MS (ESI POS): 528.3 (MH+) |
| 115 | 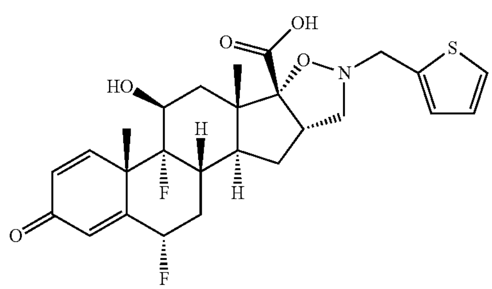 | LC-MS (ESI POS): 506.0 (MH+) |
Example 16
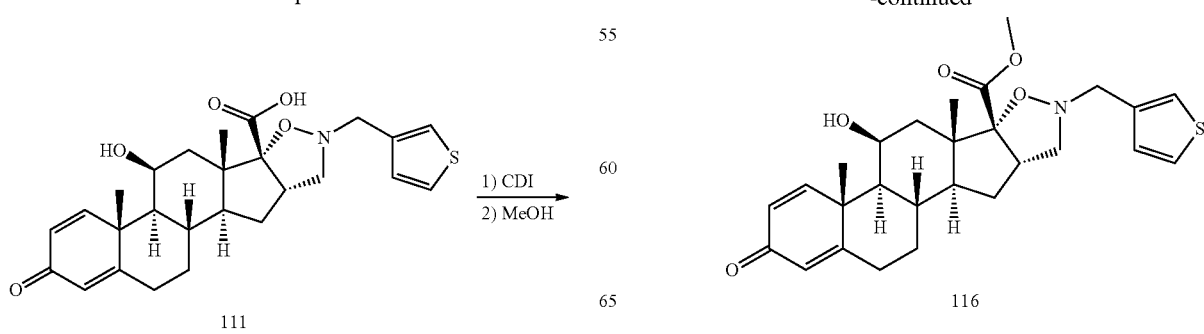

Preparation of (4aR,5S,6aS,6bR,9aS)-5-Hydroxy-4-a,6a-dimethyl-2-oxo-8-thiophen-3-ylmethyl-2,4-a,4b,5,6,6a,8,9,9a,10,10a,10b,11,12-tetradecahydro-7-oxa-8-aza-pentaleno[2,1-a]phenanthrene-6b-carboxylic acid methyl ester (Compound 116)

Under nitrogen atmosphere, compound 111 (110 mg, 0.23 mmol) was suspended in anhydrous THF (25 ml), CDI (65 mg, 0.39 mmol) was added, and the mixture was stirred at 60° C. for 3 hours. Methanol (5 ml) was added, and the reaction mixture was stirred at RT overnight. The solvent was evaporated, and the crude material was purified by preparative HPLC, to afford 41 mg of pure compound (37% yield).

$^1$H NMR (300 MHz, DMSO-d6) ppm 7.42 (dd, 1H), 7.31 (d, 1H), 7.27-7.30 (m, 1H), 7.01 (dd, 1H), 6.16 (dd, 1H), 5.92 (s, 1H), 4.18-4.36 (m, 1H), 3.88 (s, 2H), 3.66 (s, 3H), 3.38-3.51 (m, 2H), 2.53-2.61 (m, 1H), 2.21-2.37 (m, 1H), 1.92-2.18 (m, 3H), 1.69-1.84 (m, 1H), 1.46-1.68 (m, 3H), 1.39 (s, 3H), 1.32-1.46 (m, 1H), 0.97-1.14 (m, 1H), 0.90 (s, 3H), 0.86-0.96 (m, 1H).

LC-MS (ESI POS): 484.28 (MH+)

Example 17

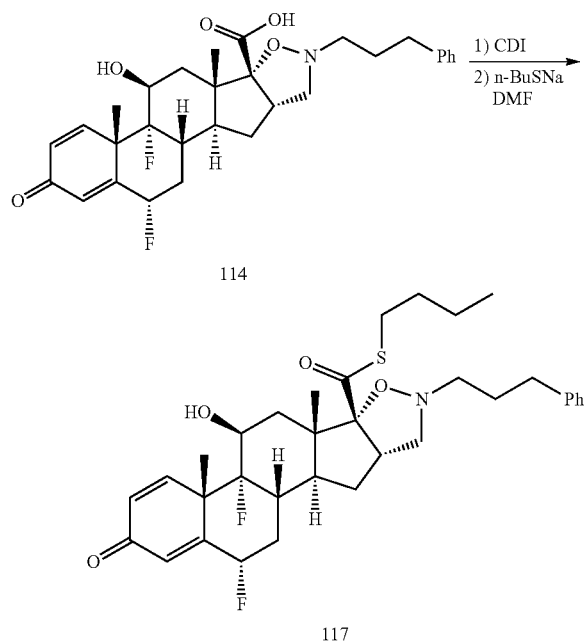

Preparation of (4aS,4bR,5S,6aS,6bR,9aS,10aS,10bS,12S)-4-b,12-Difluoro-5-hydroxy-4-a,6a-dimethyl-2-oxo-8-(3-phenyl-propyl)-2,4-a,4b,5,6,6a,8,9,9a,10,10a,10b,11,12-tetradecahydro-7-oxa-8-aza-pentaleno[2,1-a]phenanthrene-6b-carbothoic acid S-butyl ester (Compound 117)

To a solution of compound 114 (100 mg, 0.190 mmol) in anhydrous DMF (2 ml), under nitrogen atmosphere, carbonyldiimidazole (CDI) (61.5 mg, 0.379 mmol) was added, and the reaction mixture was stirred at RT for 1.5 hours and at 60° C. for 30 minutes. Then, a solution of butyl mercaptan (0.041 ml, 0.379 mmol) and sodium hydride (16.68 mg, 0.417 mmol) in anhydrous DMF (3 ml) was slowly dropped and the reaction mixture was stirred at RT for 1.5 hours. The reaction mixture was poured into water and ice (50 ml), and the aqueous layer was extracted with AcOEt (3×50 ml). The combined organic extracts were washed with water, brine, dried over anhydrous sodium sulphate, and concentrated. The crude material was purified by flash SiO2 cartridge in gradient elution from DCM to DCM/AcOEt 88:12, to afford 66 mg of the title compound (58.1% yield).

$^1$H NMR (300 MHz, DMSO-d$_6$) ppm 7.08-7.33 (m, 6H), 6.29 (dd, 1H), 6.11 (s, 1H), 5.50-5.78 (m, 1H), 5.47 (d, 1H), 4.06-4.30 (m, 1H), 3.44-3.64 (m, 1H), 3.32-3.44 (m, 1H), 2.79 (td, 2H), 2.54-2.74 (m, 6H), 2.18-2.32 (m, 1H), 1.94-2.18 (m, 3H), 1.70-1.94 (m, 4H), 1.53-1.68 (m, 1H), 1.49 (s, 3H), 1.40-1.48 (m, 2H), 1.25-1.39 (m, 2H), 0.87 (s, 3H), 0.86 (t, 3H).

LC-MS (ESI POS): 600.4 (MH+)
$[\alpha]_D^{25}$=+150.2° (c=0.50, CHCl$_3$)

Example 18

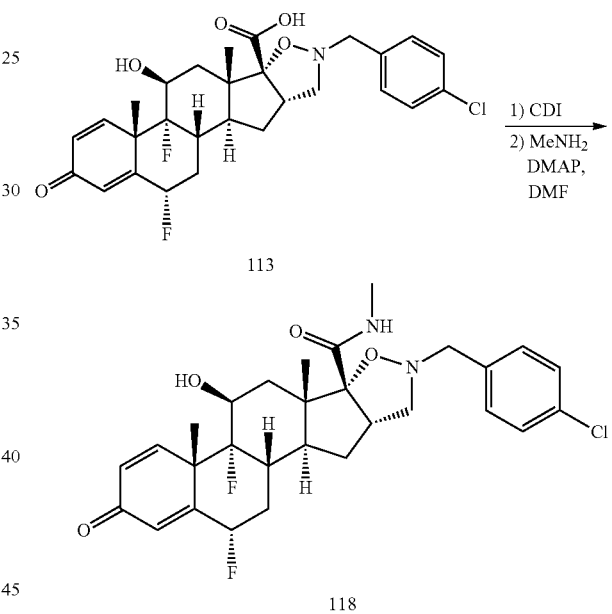

Preparation of (4aS,4bR,5S,6aS,6bR,9aS,10aS,10bS,12S)-8-(4-Chloro-benzyl)-4-b,12-difluoro-5-hydroxy-4-a,6a-dimethyl-2-oxo-2,4-a,4b,5,6,6a,8,9,9a,10,10a,10b,11,12-tetradecahydro-7-oxa-8-aza-pentaleno[2,1-a]phenanthrene-6b-carboxylic acid methyl amide (Compound 118)

To a solution of compound 113 (200 mg, 0.375 mmol) in dry DMF (5 ml), under nitrogen atmosphere, CDI (66.8 mg, 0.412 mmol) was added, and the mixture was stirred at 50° C. for 1 hour. The reaction mixture was cooled to room temperature, and a 2 M solution of methylamine (0.749 ml, 1.498 mmol) in THF was added, followed by DMAP (45.8 mg, 0.375 mmol). The reaction mixture was stirred at 50° C. for 4 hours: as some carboxylic acid was still present, another addition of a 2 M solution of methylamine (1.5 ml, 3.00 mmol) was done and the reaction mixture was heated at 50° C. overnight. The reaction mixture was cooled, poured into 100 ml of water and extracted with AcOEt (3×70 ml). The combined organic extracts were washed with brine, dried over sodium sulphate, and concentrated. The crude material (240 mg) was dissolved in MeOH, and the residual carboxylic acid was removed on a PS—HCO3- cartridge, obtaining 219 mg of crude. Purification via chromatographic column over silica gel (DCM/AcOEt 1/1) affords 150 mg of the title compound (73% yield).

$^1$H NMR (300 MHz, DMSO-d$_6$) ppm 7.27-7.46 (m, 4H), 7.24 (dd, 1H), 7.10 (q, 1H), 6.29 (dd, 1H), 6.11 (s, 1H), 5.50-5.79 (m, 1H), 5.38 (dd, 1H), 4.05-4.17 (m, 1H), 3.91 (d, 1H), 3.83 (d, 1H), 3.46-3.62 (m, 1H), 3.34-3.46 (m, 1H), 2.61 (d, 3H), 2.54-2.59 (m, 1H), 2.18-2.33 (m, 1H), 1.97-2.17 (m, 1H), 1.71-1.86 (m, 1H), 1.51-1.65 (m, 3H), 1.49 (s, 3H), 1.46-1.52 (m, 1H), 1.39 (dd, 1H), 0.88 (s, 3H)

LC-MS (ESI POS): 547.19 MH+

$[\alpha]_D^{25}$=+283.3, (c=0.21, CHCl$_3$)

The compounds listed in Table 11 were prepared as previously described for compound 118, utilising the suitable alcohol, thiol, or amine (or the corresponding hydrochloride salt of the amine):

TABLE 11

| Compound | Structure | Yield | Analytical |
|---|---|---|---|
| 119 | 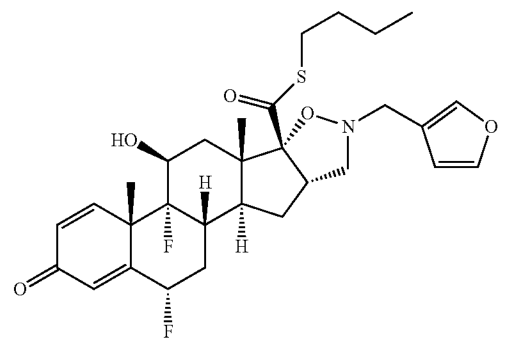 | 79% | LC-MS (ESI POS): 562.13 (MH+)<br>$[\alpha]_D^{25}$ = +134.5° (c = 0.57, CHCl$_3$)<br>$^1$H NMR (300 MHz, DMSO-d$_6$) ppm 7.44-7.61 (m, 2 H), 7.25 (dd, 1 H), 6.41 (dd, 1 H), 6.30 (dd, 1 H), 6.11 (s, 1 H), 5.50-5.82 (m, 1 H), 5.47 (dd, 1 H), 4.11-4.28 (m, 1 H), 3.79 (d, 1 H), 3.72 (d, 1 H), 3.34-3.56 (m, 1 H), 2.65-2.88 (m, 2 H), 2.17-2.30 (m, 2 H), 2.02-2.17 (m, 2 H), 1.83-1.95 (m, 1 H), 1.70-1.83 (m, 1 H), 1.50-1.69 (m, 3 H), 1.49 (s, 3 H), 1.28-1.47 (m, 4 H), 0.88 (t, 3 H), 0.86 (s, 3 H) |
| 120 | 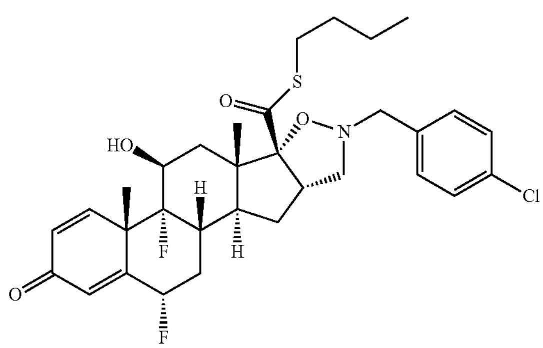 | 20% | LC-MS (ESI POS): 606.04 (MH+)<br>$^1$H NMR (300 MHz, DMSO-d$_6$) ppm 7.29-7.41 (m, 4 H) 7.24 (dd, 1 H) 6.29 (dd, 1 H) 6.12 (s, 1 H) 5.50-5.79 (m, 1 H) 5.40-5.50 (m, 1 H) 4.08-4.23 (m, 1 H) 3.96 (d, 1 H) 3.80 (d, 1 H) 3.34-3.60 (m, 2 H) 2.61-2.82 (m, 3 H) 2.02-2.35 (m, 3 H) 1.77-1.87 (m, 1 H) 1.41-1.74 (m, 9 H) 1.22-1.39 (m, 2 H) 0.80-0.93 (m, 6 H) |
| 121 | 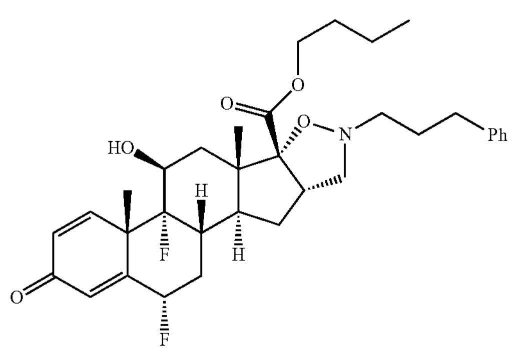 | 43% | LC-MS (ESI POS): 584.03 (MH+)<br>$^1$H NMR (300 MHz, DMSO-d$_6$) ppm 7.00-7.34 (m, 6 H), 6.29 (dd, 1 H), 6.11 (s, 1 H), 5.50-5.84 (m, 1 H), 5.45 (d, 1 H), 4.13-4.23 (m, 1 H), 4.06 (t, 2 H), 3.39-3.51 (m, 1 H), 3.50 (q, 1 H), 2.54-2.71 (m, 4 H), 2.20-2.33 (m, 1 H), 1.81-2.18 (m, 3 H), 1.51-1.79 (m, 7 H), 1.49 (s, 3 H), 1.22-1.45 (m, 4 H), 0.90 (s, 3 H), 0.86 (t, 3 H) |

TABLE 11-continued

| Compound | Structure | Yield | Analytical |
|---|---|---|---|
| 122 | 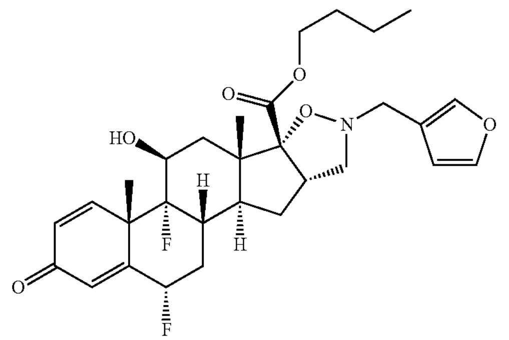 | 28% | LC-MS (ESI POS): 546.17 (MH+)<br>$[\alpha]_D^{25}$ = +77.08° (c = 0.50, CHCl$_3$)<br>$^1$H NMR (300 MHz, DMSO-d$_6$) ppm 7.54 (t, 1 H), 7.49 (s, 1 H), 7.26 (dd, 1 H), 6.38 (dd, 1 H), 6.29 (dd, 1 H), 6.11 (s, 1 H), 5.49-5.79 (m, 1 H), 5.46 (dd, 1 H), 4.12-4.25 (m, 1 H), 4.02-4.12 (m, 2 H), 3.60-3.82 (m, 2 H), 3.42-3.59 (m, 2 H), 2.55-2.68 (m, 1 H), 1.82-2.35 (m, 4 H), 1.52-1.80 (m, 4 H), 1.49 (s, 3 H), 1.27-1.47 (m, 4 H), 0.91 (s, 3 H), 0.90 (t, 3 H) |
| 123 | 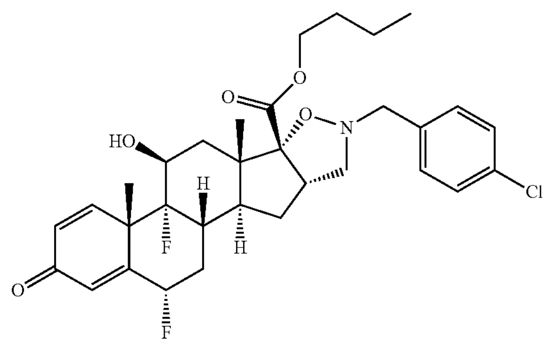 | 20% | LC-MS (ESI POS): 590.14 (MH+)<br>$^1$H NMR (300 MHz, DMSO-d$_6$) ppm 7.10-7.44 (m, 5 H), 6.29 (dd, 1 H), 6.12 (s, 1 H), 5.49-5.82 (m, 1 H), 5.45 (dd, 1 H), 4.10-4.27 (m, 1 H), 4.06 (t, 2 H), 3.84-3.97 (m, 1 H), 3.78 (d, 1 H), 3.37-3.65 (m, 2 H), 2.56-2.69 (m, 1 H), 2.04-2.35 (m, 3 H), 1.74-1.91 (m, 1 H), 1.50-1.74 (m, 4 H), 1.49 (s, 3 H), 1.17-1.46 (m, 4 H), 0.90 (s, 3 H), 0.88 (t, 3 H) |
| 124 | 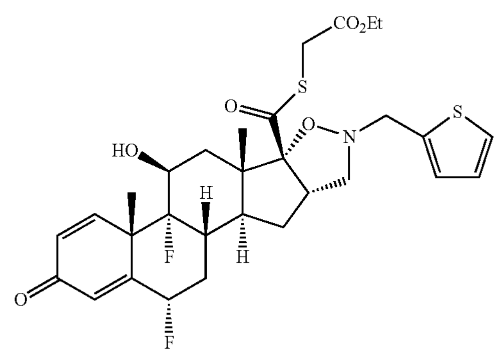 | 33% | LC-MS (ESI POS): 608.2 MH+<br>$[\alpha]_D^{25}$ = +77.89 (c = 0.44, MeOH)<br>$^1$H NMR (300 MHz, DMSO-d$_6$) ppm 7.41 (dd, 1 H), 7.27 (dd, 1 H), 7.00 (dd, 1 H), 6.94 (dd, 1 H), 6.31 (dd, 1 H), 6.12 (s, 1 H), 5.55 (d, 1 H), 5.48-5.79 (m, 1 H), 4.12-4.22 (m, 3 H), 4.01-4.12 (m, 2 H), 3.69 (d, 1 H), 3.63 (d, 1 H), 3.39-3.52 (m, 1 H), 3.34-3.42 (m, 1 H), 2.57-2.69 (m, 1 H), 2.00-2.35 (m, 2 H), 1.86-2.00 (m, 1 H), 1.76 (d, 1 H), 1.53-1.72 (m, 2 H), 1.49 (s, 3 H), 1.35-1.47 (m, 1 H), 1.20 (t, 3 H), 0.88 (s, 3 H) |
| 125 | 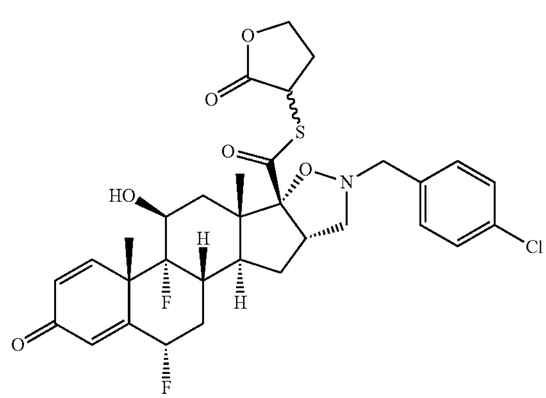 | 48% | LC-MS (ESI POS): 634.2 MH+<br>$^1$H NMR (300 MHz, DMSO-d$_6$) ppm 7.29-7.40 (m, 4 H), 7.24 (d, 1 H), 6.30 (dd, 1 H), 6.12 (s, 1 H), 5.54-5.77 (m, 1 H), 5.54 (d, 1 H), 4.39 (td, 1 H), 4.27-4.35 (m, 1 H), 4.26 (t, 1 H), 4.10-4.19 (m, 1 H), 4.00 (d, 1 H), 3.83 (dd, 1 H), 3.45-3.61 (m, 1 H), 3.32-3.44 (m, 1 H), 2.58-2.70 (m, 2 H), 2.03-2.25 (m, 4 H), 1.52-1.87 (m, 4 H), 1.49 (s, 3 H), 1.39-1.47 (m, 1 H), 0.88 and 0.91 (s, 3 H) |

TABLE 11-continued

| Compound | Structure | Yield | Analytical |
|---|---|---|---|
| 126 | 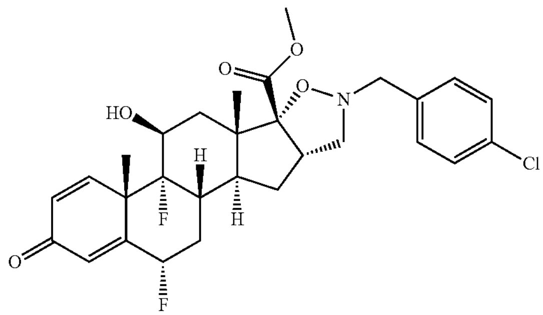 | 48% | LC-MS (ESI POS): 548.2 MH+<br>[α]$_D^{25}$ = +106.2, (c = 0.40, MeOH)<br>$^1$H NMR (300 MHz, DMSO-d$_6$) ppm 7.31-7.40 (m, 2 H), 7.20-7.31 (m, 3 H), 6.29 (dd, 1 H), 6.11 (s, 1 H), 5.49-5.82 (m, 1 H), 5.43 (dd, 1 H), 4.05-4.20 (m, 1 H), 3.85-3.97 (m, 1 H), 3.81 (d, 1 H), 3.67 (s, 3 H), 3.48-3.60 (m, 1 H), 3.36-3.45 (m, 1 H), 2.31-2.45 (m, 1 H), 1.99-2.25 (m, 2 H), 1.53-1.83 (m, 5 H), 1.49 (s, 3 H), 1.36-1.47 (m, 1 H), 0.89 (s, 3 H) |
| 127 | 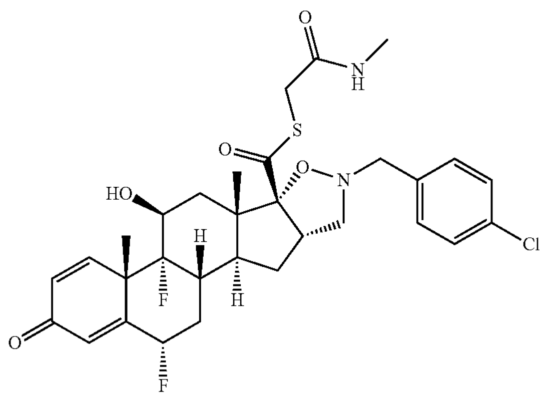 | 22% | LC-MS (ESI POS): 621.21 MH+<br>[α]$_D^{25}$ = +104.8, (c = 0.23, MeOH)<br>$^1$H NMR (300 MHz, CHLOROFORM-d) ppm 7.24-7.33 (m, 4 H), 7.16 (dd, 1 H), 6.46 (s, 1 H), 6.40 (dd, 1 H), 6.15 (br. s, 1 H), 5.41 (dddd, 1 H), 4.40 (d, 1 H), 4.00 (d, 1 H), 3.91 (d, 1 H), 3.50-3.75 (m, 2 H), 3.47 (s, 2 H), 2.79 (d, 3 H), 2.09-2.62 (m, 5 H), 1.65-1.94 (m, 4 H), 1.55 (s, 3 H), 1.50 (dd, 1 H), 0.96 (s, 3 H) |
| 128 | 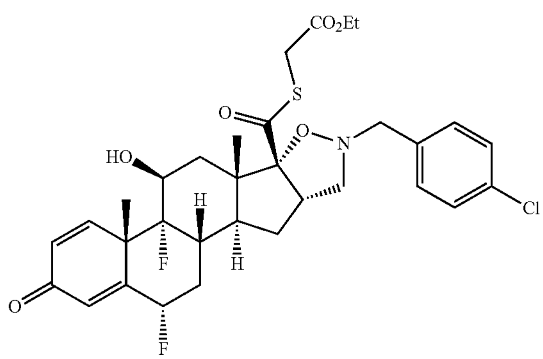 | 40% | LC-MS (ESI POS): 636.23 MH+<br>[α]$_D^{25}$ = +133.0 (c = 0.131, CHCl$_3$)<br>$^1$H NMR (300 MHz, DMSO-d$_6$) ppm 7.29-7.41 (m, 4 H), 7.25 (dd, 1 H), 6.30 (dd, 1 H), 6.12 (s, 1 H), 5.56-5.78 (m, 1 H), 5.54 (d, 1 H), 4.14-4.20 (m, 1 H), 4.10 (qd, 2 H), 3.98 (d, 1 H), 3.84 (d, 1 H), 3.69 (d, 1 H), 3.63 (d, 1 H), 3.43-3.56 (m, 1 H), 3.34-3.42 (m, 1 H), 2.55-2.67 (m, 1 H), 2.00-2.28 (m, 3 H), 1.77-1.90 (m, 1 H), 1.52-1.76 (m, 3 H), 1.49 (s, 3 H), 1.42-1.48 (m, 1 H), 1.20 (t, 3 H), 0.86 (s, 3 H) |
| 129 | 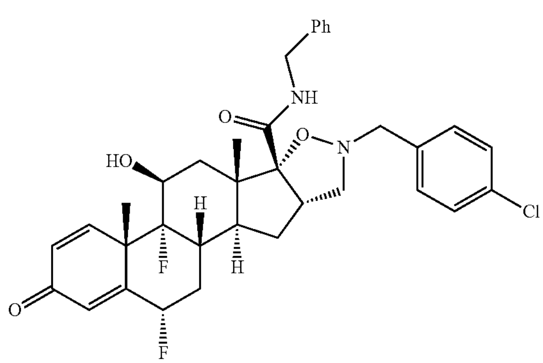 | 22% | LC-MS (ESI POS): 623.2 MH+<br>[α]$_D^{25}$ = +179.0 (c = 0.26, CHCl$_3$)<br>$^1$H NMR (300 MHz, DMSO-d$_6$) ppm 7.64 (br. s, 1 H), 7.11-7.40 (m, 10 H), 6.30 (dd, 1 H), 6.12 (s, 1 H), 5.51-5.77 (m, 1 H), 5.46 (dd, 1 H), 4.31-4.53 (m, 1 H), 4.05-4.24 (m, 2 H), 3.87 (s, 2 H), 3.46-3.58 (m, 1 H), 3.37-3.47 (m, 1 H), 2.56-2.62 (m, 1 H), 2.06-2.32 (m, 2 H), 1.75-1.92 (m, 1 H), 1.52-1.71 (m, 4 H), 1.50 (s, 3 H), 1.35-1.46 (m, 1 H), 0.92 (s, 3 H) |

TABLE 11-continued

| Compound | Structure | Yield | Analytical |
|---|---|---|---|
| 130 | 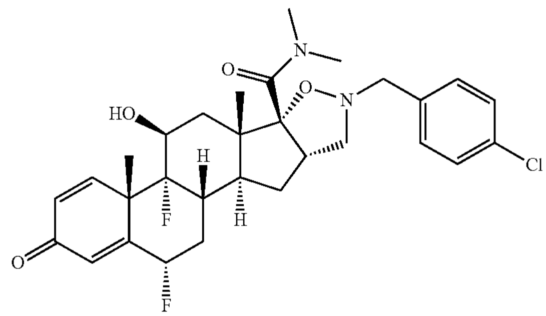 | 61% | LC-MS (ESI POS): 561.2 MH+<br>[α]$_D^{25}$ = +189.7 (c = 0.23, CHCl$_3$)<br>$^1$H NMR (300 MHz, DMSO-d$_6$) ppm 7.33-7.40 (m, 2 H) 7.27-7.32 (m, 2 H) 7.25 (dd, 1 H) 6.29 (dd, 1 H) 6.12 (s, 1 H) 5.46-5.80 (m, 1 H) 5.40 (dd, 1 H) 4.07-4.24 (m, 1 H) 3.78-4.06 (m, 2 H) 3.59-3.79 (m, 1 H) 3.35-3.57 (m, 1 H) 2.77 (s, 3 H) 2.68 (br. s, 3 H) 2.56-2.71 (m, 2 H) 2.06-2.37 (m, 2 H) 1.83-2.01 (m, 1 H) 1.52-1.70 (m, 3 H) 1.49 (s, 3 H) 1.39 (dd, 1 H) 0.89 (s, 3 H) |
| 131 | 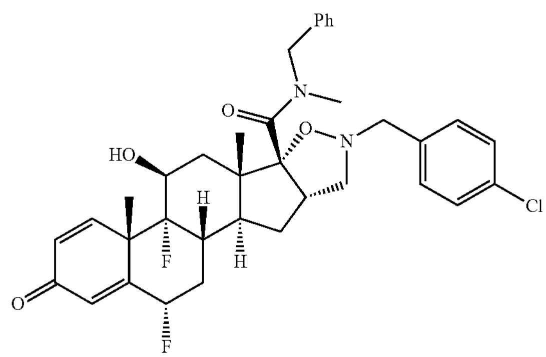 | 54% | LC-MS (ESI POS): 637.34 MH+<br>[α]$_D^{25}$ = +145.1 (c 0.136, CHCl$_3$)<br>$^1$H NMR (300 MHz, DMSO-d6 353K) ppm 7.10-7.46 (m, 10 H) 6.27 (dd, 1 H) 6.10-6.18 (m, 1 H) 5.61 (dddd, 1 H) 5.12-5.25 (m, 1 H) 4.53-4.66 (m, 1 H) 4.36-4.53 (m, 1 H) 4.13-4.27 (m, 1 H) 3.93-4.08 (m, 1 H) 3.85 (d, 1 H) 3.75 (d, 1 H) 3.39 (t, 1 H) 2.74 (s, 3 H) 2.54-2.66 (m, 1 H) 2.16-2.39 (m, 3 H) 2.02 (dt, 1 H) 1.55-1.79 (m, 3 H) 1.53 (s, 3 H) 1.42 (dd, 1 H) 1.01 (s, 3 H) |
| 132 | 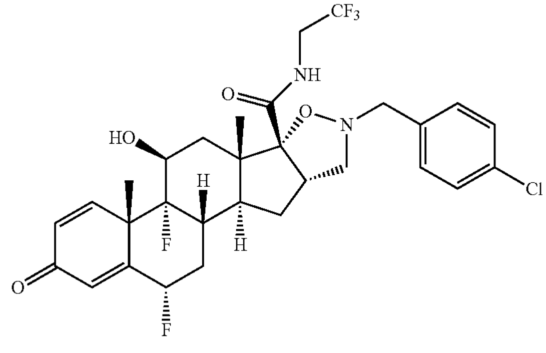 | 56% | LC-MS (ESI POS):615.28 MH+<br>[α]$_D^{25}$ = +134.3 (c = 0.2, MeOH)<br>$^1$H NMR (300 MHz, DMSO-d$_6$) ppm 7.80 (t, 1 H), 7.27-7.38 (m, 4 H), 7.24 (dd, 1 H), 6.30 (dd, 1 H), 6.12 (s, 1 H), 5.52-5.77 (m, 1 H), 5.50 (dd, 1 H), 4.09-4.23 (m, 1 H), 3.78-3.97 (m, 4 H), 3.45-3.60 (m, 1 H), 3.34-3.46 (m, 1 H), 2.55-2.69 (m, 1 H), 2.03-2.41 (m, 3 H), 1.75-1.92 (m, 1 H), 1.50-1.72 (m, 3 H), 1.49 (s, 3 H), 1.41 (dd, 1 H), 0.89 (s, 3 H) |

TABLE 11-continued

| Compound | Structure | Yield | Analytical |
|---|---|---|---|
| 133 | 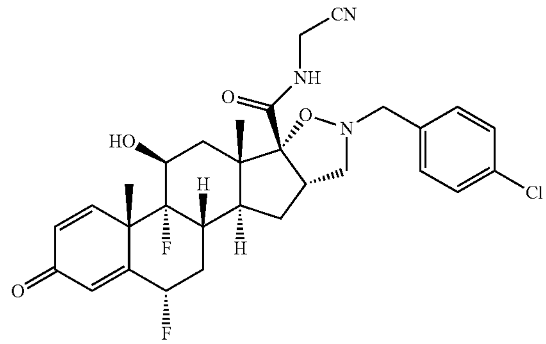 | 60% | LC-MS (ESI POS): 572.37 MH+<br>$[\alpha]_D^{25}$ = +132.7 (c = 0.2, MeOH)<br>$^1$H NMR (300 MHz, DMSO-d$_6$) ppm 8.00 (t, 1 H), 7.33 (m, 4 H), 7.24 (dd, 1 H), 6.29 (dd, 1 H), 6.12 (s, 1 H), 5.51-5.78 (m, 1 H), 5.48 (dd, 1 H), 4.17 (dd, 1 H), 4.08-4.13 (m, 1 H), 4.03 (dd, 1 H), 3.95 (d, 1 H), 3.86 (d, 1 H), 3.48-3.63 (m, 1 H), 3.34-3.49 (m, 1 H), 2.54-2.70 (m, 1 H), 2.17-2.36 (m, 2 H), 2.01-2.17 (m, 1 H), 1.71-1.91 (m, 1 H), 1.54-1.71 (m, 3 H), 1.33-1.52 (m, 1 H), 1.49 (s, 3 H), 0.89 (s, 3 H) |
| 134 | 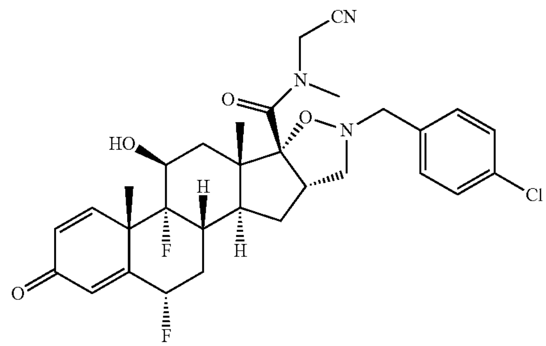 | 23% | LC-MS (ESI POS): 586.36 MH+<br>$[\alpha]_D^{25}$ = +149.7 (c = 0.2, MeOH)<br>$^1$H NMR (300 MHz, DMSO-d6 353K) ppm 7.28-7.37 (m, 4 H), 7.25 (dd, 1 H), 6.28 (dd, 1 H), 6.14-6.20 (m, 1 H), 5.60 (dddd, 1 H), 5.24 (d, 1 H), 4.38 (d, 1 H), 4.32 (d, 1 H), 4.15-4.26 (m, 1 H), 3.96 (d, 1 H), 3.85-3.92 (m, 1 H), 3.84 (d, 1 H), 3.40 (t, 1 H), 2.89 (s, 3 H), 2.53-2.71 (m, 1 H), 2.12-2.44 (m, 3 H), 1.92-2.11 (m, 1 H), 1.55-1.82 (m, 3 H), 1.52 (s, 3 H), 1.43 (dd, 1 H), 0.95 (s, 3 H) |

Example 19

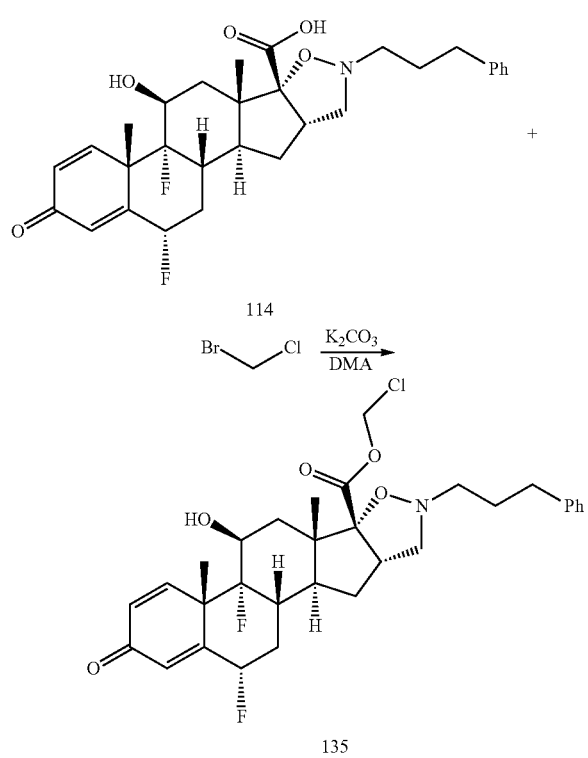

Preparation of (4aS,4bR,5S,6aS,6bR,9aS,10aS,10bS,12S)-4-b,12-Difluoro-5-hydroxy-4-a,6a-dimethyl-2-oxo-8-(3-phenyl-propyl)-2,4-a,4b,5,6,6a,8,9,9a,10,10a,10b,11,12-tetradecahydro-7-oxa-8-aza-pentaleno[2,1-a]phenanthrene-6b-carboxylic acid chloromethyl ester (Compound 135)

To a solution of compound 114 (120 mg, 0.227 mmol) in N,N-dimethylacetamide (4 ml), under nitrogen atmosphere, potassium carbonate (62.9 mg, 0.455 mmol) and bromochloromethane (0.075 ml, 1.137 mmol) were added, and the reaction mixture was stirred at RT for 25 hours. The reaction mixture was diluted with AcOEt (40 ml), and the organic layer was washed with 5% NaHCO$_3$, water and brine, dried (Na$_2$SO$_4$) and concentrated. The crude material was purified by flash chromatography on silica gel, in gradient elution from DCM to DCM/AcOEt 85:15 to afford 31.5 mg of the title compound (24% yield).

$^1$H NMR (300 MHz, DMSO-d$_6$) ppm 7.08-7.34 (m, 6H), 6.29 (dd, 1H), 6.11 (s, 1H), 5.95 (d, 1H), 5.92 (d, 1H), 5.53-5.80 (m, 1H), 5.53 (dd, 1H), 4.10-4.24 (m, 1H), 3.43-3.72 (m, 2H), 2.54-2.70 (m, 4H), 2.18-2.34 (m, 2H), 2.04-2.19 (m, 1H), 1.80-1.95 (m, 1H), 1.60-1.80 (m, 5H), 1.50-1.60 (m, 1H), 1.49 (s, 3H), 1.38-1.47 (m, 1H), 0.94 (s, 3H).

LC-MS (ESI POS): 576.07 (MH+)

The compounds listed in Table 12 were prepared as previously described for compound 135:

TABLE 12

| Compound | Structure | Yield | Analytical |
|---|---|---|---|
| 136 | 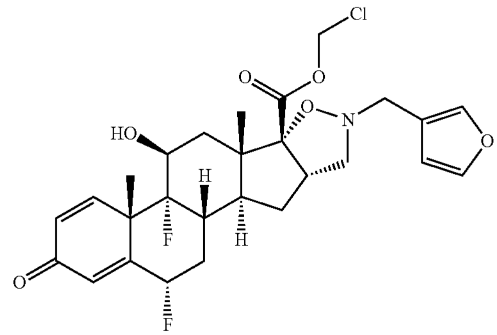 | 17% | LC-MS (ESI POS): 537.98 (MH+)<br>$[\alpha]_D^{25}$ = +52.92° (c = 0.39, CHCl$_3$)<br>$^1$H NMR (300 MHz, DMSO-d$_6$) ppm 7.54 (t, 1 H), 7.50 (s, 1 H), 7.25 (dd, 1 H), 6.38 (d, 1 H), 6.30 (dd, 1 H), 6.11 (s, 1 H), 5.97 (d, 1 H), 5.91 (d, 1 H), 5.55-5.81 (m, 1 H), 5.54 (d, 1 H), 4.10-4.31 (m, 1 H), 3.72 (br. s., 2 H), 3.37-3.63 (m, 2 H), 2.03-2.36 (m, 3 H), 1.81-1.95 (m, 1 H), 1.53-1.79 (m, 3 H), 1.49 (s, 3 H), 1.38-1.48 (m, 2 H), 0.95 (s, 3 H) |
| 137 | 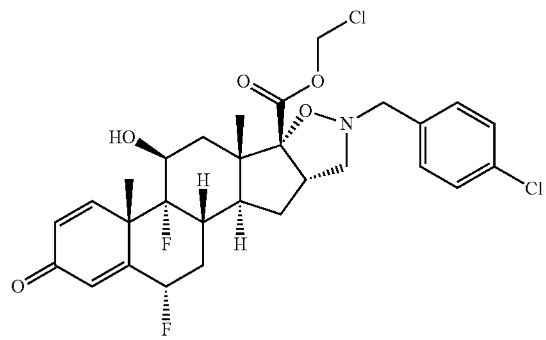 | 49%<br>white solid | LC-MS (ESI POS): 582.18 MH+<br>$[\alpha]_D^{25}$ = +86.30 (c = 0.2, CHCl$_3$)<br>$^1$H NMR (300 MHz, DMSO-d$_6$) ppm 7.21-7.41 (m, 5 H), 6.29 (dd, 1 H), 6.12 (s, 1 H), 5.96 (m, 1 H), 5.93 (d, 1 H), 5.54-5.74 (m, 1 H), 5.52 (dd, 1 H), 4.04-4.20 (m, 1 H), 3.90-4.03 (m, 1 H), 3.80 (d, 1 H), 3.49-3.68 (m, 2 H), 2.56-2.61 (m, 1 H), 2.04-2.25 (m, 2 H), 1.54-1.87 (m, 5 H), 1.49 (s, 3 H), 1.39-1.47 (m, 1 H), 0.94 (s, 3 H) |
| 138 | 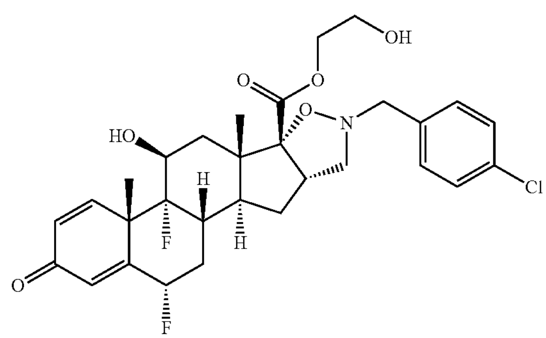 | 31% | LC-MS (ESI POS): 578.22 MH+<br>$[\alpha]_D^{25}$ = +72.73, (c = 0.52, MeOH)<br>$^1$H NMR (300 MHz, CHLOROFORM-d) ppm 7.29-7.34 (m, 2 H), 7.23-7.29 (m, 2 H), 7.15 (dd, 1 H), 6.48 (s, 1 H), 6.42 (dd, 1 H), 5.40 (dddd, 1 H), 4.19-4.47 (m, 3 H), 4.07 (s, 2 H), 3.60-3.92 (m, 4 H), 2.33-2.64 (m, 2 H), 2.09-2.33 (m, 2 H), 1.61-1.93 (m, 3 H), 1.54 (s, 3 H), 1.17-1.50 (m, 2 H), 1.05 (s, 3 H) |

Example 20

-continued

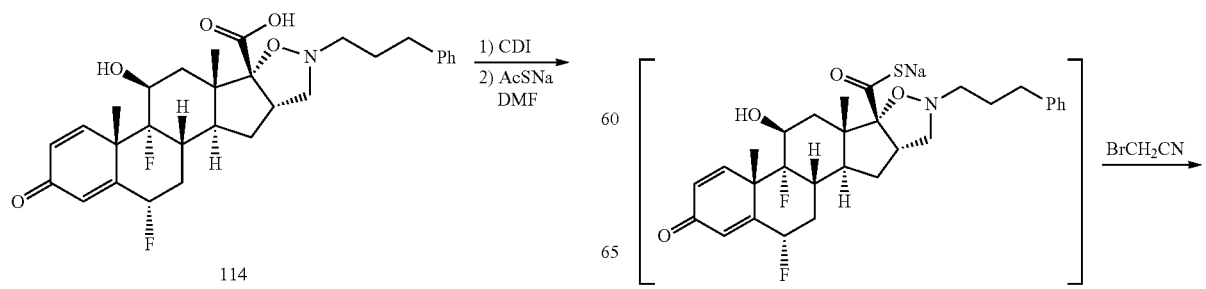

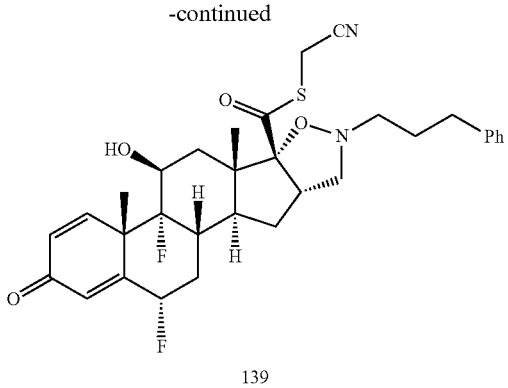

139

Preparation of (4aS,4bR,5S,6aS,6bR,9aS,10aS,10bS,
12S)-4-b,12-Difluoro-5-hydroxy-4-a,6a-dimethyl-2-
oxo-8-(3-phenyl-propyl)-2,4-a,4b,5,6,6a,8,9,9a,10,
10a,10b,11,12-tetradecahydro-7-oxa-8-aza-pentaleno
[2,1-a]phenanthrene-6b-carbothioic acid
S-cyanomethyl ester (139)

A mixture of compound 114 (220 mg, 0.417 mmol) and CDI (135 mg, 0.834 mmol) in dry DMF (4 ml) was stirred at 65° C. under nitrogen for 1 hour and 30 minutes. The mixture was cooled at RT, then at 0° C.; a freshly prepared solution of thioacetic acid (0.096 ml, 1.334 mmol) and sodium hydride (50.0 mg, 1.251 mmol) in dry DMF (2 ml) was added to the mixture, and the resulting solution was stirred at 0° C. for 10 minutes. 2-Bromoacetonitrile (0.119 ml, 1.710 mmol) was then added, and the resulting mixture was stirred at RT for 3 hours. The mixture was partitioned between AcOEt (40 ml) and water (30 ml), and the organic phase was separated; the aqueous layer was extracted with AcOEt (2×40 ml), and the combined organic layers were washed with brine, dried over $Na_2SO_4$ and concentrated. The crude material was purified by silica gel flash chromatography in gradient elution from DCM to DCM/AcOEt 90:10 to give 100 mg of the title compound (41.2% yield).

$^1$H NMR (300 MHz, DMSO-$d_6$) ppm 7.05-7.34 (m, 6H), 6.29 (dd, 1H), 6.11 (s, 1H), 5.55 (dd, 1H), 5.49-5.82 (m, 1H), 4.12-4.24 (m, 1H), 3.96 (d, 1H), 3.89 (d, 1H), 3.46-3.67 (m, 1H), 3.33-3.45 (m, 1H), 2.54-2.84 (m, 5H), 1.99-2.33 (m, 3H), 1.49 (s, 3H), 1.42-1.93 (m, 7H), 0.92 (s, 3H).

LC-MS (ESI POS): 583.98 (MH+)

$[\alpha]_D^{25}$=118.2° (c=0.49, CHCl$_3$)

The compounds listed in Table 13 were prepared as previously described for compound 139 and the suitable bromoethane derivative:

TABLE 13

| Compound | Structure | Yield | Analytical |
|---|---|---|---|
| 140 | 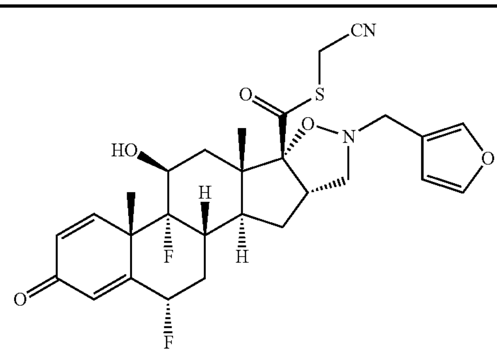 | 17% | LC-MS (ESI POS): 545.09 (MH+)<br>$^1$H NMR (300 MHz, DMSO-$d_6$) ppm 7.47-7.63 (m, 2 H), 7.25 (dd, 1 H), 6.41 (t, 1 H), 6.30 (dd, 1 H), 6.09-6.16 (m, 1 H), 5.56 (dd, 1 H), 5.49-5.78 (m, 1 H), 4.10-4.26 (m, 1 H), 3.93 (d, 1 H), 3.86 (d, 1 H), 3.83 (d, 1 H), 3.76 (d, 1 H), 3.49 (d, 1 H), 3.33-3.44 (m, 1 H), 2.55-2.70 (m, 1 H), 2.02-2.35 (m, 3 H), 1.81-1.97 (m, 1 H), 1.49 (s, 3 H), 1.41-1.79 (m, 4 H), 0.91 (s, 3 H) |
| 141 | 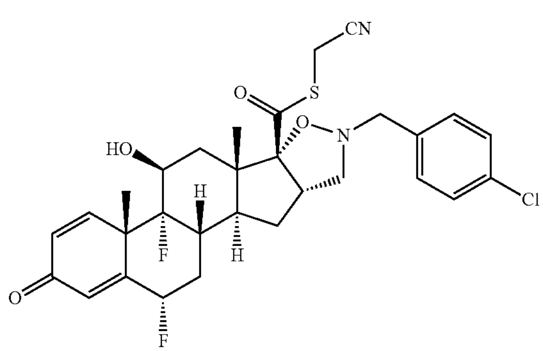 | 20% | LC-MS (ESI POS): 589.07 (MH+)<br>$^1$H NMR (300 MHz, DMSO-$d_6$) ppm 7.31-7.37 (m, 4 H) 7.19-7.27 (m, 1 H) 6.30 (dd, 1 H) 6.12 (s, 1 H) 5.47-5.79 (m, 2 H) 4.09-4.22 (m, 1 H) 3.99 (d, 1 H) 3.77-3.91 (m, 3 H) 3.45-3.61 (m, 1 H) 3.32-3.46 (m, 2 H) 2.02-2.26 (m, 2 H) 1.74-1.91 (m, 1 H) 1.57-1.74 (m, 2 H) 1.41-1.56 (m, 5 H) 0.90 (s, 3 H) |

TABLE 13-continued

| Compound | Structure | Yield | Analytical |
|---|---|---|---|
| 142 | 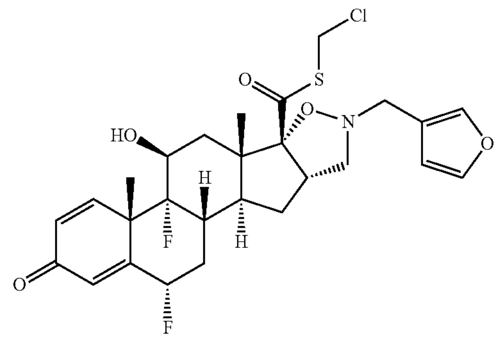 | 33% | LC-MS (ESI POS): 554.046 (MH+)<br>$[\alpha]_D^{25} = +78.43°$ (c = 0.43, CHCl$_3$)<br>$^1$H NMR (300 MHz, DMSO-d$_6$) ppm 7.56 (d, 2 H), 7.24 (dd, 1 H), 6.40 (t, 1 H), 6.30 (dd, 1 H), 6.12 (s, 1 H), 5.55-5.83 (m, 1 H), 5.48-5.54 (m, 1 H), 5.09 (d, 1 H), 5.04 (d, 1 H), 4.03-4.30 (m, 1 H), 3.81 (d, 1 H), 3.75 (d, 1 H), 3.43-3.60 (m, 1 H), 3.33-3.44 (m, 1 H), 2.57-2.66 (m, 1 H), 2.02-2.25 (m, 3 H), 1.82-1.94 (m, 1 H), 1.54-1.77 (m, 3 H), 1.49 (s, 3 H), 1.39-1.48 (m, 1 H), 0.91 (s, 3 H) |
| 143 | 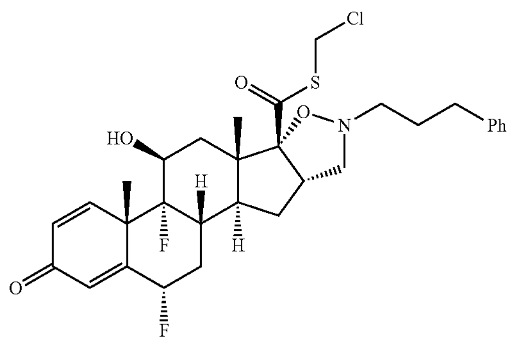 | 12%<br>White solid | LC-MS (ESI POS): 592.13 (MH+) |
| 144 | 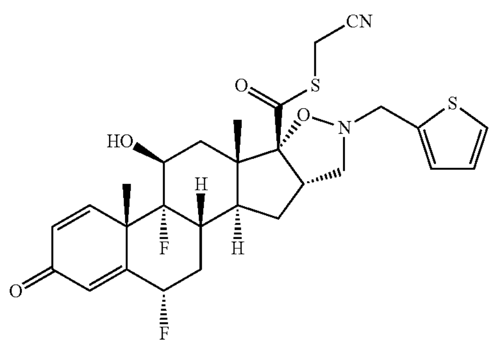 | 7% | LC-MS (ESI POS): 561.04 MH+<br>$[\alpha]_{D25} = +30.46$ (c = 0.195, CHCl$_3$)<br>$^1$H NMR (300 MHz, ACETONITRILE-d$_3$) ppm 7.32 (dd, 1 H), 7.21 (dd, 1 H), 6.99-7.02 (m, 1 H), 6.97 (dd, 1 H), 6.31 (dd, 1 H), 6.21-6.27 (m, 1 H), 5.50 (dddd, 1 H), 4.28-4.39 (m, 1 H), 4.23 (d, 1 H), 4.17 (d, 1 H), 3.69 (d, 1 H), 3.60 (d, 1 H), 3.47-3.54 (m, 1 H), 3.32-3.45 (m, 1 H), 2.48-2.83 (m, 1 H), 2.21-2.40 (m, 2 H), 2.01-2.11 (m, 1 H), 1.55-1.85 (m, 5 H), 1.53 (s, 3 H), 0.99 (s, 3 H) |
| 145 | 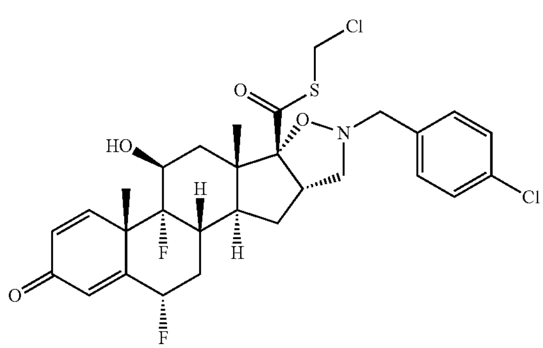 | 67% | LC-MS (ESI POS): 598.16 MH+<br>$[\alpha]_D^{25} = +137.2$ (c = 0.136, CHCl$_3$)<br>$^1$H NMR (300 MHz, CHLOROFORM-d) ppm 7.23-7.32 (m, 4 H), 7.11 (dd, 1 H), 6.47 (s, 1 H), 6.40 (dd, 1 H), 5.41 (dddd, 1 H), 5.02 (d, 1 H), 4.71 (d, 1 H), 4.32-4.48 (m, 1 H), 3.96 (d, 1 H), 3.88 (d, 1 H), 3.41-3.68 (m, 2 H), 2.12-2.70 (m, 5 H), 1.66-1.89 (m, 3 H), 1.55 (s, 3 H), 1.42-1.53 (m, 2 H), 1.02 (s, 3 H) |

TABLE 13-continued

| Compound | Structure | Yield | Analytical |
|---|---|---|---|
| 146 | 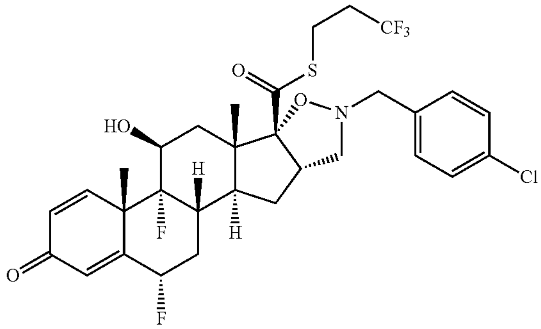 | 36% | LC-MS (ESI POS): 646.19 MH+<br>[α]$_D^{25}$ = +168.3 (c = 0.127, CHCl$_3$)<br>$^1$H NMR (300 MHz, DMSO-d6) ppm 7.33 (s, 4 H), 7.24 (dd, 1 H), 6.30 (dd, 1 H), 6.12 (s, 1 H), 5.48-5.78 (m, 1 H), 5.45 (dd, 1 H), 4.06-4.28 (m, 1 H), 3.97 (d, 1 H), 3.82 (d, 1 H), 3.45-3.63 (m, 1 H), 3.33-3.45 (m, 1 H), 2.94 (t, 2 H), 2.54-2.69 (m, 2 H), 2.35-2.47 (m, 2 H), 2.02-2.35 (m, 2 H), 1.75-1.90 (m, 1 H), 1.50-1.75 (m, 4 H), 1.49 (s, 3 H), 0.86 (s, 3 H) |
| 147 | 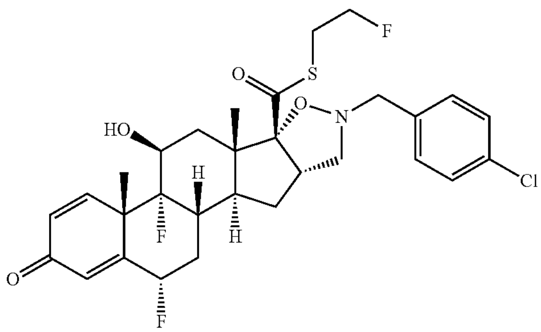 | 27% | LC-MS (ESI POS): 596.08 MH+<br>[α]$_D^{25}$ = +238.3 (c = 0.18, CHCl$_3$)<br>$^1$H NMR (300 MHz, DMSO-d6) ppm 7.33 (s, 4 H), 7.24 (d, 1 H), 6.30 (dd, 1 H), 6.12 (s, 1 H), 5.50-5.78 (m, 1 H), 5.39-5.50 (m, 1 H), 4.45 (m, 2 H), 4.09-4.22 (m, 1 H), 3.98 (d, 1 H), 3.83 (d, 1 H), 3.34-3.57 (m, 2 H), 3.12 (dt, 2 H), 2.55-2.62 (m, 1 H), 2.02-2.25 (m, 2 H), 1.52-1.89 (m, 6 H), 1.49 (s, 3 H), 0.86 (s, 3 H) |
| 148 | 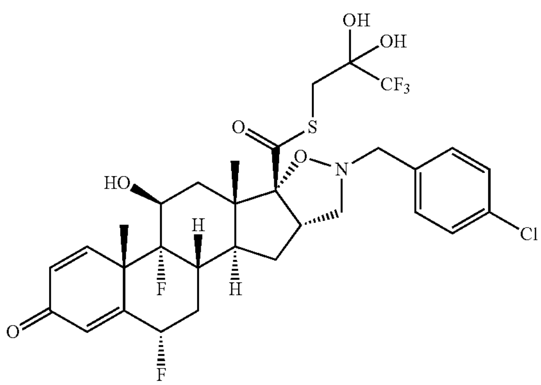 | 22% | LC-MS (ESI POS): 678.18 MH+<br>[α]$_D^{25}$ = +143.2 (c = 0.1535, MeOH)<br>$^1$H NMR (300 MHz, DMSO-d6 +TFA) ppm 7.29-7.45 (m, 4 H), 7.25 (d, 1 H), 6.29 (dd, 1 H), 6.12 (s, 1 H), 5.49-5.85 (m, 1 H), 5.44 (br. s., 1 H), 4.11-4.20 (m, 1 H), 4.00 (d, 1 H), 3.84 (d, 1 H), 3.47-3.63 (m, 1 H), 3.36-3.47 (m, 1 H), 3.20 (s, 2 H), 2.57-2.71 (m, 1 H), 2.01-2.33 (m, 3 H), 1.51-1.92 (m, 4 H), 1.48 (s, 3 H), 1.39-1.48 (m, 1 H), 0.86 (s, 3 H) |
| 149 | 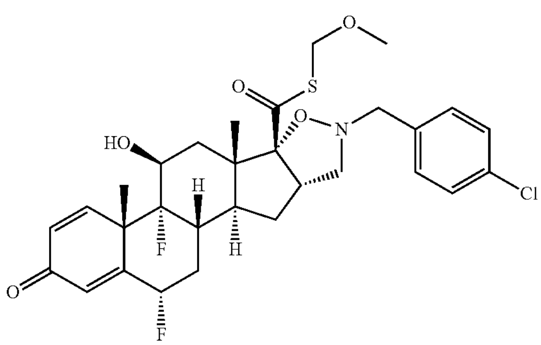 | 18% | LC-MS (ESI POS): 594.11 MH+<br>[α]$_D^{25}$ = +194.5 (c = 0.0975, CHCl$_3$)<br>$^1$H NMR (300 MHz, DMSO-d6) ppm 7.31-7.39 (m, 4 H), 7.24 (dd, 1 H), 6.30 (dd, 1 H), 5.47 (dd, 1 H), 4.95 (s, 2 H), 4.05-4.26 (m, 1 H), 3.97 (d, 1 H), 3.83 (d, 1 H), 3.45-3.61 (m, 1 H), 3.35-3.47 (m, 1 H), 3.19 (s, 3 H), 2.55-2.69 (m, 1 H), 2.03-2.29 (m, 3 H), 1.77-1.94 (m, 1 H), 1.50-1.77 (m, 4 H), 1.49 (s, 3 H), 0.87 (s, 3 H) |

TABLE 13-continued

| Compound | Structure | Yield | Analytical |
|---|---|---|---|
| 150 | 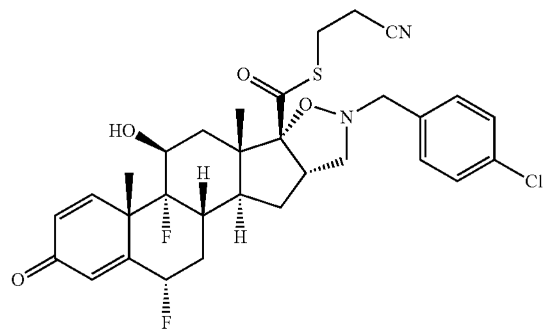 | 9% | LC-MS (ESI POS): 603.2 MH+<br>$[\alpha]_D^{25}$ = +134.9 (c = 0.29, CHCl$_3$)<br>$^1$H NMR (300 MHz, CHLOROFORM-d) ppm 7.24-7.36 (m, 4 H) 7.14 (dd, 1 H) 6.47 (s, 1 H) 6.41 (dd, 1 H) 5.25-5.54 (m, 1 H) 4.39 (dd, 1 H) 3.85-4.03 (m, 2 H) 3.46-3.65 (m, 2 H) 3.18 (dt, 1 H) 2.94 (dt, 1 H) 2.59-2.85 (m, 2 H) 2.39-2.59 (m, 1 H) 2.13-2.39 (m, 4 H) 1.63-1.88 (m, 4 H) 1.54 (s, 3 H) 1.46-1.53 (m, 1 H) 1.00 (s, 3 H) |
| 151 | 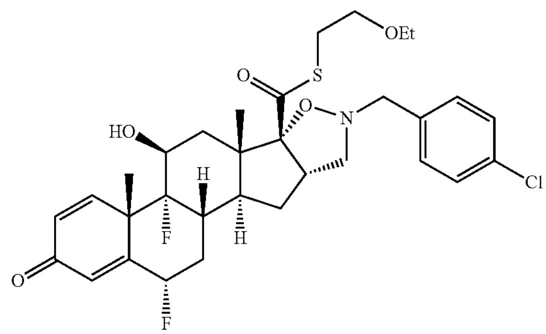 | 21% | LC-MS (ESI POS): 622.27 MH+<br>$[\alpha]_D^{25}$ = +175.2 (c = 0.1105; CHCl$_3$)<br>$^1$H NMR (300 MHz, DMSO-d6) ppm 7.28-7.41 (m, 4 H) 7.25 (dd, 1 H) 6.29 (dd, 1 H) 6.12 (s, 1 H) 5.50-5.80 (m, 1 H) 5.46 (s, 1 H) 4.15 (d, 1 H) 3.97 (d, 1 H) 3.81 (d, 1 H) 3.33-3.63 (m, 6 H) 2.94 (t, 2 H) 2.53-2.62 (m, 1 H) 2.02-2.35 (m, 3 H) 1.76-1.89 (m, 1 H) 1.51-1.76 (m, 3 H) 1.49 (s, 3 H) 1.41-1.46 (m, 1 H) 1.12 (t, 3 H) 0.86 (s, 3 H) |
| 152 | 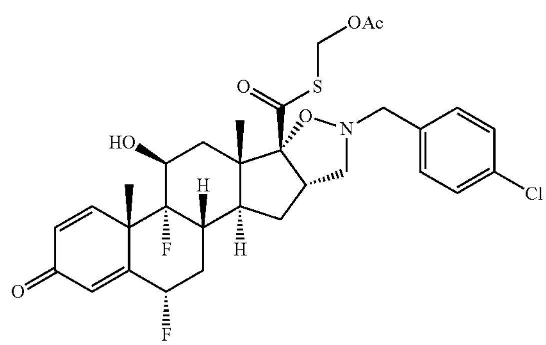 | 48% | LC-MS (ESI POS): 622.25 MH+<br>$[\alpha]_D^{25}$ = +194.7 (c = 0.2465; CHCl$_3$)<br>$^1$H NMR (300 MHz, DMSO-d$_6$) ppm 7.27-7.36 (m, 4 H), 7.24 (dd, 1 H), 6.30 (dd, 1 H), 6.12 (s, 1 H), 5.51-5.78 (m, 1 H), 5.49 (dd, 1 H), 5.37 (d, 1 H), 5.30 (d, 1 H), 4.07-4.25 (m, 1 H), 3.98 (d, 1 H), 3.81 (d, 1 H), 3.47-3.62 (m, 1 H), 3.35-3.47 (m, 1 H), 2.55-2.71 (m, 1 H), 2.07-2.31 (m, 2 H), 2.04 (s, 3 H), 1.81 (dt, 1 H), 1.51-1.72 (m, 5 H), 1.49 (s, 3 H), 0.86 (s, 3 H) |
| 153 | 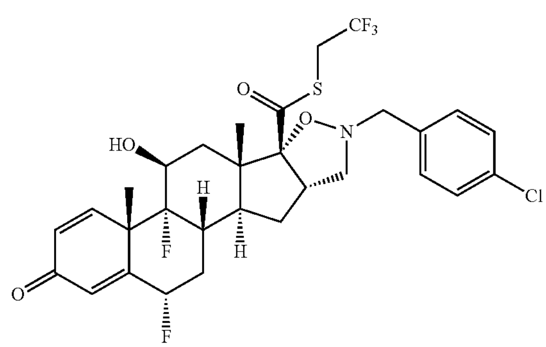 | 66% | LC-MS (ESI POS): 632.32 MH+<br>$[\alpha]_D^{25}$ = +186.4 (c = 0.0985, CHCl$_3$)<br>$^1$H NMR (300 MHz, DMSO-d$_6$) ppm 7.32 (s, 4 H), 7.23 (dd, 1 H), 6.30 (dd, 1 H), 6.13 (s, 1 H), 5.56-5.79 (m, 1 H), 5.54 (dd, 1 H), 4.08-4.24 (m, 1 H), 4.00 (d, 1 H), 3.83 (d, 1 H), 3.76 (q, 2 H), 3.46-3.62 (m, 1 H), 3.34-3.46 (m, 1 H), 2.57-2.72 (m, 1 H), 2.02-2.38 (m, 3 H), 1.84 (ddd, 1 H), 1.51-1.74 (m, 4 H), 1.49 (s, 3 H), 0.86 (s, 3 H) |

TABLE 13-continued

| Compound | Structure | Yield | Analytical |
|---|---|---|---|
| 154 | 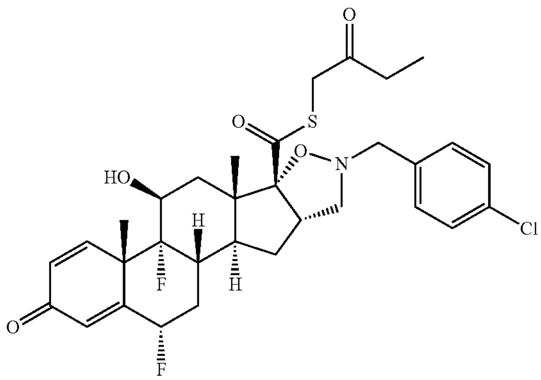 | 36% | LC-MS (ESI POS): 620.29 MH+<br>$[\alpha]_D^{25}$ = +155.2 (c = 0.1575, CHCl$_3$)<br>$^1$H NMR (300 MHz, DMSO-d$_6$) ppm 7.28-7.42 (m, 4 H), 7.25 (dd, 1 H), 6.30 (dd, 1 H), 6.12 (s, 1 H), 5.54-5.82 (m, 1 H), 5.52 (dd, 1 H), 4.08-4.22 (m, 1 H), 3.98 (d, 1 H), 3.83 (d, 1 H), 3.74 (s, 2 H), 3.42-3.59 (m, 1 H), 3.32-3.42 (m, 1 H), 2.56-2.70 (m, 1 H), 2.53 (q, 2 H), 2.03-2.31 (m, 3 H), 1.52-1.90 (m, 4 H), 1.49 (s, 3 H), 1.41-1.48 (m, 1 H), 0.96 (t, 3 H), 0.86 (s, 3 H) |
| 155 | 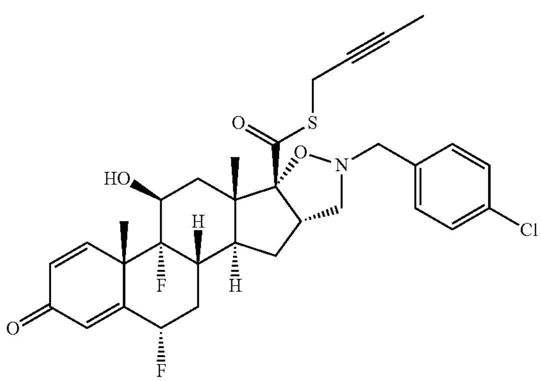 | 51% | LC-MS (ESI POS): 602.3 MH+<br>$[\alpha]_D^{25}$ = +185.2 (c = 0.1805, CHCl$_3$)<br>$^1$H NMR (300 MHz, DMSO-d$_6$) ppm 7.28-7.42 (m, 4 H), 7.24 (d, 1 H), 6.30 (dd, 1 H), 6.12 (s, 1 H), 5.50-5.78 (m, 1 H), 5.48 (dd, 1 H), 4.09-4.22 (m, 1 H), 3.96 (d, 1 H), 3.83 (d, 1 H), 3.53 (q, 2 H), 3.45-3.50 (m, 1 H), 3.34-3.45 (m, 1 H), 2.58-2.71 (m, 1 H), 2.18-2.36 (m, 2 H), 2.03-2.16 (m, 1 H), 1.80-1.88 (m, 1 H), 1.78 (t, 3 H), 1.52-1.73 (m, 3 H), 1.49 (s, 3 H), 1.41-1.47 (m, 1 H), 0.87 (s, 3 H) |
| 156 | 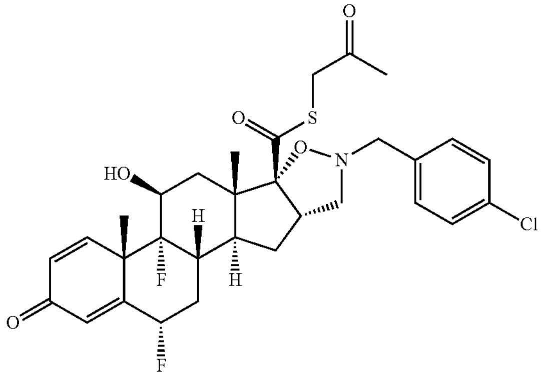 | 77% | LC-MS (ESI POS): 606.26 MH+<br>$[\alpha]_D^{25}$ = +183.5 (c = 0.5, MeOH)<br>$^1$H NMR (300 MHz, DMSO-d$_6$) ppm 7.35 (m, 4 H), 7.25 (d, 1 H), 6.30 (dd, 1 H), 6.12 (s, 1 H), 5.55-5.74 (m, 1 H), 5.51 (d, 1 H), 4.07-4.25 (m, 1 H), 3.98 (d, 1 H), 3.84 (d, 1 H), 3.75 (s, 2 H), 3.44-3.58 (m, 1 H), 3.31-3.44 (m, 1 H), 2.55-2.62 (m, 1 H), 2.04-2.30 (m, 3 H), 2.18 (s, 3 H), 1.68-1.94 (m, 2 H), 1.49 (s, 3 H), 1.39-1.68 (m, 3 H), 0.86 (s, 3 H) |

Example 21

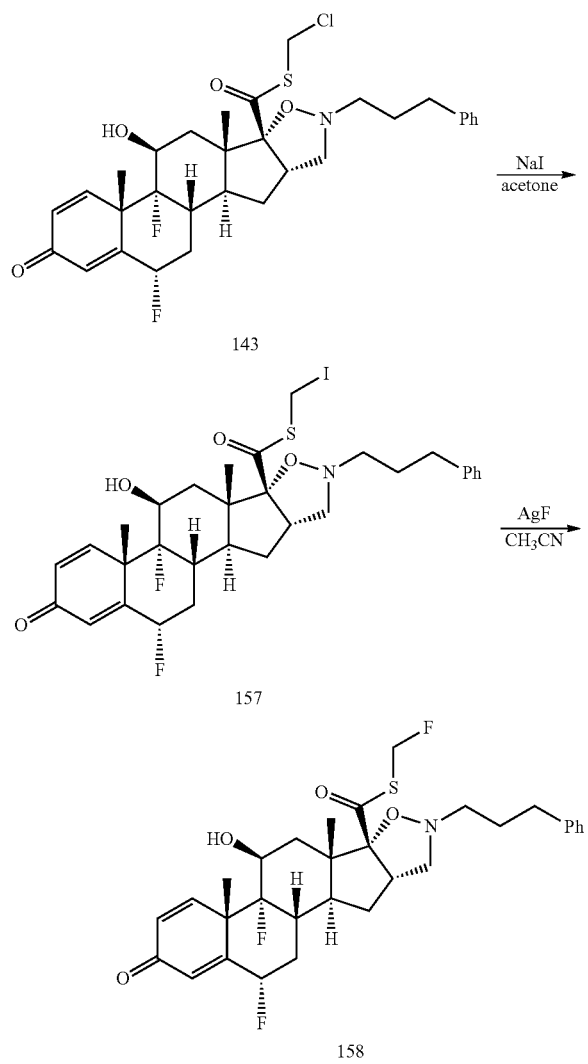

Preparation of (4aS,4bR,5S,6aS,6bR,9aS,12S)-4-b, 12-Difluoro-5-hydroxy-4-a,6a-dimethyl-2-oxo-8-(3-phenyl-propyl)-2,4-a,4b,5,6,6a,8,9,9a,10,10a,10b,11, 12-tetradecahydro-7-oxa-8-aza-pentaleno[2,1-a] phenanthrene-6b-carbothioic acid S-iodomethyl ester (Compound 157)

To a solution of compound 143 in acetone (4 ml), sodium iodide (122 mg, 0.811 mmol) was added, and the reaction mixture was stirred at 65° C. for 9 hours. The reaction mixture was diluted with AcOEt (50 ml), and the aqueous layer was washed with water, 10% sodium thiosulfate, 5% sodium bicarbonate and brine, dried over sodium sulfate anhydrous and concentrated. The crude material was purified by flash chromatography of silica gel, in gradient elution from AcOEt/Petroleum Ether 5:95 to AcOEt/Petroleum Ether 30:70, to afford 16 mg of the title compound (34.6% yield).

LC-MS (ESI POS): 684.2 (MH+)

Preparation of (4aS,4bR,5S,6aS,6bR,9aS,10aS,10bS, 12S)-4-b,12-Difluoro-5-hydroxy-4-a,6a-dimethyl-2-oxo-8-(3-phenyl-propyl)-2,4-a,4b,5,6,6a,8,9,9a,10, 10a,10b,11,12-tetradecahydro-7-oxa-8-aza-pentaleno [2,1-a]phenanthrene-6b-carbothioic acid S-fluoromethyl ester (Compound 158)

To a solution of compound 157 (16 mg, 0.023 mmol) in acetonitrile (7 ml), silver fluoride (41.6 mg, 0.328 mmol) was added, and the reaction mixture was stirred at RT in the dark overnight. The reaction mixture was filtered through a cotton pad and concentrated to give 28 mg of crude material, which was purified by RP18 cartridge in acetonitrile, to afford 13 mg of a mixture containing the desired product. The mixture was further purified by $SiO_2$ cartridge in gradient elution from AcOEt/DCM 15:85 to AcOEt/DCM 30:70 to afford 2.1 mg of the title compound (16% yield).

$^1$H NMR (300 MHz, CHLOROFORM-d) ppm 7.16-7.33 (m, 5H), 7.12 (dd, 1H), 6.46 (s, 1H), 6.40 (dd, 1H), 6.01 (dd, 1H), 5.64 (dd, 1H), 5.41 (dddd, 1H), 4.25-4.50 (m, 1H), 3.52-3.74 (m, 2H), 2.76-2.94 (m, 2H), 2.64-2.76 (m, 2H), 2.41-2.64 (m, 1H), 2.23-2.40 (m, 2H), 1.65-2.19 (m, 6H), 1.48 (br. s., 1H), 1.28 (s, 3H), 1.22-1.36 (m, 2H), 1.03 (s, 3H).

LC-MS (ESI POS): 575.90 (MH+)

The compound listed in Table 14 was prepared as previously described for compound 158, starting from the suitable acid derivative:

TABLE 14

| Compound | Structure | Yield | Analytical |
|---|---|---|---|
| 159 | 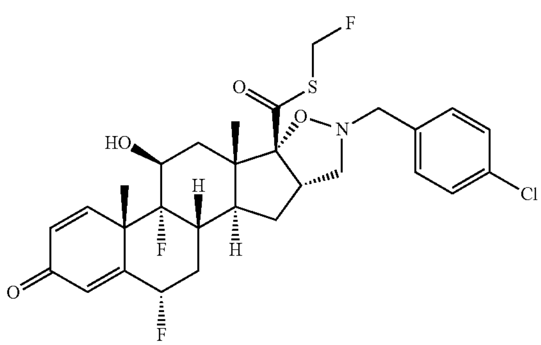 | 46% | LC-MS (ESI POS): 582.16 MH+<br>$[\alpha]_D^{25}$ = +181.2 (c = 0.13, $CHCl_3$)<br>$^1$H NMR (300 MHz, DMSO-$d_6$) ppm 7.28-7.43 (m, 4 H), 7.24 (dd, 1 H), 6.30 (dd, 1 H), 6.12 (s, 1 H), 5.87 (dd, 1 H), 5.77 (dd, 1 H), 5.52-5.74 (m, 1 H), 5.49 (dd, 1 H), 4.08-4.23 (m, 1 H), 3.97 (d, 1 H), 3.85 (d, 1 H), 3.45-3.60 (m, 1 H), 3.34-3.46 (m, 1 H), 2.56-2.69 (m, 1 H), 2.02-2.37 (m, 3 H), 1.85 (dt, 1 H), 1.50-1.78 (m, 4 H), 1.49 (s, 3 H), 0.88 (s, 3 H) |

Example 22

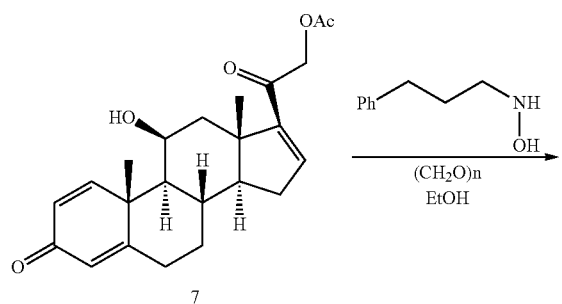

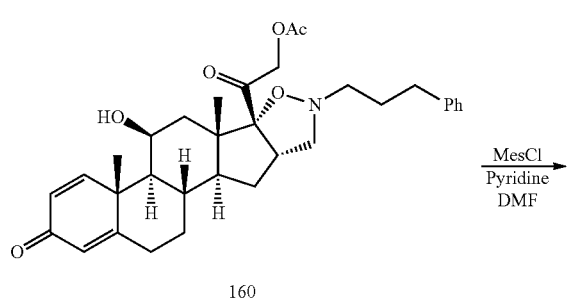

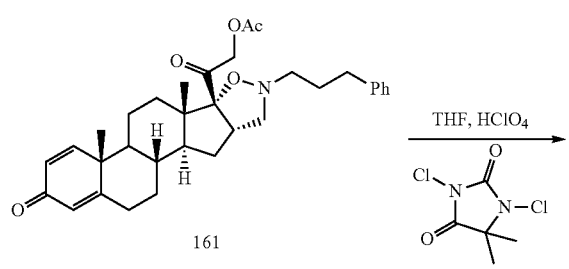

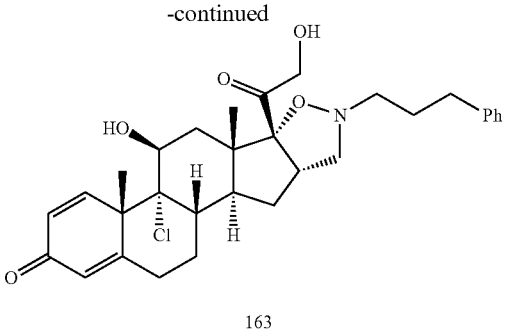

Acetic acid 2-[(4aR,5S,6aS,6bR,9aS)-5-hydroxy-4-a,6a-dimethyl-2-oxo-8-(3-phenyl-propyl)-2,4-a,4b,5,6,6a,8,9,9a,10,10a,10b,11,12-tetradecahydro-7-oxa-8-aza-pentaleno[2,1-a]phenanthren-6b-yl]-2-oxo-ethyl ester (compound 160) was obtained in 79% yield by reacting the intermediate 7 with 3-phenyl-propyl-hydroxylamine, as previously described for compound 9 (Example 3).

Preparation of acetic acid 2-[(4aS,6aS,6bR,9aS)-4-a,6a-dimethyl-2-oxo-8-(3-phenyl-propyl)-2,4-a,6,6a,8,9,9a,10,10a,10b,11,12-dodecahydro-7-oxa-8-aza-pentaleno[2,1-a]phenanthren-6b-yl]-2-oxo-ethyl ester (Compound 161)

To a solution of compound 160 (403 mg, 0.736 mmol) in DMF (8 ml), under nitrogen atmosphere, pyridine (0.268 ml, 3.31 mmol) and methanesulfonyl chloride (0.172 ml, 2.207 mmol) were added. The reaction mixture was stirred at 90° C. for 3.5 hours and at RT overnight.

The reaction mixture was poured into ice and brine (40 ml), and the aqueous layer was extracted with AcOEt (3×40 ml). The combined organic extracts were washed with water and brine, dried (Na₂SO₄), and concentrated. The crude material was purified by flash chromatography on silica gel, in gradient elution from DCM to DCM/AcOEt 85:15 to afford 211 mg of pure compound (54.1% yield).

LC-MS (ESI POS): 530.4 (MH+)

Preparation of acetic acid 2-[(4aS,4bR,5S,6aS,6bR,9aS)-4-b-chloro-5-hydroxy-4-a,6a-dimethyl-2-oxo-8-(3-phenyl-propyl)-2,4-a,4b,5,6,6a,8,9,9a,10,10a,10b,11,12-tetradecahydro-7-oxa-8-aza-pentaleno[2,1-a]phenanthren-6b-yl]-2-oxo-ethyl ester (Compound 162)

To a solution of compound 161 (211 mg, 0.398 mmol) in THF (12 ml), at 0° C. under nitrogen atmosphere, a solution of perchloric acid (0.073 ml, 1.214 mmol) in water (164 µl) was added, followed by 1,3-dichloro-5,5-dimethylhydantoin (57 mg, 0.289 mmol). After 5 minutes, the cooling bath was removed, and the mixture was stirred at RT for 3 hours. Further addition of 1,3-dichloro-5,5-dimethylhydantoin (57.0 mg, 0.289 mmol) and perchloric acid (0.073 ml, 1.215 mmol) was made, and the reaction mixture was stirred at RT for further 1 hour. The reaction mixture was poured into a 0.64% solution of NaHSO₃ (100 ml), followed by addition of solid NaCl. The aqueous layer was extracted with AcOEt (3×75 ml), and the combined organic extracts were washed with brine, dried (anhydrous Na₂SO₄), and concentrated. The crude material was purified by flash chromatography on silica gel, in gradient elution from DCM to DCM/AcOEt 70:30, to afford 112 mg of the title compound (48.3% yield).

LC-MS (ESI POS): 582.3 (MH+)

Preparation of (4aS,4bR,5S,6aS,6bR,9aS)-4-b-Chloro-5-hydroxy-6b-(2-hydroxy-acetyl)-4-a,6a-dimethyl-8-(3-phenyl-propyl)-4-a,4b,5,6,6a,6b,8,9,9a,10,10a,10b,11,12-tetradecahydro-7-oxa-8-aza-pentaleno[2,1-a]phenanthren-2-one (Compound 163)

To a solution of compound 162 (112 mg, 0.192 mmol) in MeOH (8 ml) and THF (5.00 ml) (degassed solvents), under nitrogen atmosphere, at 0° C., K$_2$CO$_3$ (39.9 mg, 0.289 mmol) was added, and the reaction mixture was stirred at 0° C. for 1.5 hours. The reaction mixture was poured into 2 N HCl and ice (50 ml), and the aqueous layer was extracted with AcOEt (3×60 ml). The combined organic extracts were washed with water and brine, dried over anhydrous sodium sulphate, and concentrated. The crude material was then purified by flash chromatography on silica gel, in gradient elution from AcOEt/DCM 5:95 to AcOEt/DCM 40:60 to afford 73 mg of the title compound (70.3% yield).

$^1$H NMR (300 MHz, CHLOROFORM-d) ppm 7.29-7.34 (m, 1H), 7.11-7.25 (m, 5H), 6.37 (dd, 1H), 6.11 (t, 1H), 4.87 (d, 1H), 4.60 (br. s., 1H), 4.22 (d, 1H), 3.75-3.88 (m, 1H), 3.59-3.75 (m, 1H), 2.88-3.16 (m, 2H), 2.68-2.79 (m, 2H), 2.54-2.70 (m, 3H), 2.36-2.53 (m, 2H), 2.19-2.33 (m, 1H), 1.99-2.17 (m, 2H), 1.71-1.93 (m, 3H), 1.67 (s, 3H), 1.60 (dd, 1H), 1.40-1.54 (m, 1H), 1.00 (s, 3H)

LC-MS (ESIPOS): 540.01 (MH+)

The compound 164 was prepared as previously described for compound 163 reacting intermediate 7 with N-p-chlorobenzyl hydroxylamine.

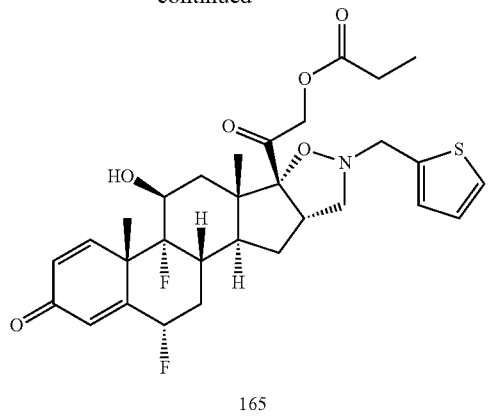

165

Preparation of propionic acid 2-((4aS,4bR,5S,6aS,6bR,9aS,10aS,10bS,12S)-4-b,12-difluoro-5-hydroxy-4-a,6a-dimethyl-2-oxo-8-thiophen-2-ylmethyl-2,4-a,4b,5,6,6a,8,9,9a,10,10a,10b,11,12-tetradecahydro-7-oxa-8-aza-pentaleno[2,1-a]phenanthren-6b-yl)-2-oxo-ethyl ester (Compound 165)

To a solution of 37 in anhydrous dichloromethane (15 ml), under nitrogen atmosphere at 0° C., triethylamine (0.161 ml, 1.155 mmol) and propionyl chloride (0.100 ml, 1.155 mmol) were added. The reaction mixture was stirred at 0° C. for 15

TABLE 15

| Compound | Structure | Yield | Analytical |
|---|---|---|---|
| 164 | (structure shown) | 21% | LC-MS (ESI POS): 546.48 (MH+)<br>$^1$H NMR (300 MHz, DMSO-d$_6$) ppm 7.08-7.45 (m, 5 H), 6.23 (dd, 1 H), 5.99 (t, 1 H), 5.51 (d, 1 H), 4.70 (br. s., 1 H), 4.27-4.45 H), 3.85-3.93 (m, 1 H), 3.68-3.84 (m, 1 H), 3.44-3.58 (m, 1 H), 3.34-3.45 (m, 1 H), 2.56-2.72 (m, 2 H), 2.21-2.43 (m, 3 H), 2.00-2.17 (m, 1 H), 1.72-1.88 (m, 1 H), 1.60 (s, 3 H), 1.46-1.59 (m, 3 H), 1.34-1.44 (m, 1 H), 0.83 (s, 3 H) |

Example 23

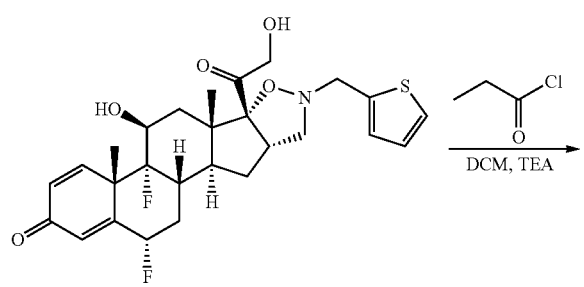

minutes and at room temperature for 24 hours, then further triethylamine (0.080 ml, 0.577 mmol) and propionyl chloride (0.050 ml, 0.577 mmol) were added. The mixture was stirred at room temperature for further 2 hours. The mixture was diluted with DCM (60 ml), and the organic phase was washed with 1 N HCl, water and brine, dried (Na$_2$SO$_4$), and concentrated. The residue was purified by silica gel flash cartridge in gradient elution from DCM to DCM/AcOEt 85:15 to afford 248 mg of 104 (75% yield).

$^1$H NMR (300 MHz, DMSO-d$_6$) ppm 7.44 (dd, 1H), 7.27 (dd, 1H), 7.00 (dd, 1H), 6.96 (dd, 1H), 6.31 (dd, 1H), 6.12 (s, 1H), 5.58 (d, 1H), 5.37-5.81 (m, 1H), 4.76 (d, 1H), 4.64 (d, 1H), 4.20-4.26 (m, 1H), 4.21 (d, 1H), 4.01 (d, 1H), 3.45-3.63 (m, 1H), 3.32-3.38 (m, 1H), 2.59-2.71 (m, 1H), 2.38 (q, 2H), 2.08-2.31 (m, 3H), 1.94-2.05 (m, 1H), 1.73 (d, 1H), 1.52-1.68 (m, 2H), 1.49 (s, 3H), 1.43 (dd, 1H), 1.05 (t, 3H), 0.85 (s, 3H)

LC-MS (ESI POS): 576.21 MH+

[α]$_D^{25}$=+162.0 (c=0.151, MeOH)

The compounds listed in Table 16 were prepared as previously described for compound 165 starting from the suitable isoxazolidine derivative:

TABLE 16

| Compound | Structure | Yield | Analytical |
|---|---|---|---|
| 166 | 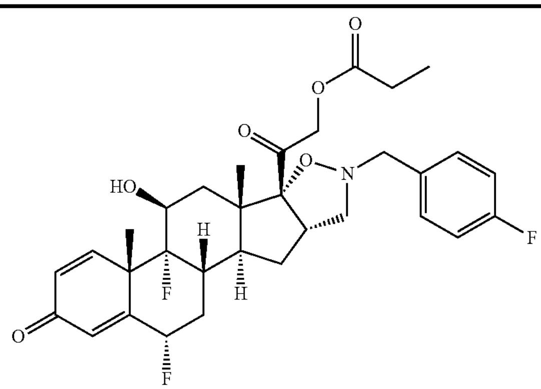 | 52% | LC-MS (ESI POS): 588.5 MH+<br>$[\alpha]_D^{25}$ = +193.4 (c = 0.2, CHCl$_3$)<br>$^1$H NMR (300 MHz, DMSO-d$_6$) ppm 7.30-7.43 (m, 2 H), 7.26 (dd, 1 H), 7.02-7.19 (m, 2 H), 6.31 (dd, 1 H), 6.13 (s, 1 H), 5.58-5.74 (m, 1 H), 5.56 (d, 1 H), 4.62 (d, 1 H), 4.44 (d, 1 H), 4.09-4.25 (m, 1 H), 3.93 (d, 1 H), 3.79 (d, 1 H), 3.40-3.59 (m, 1 H), 3.31-3.38 (m, 1 H), 2.56-2.67 (m, 1 H), 2.37 (q, 2 H), 2.09-2.26 (m, 3 H), 1.84-2.04 (m, 1 H), 1.53-1.76 (m, 3 H), 1.49 (s, 3 H), 1.34-1.47 (m, 1 H), 1.04 (t, 3 H), 0.84 (s, 3 H) |
| 167 | 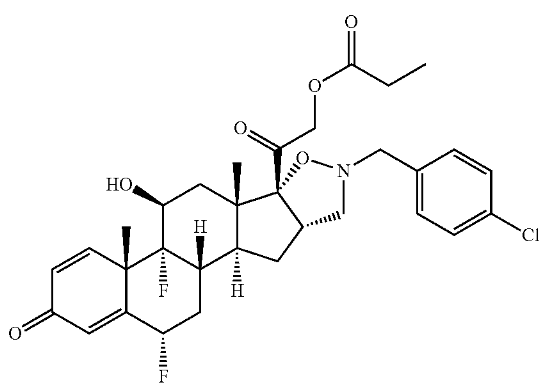 | 75% | LC-MS (ESI POS): 604.07 MH+<br>$[\alpha]_D^{25}$ = +188.5 (c = 0.2, CHCl$_3$)<br>$^1$H NMR (300 MHz, DMSO-d$_6$) ppm 7.31-7.42 (m, 4 H), 7.26 (d, 1 H), 6.31 (dd, 1 H), 6.13 (s, 1 H), 5.56 (dd, 1 H), 5.50-5.74 (m, 1 H), 4.63 (d, 1 H), 4.47 (d, 1 H), 3.95 (d, 1 H), 3.79 (d, 1 H), 3.43-3.60 (m, 1 H), 3.31-3.38 (m, 1 H), 2.54-2.61 (m, 1 H), 2.37-2.45 (m, 1 H), 2.38 (q, 2 H), 2.10-2.25 (m, 3 H), 1.88-2.02 (m, 1 H), 1.52-1.76 (m, 3 H), 1.49 (s, 3 H), 1.39-1.48 (m, 1 H), 1.05 (t, 3 H), 0.84 (s, 3 H) |

Example 24

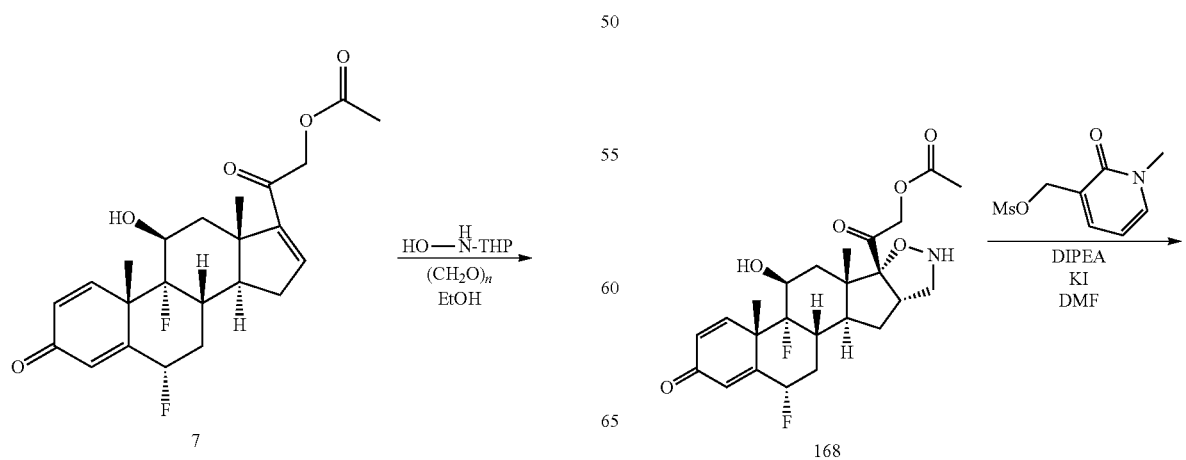

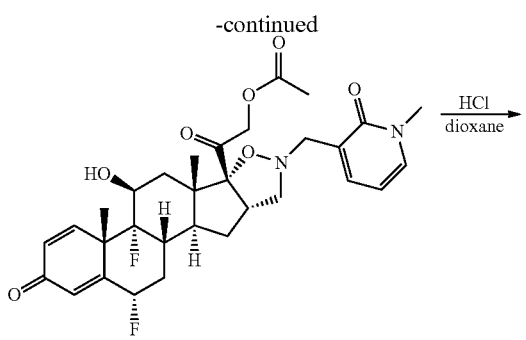

169

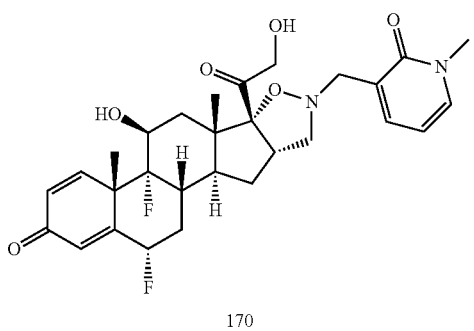

170

Preparation of Acetic acid 2-((4aS,4bR,5S,6aS,6bR, 9aS,10aS,10bS,12S)-4-b,12-difluoro-5-hydroxy-4-a, 6a-dimethyl-2-oxo-2,4-a,4b,5,6,6a,8,9,9a,10,10a, 10b,11,12-tetradecahydro-7-oxa-8-aza-pentaleno[2, 1-a]phenanthren-6b-yl)-2-oxo-ethyl ester (Compound 168)

The title compound was obtained in 33% yield, starting from intermediate 7, as previously described for compound 9 (Example 3).

LC-MS (ESI POS): 466.0 (MH+)

Preparation of Acetic acid 2-((4aS,4bR,5S,6aS,6bR, 9aS,10aS,10bS,12S)-4-b,12-difluoro-5-hydroxy-4-a, 6a-dimethyl-2-oxo-2,4-a,4b,5,6,6a,8,9,9a,10,10a, 10b,11,12-tetradecahydro-7-oxa-8-N-(1-methyl-2-oxo-1,2-dihydro-pyridin-3-ylmethyl)-aza-pentaleno [2,1-a]phenanthren-6b-yl)-2-oxo-ethyl ester (Compound 169)

To a solution of compound 168 (200 mg, 0.430 mmol), potassium iodide (164 mg, 0.988 mmol) and ethyldiisopropylamine (0.169 ml, 0.988 mmol) in anhydrous DMF (3 ml), (1-methyl-2-oxo-1,2-dihydropyridin-3-yl)methyl methanesulfonate (215 mg, 0.988 mmol) dissolved in anhydrous DMF (5 ml) was added. The reaction mixture was stirred under microwave heating at 100° C. for 3 hours. The reaction mixture was diluted with AcOEt (50 ml), and the organic phase was washed with water and brine, dried (Na$_2$SO$_4$), and concentrated. The residue was purified by flash chromatography on silica gel, in gradient elution from DCM/MeOH/AcOEt 49:1:50 to DCM/MeOH/AcOEt 47:3:50, to afford 115 mg of the title compound (46% yield).

LC-MS (ESI POS): 587.1 (MH+)

Preparation of (4aS,4bR,5S,6aS,6bR,9aS,10aS,10bS, 12S)-4-b,12-Difluoro-5-hydroxy-6b-(2-hydroxy-acetyl)-4-a,6a-dimethyl-4-a,4b,5,6,6a,6b,8,9,9a,10, 10a,10b,11,12-tetradecahydro-7-oxa-8-N-(1-methyl-2-oxo-1,2-dihydro-pyridin-3-ylmethyl)-aza-pentaleno[2,1-a]phenanthren-2-one (Compound 170)

To a solution of compound 169 (115 mg, 0.196 mmol) in dioxane (12 ml) and water (6.00 ml), 12 N HCl (1.5 ml) was added, and the reaction mixture was stirred at 60° C. for 3 hours. The reaction mixture was cooled to 0° C., and the pH was adjusted to 9. Brine was added, and the aqueous phase was extracted with AcOEt (2×50 ml). The combined organic extracts were dried (Na$_2$SO$_4$) and concentrated. The crude material was purified by silica gel flash cartridge in gradient elution from AcOEt to AcOEt/MeOH 97:3, to afford 73 mg of the title compound (68% yield).

$^1$H NMR (300 MHz, DMSO-d$_6$) ppm 7.62 (dd, 1H), 7.37 (dd, 1H), 7.26 (d, 1H), 6.30 (dd, 1H), 6.17 (t, 1H), 6.12 (s, 1H), 5.49-5.83 (m, 1H), 5.43 (dd, 1H), 4.77 (t, 1H), 4.32 (dd, 1H), 4.10-4.22 (m, 1H), 4.01 (dd, 1H), 3.71 (br. s., 2H), 3.44-3.56 (m, 2H), 3.42 (s, 3H), 2.58-2.71 (m, 1H), 2.07-2.35 (m, 3H), 1.83-1.99 (m, 1H), 1.52-1.68 (m, 3H), 1.49 (s, 3H), 1.38-1.47 (m, 1H), 0.81 (s, 3H)

LC-MS (ESI POS): 545.25 MH+

$[\alpha]_D^{25}$=+190.6 (c=0.136, MeOH)

The compounds listed in Table 16 were prepared as previously described for compound 170, with the suitable alkylating agent

TABLE 17

| Compound | Structure | Yield | Analytical |
|---|---|---|---|
| 171 | 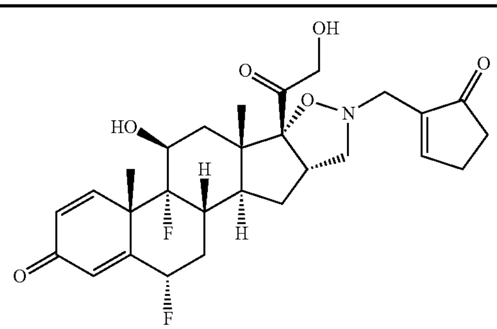 | 11% | LC-MS (ESI POS): 518.19 MH+<br>$^1$H NMR (300 MHz, CHLOROFORM-d) ppm 7.61-7.79 (m, 1 H), 7.11 (dd, 1 H), 6.48 (s, 1 H), 6.41 (dd, 1 H), 5.24-5.53 (m, 1 H), 4.63 (d, 1 H), 4.36-4.49 (m, 1 H), 4.18 (d, 1 H), 3.55-3.74 (m, 4 H), 2.59-2.76 (m, 2 H), 2.38-2.50 (m, 3 H), 2.21-2.38 (m, 4 H), 1.65-1.89 (m, 4 H), 1.54 (s, 3 H), 0.96 (s, 3 H) |

TABLE 17-continued

| Compound | Structure | Yield | Analytical |
|---|---|---|---|
| 172 | 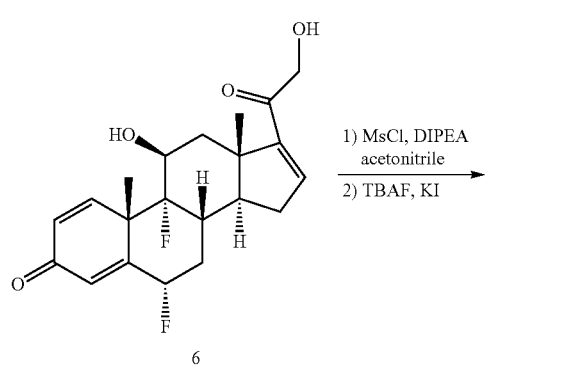 | 57% | LC-MS (ESI POS): 535.1 MH+<br>$[\alpha]_D^{25}$ = +171.1 (c = 0.121, MeOH)<br>$^1$H NMR (300 MHz, DMSO-$d_6$) ppm 7.25 (s, 1 H), 7.26 (dd, 1 H), 6.30 (dd, 1 H), 6.12 (s, 1 H), 5.63 (dddd, 1 H), 5.43 (dd, 1 H), 4.73 (t, 1 H), 4.35 (dd, 1 H), 4.12-4.21 (m, 1 H), 3.99 (dd, 1 H), 3.92 (s, 2 H), 3.33-3.58 (m, 2 H), 2.60 (s, 3 H), 2.54-2.59 (m, 1 H), 2.03-2.33 (m, 3 H), 1.85-2.03 (m, 1 H), 1.52-1.65 (m, 3 H), 1.48-1.51 (m, 3 H), 1.39-1.47 (m, 1 H), 0.81 (s, 3 H) |

Example 25

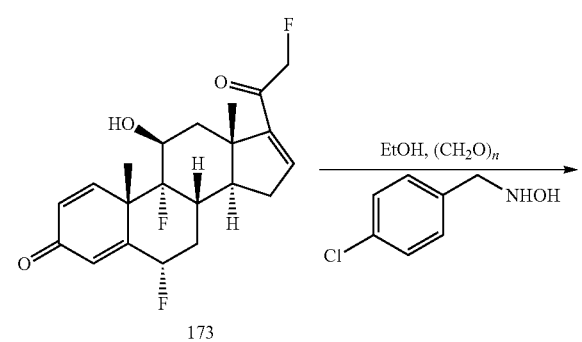

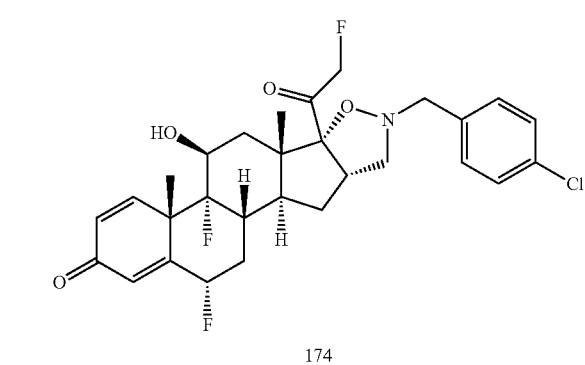

Preparation of (6S,8S,9R,10S,11S,13S,14S)-6,9-Difluoro-17-(2-fluoro-acetyl)-11-hydroxy-10,13-dimethyl-6,7,8,9,10,11,12,13,14,15-decahydro-cyclopenta[a]phenanthren-3-one (Compound 173)

To a solution of compound 6 (0.5 g, 1.321 mmol) in dry acetonitrile (20 ml), under nitrogen atmosphere, DIPEA (0.396 ml, 2.246 mmol) and Ms-Cl (0.155 ml, 1.982 mmol) were added, and the reaction mixture was stirred at room temperature for 1 hour. Then, TBAF (2.64 ml, 2.64 mmol) 1 M in THF and potassium fluoride (0.077 g, 1.321 mmol) were added, and the mixture was heated at reflux overnight. The mixture was diluted with AcOEt and the organic phase was washed with water, brine, dried (Na$_2$SO$_4$), and concentrated. Crude was purified by flash chromatography on silica gel, in gradient elution from petroleum ether/AcOEt 8:2 to AcOEt, to afford the title compound (98% yield).
LC-MS (ESI POS): 381.3 MH+

Preparation of (4aS,4bR,5S,6aS,6bR,9aS,10aS,10bS,12S)-8-(4-Chloro-benzyl)-4-b,12-difluoro-6b-(2-fluoro-acetyl)-5-hydroxy-4-a,6a-dimethyl-4-a,4b,5,6,6a,6b,8,9,9a,10,10a,10b,11,12-tetradecahydro-7-oxa-8-aza-pentaleno[2,1-a]phenanthren-2-one (Compound 174)

Compound 173 was obtained in 21% yield reacting the intermediate 111 with N-(4-Chloro-benzyl)-hydroxylamine, as previously described for compound 9 (Example 3).
$^1$H NMR (300 MHz, DMSO-d6) ppm 7.36-7.44 (m, 2H), 7.29-7.36 (m, 2H), 7.27 (dd, 1H), 6.30 (dd, 1H), 6.13 (s, 1H), 5.49-5.79 (m, 1H), 5.46 (dd, 1H), 4.92 (dd, 1H), 4.67-4.94 (m, 1H), 4.09-4.27 (m, 1H), 3.95 (d, 1H), 3.78 (d, 1H), 3.45-3.60 (m, 1H), 3.34-3.44 (m, 1H), 2.59-2.69 (m, 1H), 1.99-2.39 (m, 3H), 1.72-1.96 (m, 1H), 1.51-1.70 (m, 3H), 1.49 (s, 3H), 1.38-1.48 (m, 1H), 0.84 (s, 3H)
LC-MS (ESI POS): 550.18 MH+
$[\alpha]_D^{25}$=+221.2 (c=0.2, MeOH)

LEGEND

* NMR
s=singlet
d=doublet
t=triplet
q=quartet
dd=doublet of doublets
m=multiplet
br=broad ESI-POS=electrospray positive ionization
LC-MS=liquid chromatography-mass spectrometry Pharmacological Activity of the Compounds of the Invention In Vivo Studies Example 26

Lipopolysaccharide (LPS)-Induced Lung Neutrophilia

The potency and duration of action of the compounds described in the present invention were evaluated in vivo in an acute model of lung inflammation following a method described in *Am. J. Respir. Crit. Care Med.*, vol. 162, pp. 1455-1461, 2000, with minor modifications. The tests were performed on Sprague-Dawley male rats (200 g). Intratracheal instillation of LPS resulted in a statistically significant increase in neutrophil concentration in BALF, a hallmark of acute ongoing pulmonary inflammation. For the dose of glucocorticoid producing a 75% inhibition (ED75 dose) assessment test, compounds (0.01 to 3 µmoles/Kg of body weight) were administered intratracheally as suspension (0.2% Tween 80 in NaCl 0.9%) 1 hour before LPS challenge.

A dose-response curve of the inhibitory effect of the test compounds on LPS-induced lung neutrophilia was performed and the ED75 dose of glucocorticoid was taken as a measure of potency in this bioassay. The ED75 dose values for the compounds of the present invention were comprised between 0.62 and 1.62 µmoles/Kg of body weight.

In a second series of experiments, aimed at the evaluation of the duration of action, the compounds were administered as a suspension intratracheally, at the ED75 dose, at different time points (16 hours, 24 hours) before LPS challenge. Some compounds showed a percent of inhibition higher than 50% at 16 hours. The most interesting compounds were active (percent of inhibition higher than 50%) when administered 24 hours before LPS challenge.

In Vitro Studies

Example 27

Glucocorticoid Receptor (GR) Translocation Assay Protocol

A quantitative measurement of GR nuclear translocation of the compounds of the present invention was performed according to *ASSAY Drug Devel. Technol.*, vol. 4(3), pp. 263-272, 2006, through a novel cell-based GR-translocation assay in Enzyme Fragment Complementation (EFC) format developed by DiscoveRx (Fremont, Calif.).

In the absence of the glucocorticoid, the glucocorticoid receptor (GR) resides in the cytosol complexed with a variety of proteins including heat shock proteins. When a glucocorticoid diffuses through the cell membrane into the cytoplasm and binds to the glucocorticoid receptor (GR), it results in release of the heat shock proteins and the translocation into the nucleus where it modulates gene transcription.

The DiscoveRx assay uses EFC of b-galactosidase (b-gal) as an indicator of GR-translocation in engineered CHO-K1 biosensor cells. The enzyme acceptor (EA) fragment of b-gal resides in the nucleus, as designed through the use of a proprietary set of sequence additions and modifications. The small peptide enzyme donor (ED) fragment of b-gal was fused directly to the C-terminus of GR, and was localized in the cytoplasm in the absence of receptor signaling. Upon binding to a GR ligand, the complex translocates to the nucleus, where intact enzyme activity was restored by complementation and b-gal activity was detected.

CHO-K1 cells stably expressing NLS-enzyme acceptor fragment (EA) of b-gal and GR-enzyme donor (ED) fragment of b-gal were maintained in F12 medium (Invitrogen, Carlsbad, Calif.) at 37° C. under a humidified atmosphere containing 5% $CO_2$ and 95% air. The medium contained 10% FBS, 2 mM L-glutamine, 50 U/ml penicillin 50 µg/ml streptomycin, and 250 µg/ml hygromycin and 500 µg/ml G418 (Invitrogen).

GR-translocation was measured using the PathHunter Detection Kit containing cell membrane permeabilizing reagent and beta-gal substrate (DiscoveRx, Fremont, Calif.). All compounds were screened using varying concentrations ranging from $10^{-11}$ to $10^{-6}$ M. The assay was performed in 48-wells (105 cells/well). Incubation with screened compounds was performed at 37° C. for two hours. Detection was made by adding the detection buffer from the kit supplied by DiscoveRx and incubating at room temperature for one hour. Luminescence was detected by using a CENTRO LB 960 microplate reader (Berthold Technologies).

Statistical analysis and determinations of EC50s were performed by using Prism-version 3.0 Graphpad Software (San Diego, Calif.). The compounds assayed with the GR translocation assay displayed a EC50 comprised between 1 nM and 10 nM.

Example 28

Inhibition of LPS-Induced Nitric Oxide Production in Raw 264.7 Macrophages

An in vitro model based on macrophagic murine cell line RAW 264.7 was used for testing the anti-inflammatory effects of the corticosteroids of the present invention. During the inflammatory process, large amounts of nitric oxide (NO) were generated by the inducible isoforms of NO synthase (iNOS). Bacterial lipopolysaccharide (LPS) was commonly used in experimental settings to stimulate inflammatory responses in macrophages.

Cells were grown in a culture medium (RPMI supplemented with heat-inactivated 10% fetal calf serum, 2 mM glutamine, 100 U/ml penicillin, and 0.1 mg/ml streptomycin) without phenol red. Cell stimulation was elicited by incubating cells for 24 hours with LPS to final concentrations ranging from 100 ng/ml. Treatments with the compounds of the invention were carried out by adding such compounds vehicled in DMSO (0.1% final concentration) to the final desired concentrations 15 minutes before LPS exposure. As an index of nitric oxide production, the concentration of nitrite was measured in the conditioned media by using the Griess colorimetric reaction (*J. Neuroimmunol.*, vol. 150, pp. 29-36, 2004).

Statistical analysis and determinations of IC50s were performed by using Prism-version 3.0 Graphpad Software (San Diego, Calif.). The IC50 values tested on the compounds of the invention were comprised between 0.06 and 5.3 nM.

Example 29

[³H]-Dexamethasone Binding Assay

Glucocorticoid receptor affinity of the compounds described in the present patent application was evaluated utilising a radioligand binding assay as described in, "Receptor-ligand interactions, a practical approach," edited by IRL Press, Oxford University Press, pp. 247-253, 1992, which is incorporated herein by reference in its entirety. Human lymphoblast cell line IM-9 (ACC 117; DSMZ) has been used as source of the soluble glucocorticoid receptor and [³H]-dexamethasone (GE Healthcare; SA 34 µCi/nmol) as radioligand (*Invest. Ophtalmol. Vis. Sci.*, vol. 37, pp. 805-813, 1996). Non specific binding was evaluated in the presence of an excess of unlabelled beclomethasone (10 µM).

Binding experiments were performed in duplicate at radioligand concentration close to [³H]-dexamethasone $K_d$ value (1.5-2 nM). Samples were incubated at 0° C. for 16 to 18 hours in the dark. The reaction was terminated by adding a mixture of 2% activated carbon and 0.5% dextran in 10 mM Tris pH 7.4, 1 mM EDTA. After 10 minutes of incubation at 0° C., the samples were centrifuged for 10 minutes at 4,500 rpm. An aliquot of sample supernatants was placed in vials containing 3 ml of the scintillation cocktail Filtercount (PerkinElmer) and counted with a PerkinElmer 2500 TR beta counter. The IC50 values tested on the compounds of the invention were comprised between 0.5 and 2 nM.

Example 30

Kinetic Characterisation: Lung Retention

Lung retention was measured by means of two parameters: the $MRT_L$ (Mean Residence Time in the Lung), i.e. the residence of the compound in the lung, which is the time of the last measurable concentration of the compound in the rat lung after intratracheal administration of 1 µmol/kg, determined after lung homogenization, and the $C_{48}L/C_{0.5}L$ (%), i.e. the percentage of the amount of the compound in the lung 48 hours after intratracheal administration vs the amount the same compound in the lung 0.5 hours after administration.

$MRT_L$ and $C_{48}L/C_{0.5}L$ (%) are two meaningful and predictive parameters of the duration of a drug's effect after single dose pulmonary administration.

The compounds of the invention showed very slow lung elimination with $MRT_L$ higher than 20 hours and $C_{48}L/C_{0.5}L$ higher than 20%.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound represented by formula (I):

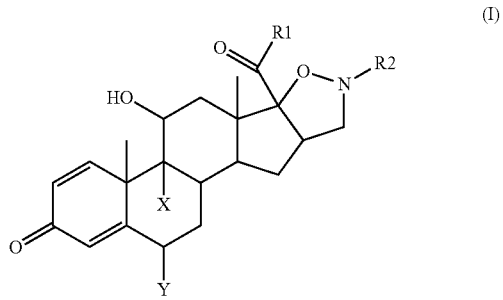

wherein
R1 is $(CH_2)_n$—Z—$(CH_2)_{n'}$—R4
  wherein
  n and n' are each independently 0, 1, or 2;
  Z is a single bond or is selected from the group consisting of S, O, CO, and NR3, wherein R3 is selected from the group consisting of H, straight or branched ($C_1$-$C_6$)alkyl, ($C_1$-$C_6$)haloalkyl, ($C_3$-$C_8$)cycloalkyl, aryl, aryl($C_1$-$C_6$)alkyl and heteroaryl, each of which are optionally substituted by CN;
  R4 is selected from the group consisting of:
    H, halogen, OH, SH, CN, $NH_2$;
    aryl($C_1$-$C_6$)alkyl, ($C_1$-$C_6$)alkylsulfonyl, ($C_1$-$C_6$)alkylcarbonyl, ($C_1$-$C_6$)alkylcarboxyl, O($C_1$-$C_6$)alkylcarboxyl, ($C_1$-$C_6$)alkylamide, and ($C_1$-$C_6$)alkoxy, each of which are optionally substituted by one or more oxo groups;
    ($C_1$-$C_6$)alkyl which may be optionally substituted by one or more substituents selected from the group consisting of a halogen atom, CN, OH, $NH_2$, $NO_2$, $CF_3$ and SH;
    ($C_2$-$C_6$)alkynyl;
    a mono-, bi- or tricyclic saturated or partially saturated or unsaturated ring, optionally substituted by one or more halogen atoms or oxo groups;
R2 is selected from the group consisting of
  H;
  $(CH_2)_m R5$,
    wherein R5 is heteroaryl optionally substituted with a substituent selected from the group consisting of oxo, OH, halogen, CN, $NH_2$, $NO_2$, aryl, ($C_1$-$C_6$)alkylsulfonyl, ($C_1$-$C_6$)alkoxy, ($C_1$-$C_6$)alkylthio, ($C_1$-$C_6$)alkylcarboxyl, ($C_1$-$C_6$)alkylamide, aryl ($C_1$-$C_6$)alkoxy, and ($C_1$-$C_6$)alkyl, each of which may be optionally substituted by one or more halogen atoms or COOH;
  $(CH_2)_p NR6R7$;
  $(CH_2)_p NR6COR7$;
  $(CH_2)_p NR6SO_2R7$;
  $(CH_2)_m CONR6R7$;
  $(CH_2)_m SO_2NR6R7$;
  $(CH_2)_m COR7$;
  $(CH_2)_p OR7$;
  $(CH_2)_m SO_q R7$;
    wherein R6 and R7 are independently H or are selected from the group consisting of straight or branched ($C_1$-$C_6$)alkyl, ($C_3$-$C_8$)cycloalkyl, aryl ($C_1$-$C_6$)alkyl and a saturated, partially saturated or unsaturated, optionally fused ring, each of which may be optionally substituted with one or more substituents selected from the group consisting of halogen, CN, oxo, $NH_2$, $NO_2$ and $(C_1-C_6)$alkyl; and $(CH_2)_pR8$ wherein R8 is selected from the group consisting of halogen, oxo, CN, OH, $NH_2$, $NO_2$; $(C_3-C_8)$cycloalkyl, and a saturated, partially saturated or unsaturated optionally fused ring, which may be optionally substituted by one or more substituents selected from the group consisting of halogen, CO, CN, $(C_1-C_6)$alkyl, $(C_1-C_6)$haloalkyl, $(C_1-C_6)$carboxyalkyl, $(C_1-C_6)$alkoxy, $(C_1-C_6)$haloalkoxy and $(C_1-C_6)$alkylsulfonyl; or R8 is aryl which is substituted by one or more substituents selected from the group consisting of halogen, CO, CN, $(C_1-C_6)$alkyl, $(C_1-C_6)$haloalkyl, $(C_1-C_6)$carboxyalkyl, $(C_1-C_6)$alkoxy, $(C_1-C_6)$haloalkoxy and $(C_1-C_6)$alkylsulfonyl;

wherein m and p are, each independently, 0 or an integer from 1 to 6, and q is 0, 1 or 2; and X and Y are each independently a halogen atom, or a pharmaceutically acceptable salt thereof.

2. A compound or pharmaceutically acceptable salt according to claim 1, wherein R4 is a mono-, bi- or tricyclic saturated or partially saturated or unsaturated ring selected from the group consisting of a $(C_3-C_8)$cycloalkyl, aryl, $(C_5-C_{10})$heterocycloalkyl, and heteroaryl, each of which may be optionally substituted by one or more halogen atoms or oxo groups.

3. A compound or pharmaceutically acceptable salt according to claim 1, wherein R6 and R7 are independently a saturated, partially saturated or unsaturated, optionally fused ring selected from the group consisting of aryl, $(C_5-C_{10})$heterocycloalkyl, and heteroaryl, each of which may be optionally substituted with one or more substituents selected from the group consisting of halogen, CN, oxo, $NH_2$, $NO_2$ and $(C_1-C_6)$alkyl.

4. A compound or pharmaceutically acceptable salt according to claim 1, wherein R8 is $(C_5-C_{10})$heterocycloalkyl, which may be optionally substituted by one or more substituents selected from the group consisting of halogen, CO, CN, $(C_1-C_6)$alkyl, $(C_1-C_6)$haloalkyl, $(C_1-C_6)$carboxyalkyl, $(C_1-C_6)$alkoxy, $(C_1-C_6)$haloalkoxy, and $(C_1-C_6)$alkylsulfonyl.

5. A compound according to claim 1 represented by formula (I'):

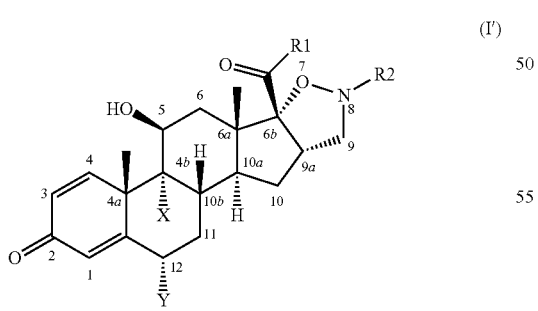

wherein the carbon atom at the 4a position has the (R) configuration, the carbon atom at the 4b position has the ((R) configuration, the carbon atom at the 5 position has the (S) configuration, the carbon atom at the 6a position has the (S) configuration, the carbon atom at the 6b position has the (R) configuration, the carbon atom at the 9a position has the (S) configuration, the carbon atom at the 10a position has the (S) configuration, the carbon atom at the 10b position has the (S) configuration, and the carbon atom at the 12 position has the (S) configuration, or a pharmaceutically acceptable salt thereof.

6. A compound or pharmaceutically acceptable salt according to claim 1, wherein

R1 is $(CH_2)_n$—Z—$(CH_2)_{n'}$—R4, wherein n is 0 or 1;

Z is a single bond or is selected from the group consisting of S, O and NR3, wherein R3 is H or $(C_1-C_6)$alkyl;

n' is 0, 1 or 2; and

R4 is selected from the group consisting of H, halogen, CN, OH; $(C_1-C_6)$alkyl, optionally substituted by one or more substituents selected from the group consisting of a halogen atom, CN, OH, $NH_2$, $NO_2$, $CF_3$ and SH; aryl$(C_1-C_6)$alkyl, $(C_1-C_6)$alkynyl, $(C_1-C_6)$alkylsulfonyl, $(C_1-C_6)$alkylcarbonyl, $O(C_1-C_6)$alkylcarbonyl, $(C_1-C_6)$alkylamide, $(C_1-C_6)$alkylcarboxyl, $(C_5-C_{10})$heterocycloalkyl and heteroaryl, each which may be optionally substituted by one or more oxo groups.

7. A compound or pharmaceutically acceptable salt according to claim 4, wherein R4 is selected from the group consisting of methyl, ethyl, benzothiazole, benzooxazole, tetrahydrofuran, tetrahydropiran tetrahydropyran, methylsulfonyl, methylcarbonyl, chlorine, fluorine, trifluoromethyl, methylcarboxyl, ethylcarboxyl, methoxy, ethoxy, trifluoromethyl, and butynyl.

8. A compound or pharmaceutically acceptable salt according to claim 7, wherein R3 is H or methyl.

9. A compound or pharmaceutically acceptable salt according to claim 1, wherein

R2 is H or is selected from the group consisting of $(CH_2)_mR5$, wherein m is 1 or 2, and R5 is heteroaryl optionally substituted by a group selected from halogen, CN, OH, $CF_3$, $(C_1-C_6)$alkyl, $(C_1-C_6)$haloalkyl, $(C_1-C_6)$alkoxy, $(C_1-C_6)$alkylsulfonyl and aryl;

$(CH_2)_mCONR6R7$, wherein m is O, R6 is $(C_1-C_6)$alkyl, and R7 is aryl;

$(CH_2)_mCOR7$, wherein m is 1, and R7 is aryl, heteroaryl or $(C_5-C_{10})$heterocycloalkyl;

$(CH_2)_pOR7$, wherein p is 2 and R7 is aryl or aryl$(C_1-C_6)$alkyl;

$(CH_2)_mSO_qR7$, wherein m is 0 or 2, q is 0 or 2, and R7 is $(C_1-C_6)$alkyl or aryl; and $(CH_2)_pR8$, wherein p is 1, 2 or 3 and R8 is selected from the group consisting of $(C_5-C_{10})$heterocycloalkyl, optionally substituted by one or more substituents selected from the group consisting of halogen, oxo, CN, OH, $CF_3$, $(C_1-C_6)$alkyl, $(C_1-C_6)$haloalkyl, $(C_1-C_6)$alkoxy, $(C_1-C_6)$haloalkoxy, $(C_1-C_6)$alkylcarboxyl and $(C_1-C_6)$alkylsulfonyl; or R8 is aryl which is substituted by one or more substituents selected from the group consisting of halogen, CO, CN, $(C_1-C_6)$alkyl, $(C_1-C_6)$haloalkyl, $(C_1-C_6)$carboxyalkyl, $(C_1-C_6)$alkoxy, $(C_1-C_6)$haloalkoxy and $(C_1-C_6)$alkylsulfonyl.

10. A compound or pharmaceutically acceptable salt according to claim 9, wherein R2 is selected from the group consisting of thiophenyl, pyridyl, imidazolyl, thiazolyl, benziloxyethyl, phenoxyethyl, isoxazolyl, benzoyl, furancarbonyl, methanesulfonyl, dihydropyridinmethyl, a methylphenylamide radical, a cyclopentenone radical, a benzofuran radical, a furan radical, and a dihydrobenzodioxin radical.

11. A compound or pharmaceutically acceptable salt according to claim 1, wherein X and Y are both fluorine atoms.

12. A compound or pharmaceutically acceptable salt according to claim 5, wherein X and Y are both fluorine atoms.

13. A compound or pharmaceutically acceptable salt according to claim 6, wherein X and Y are both fluorine atoms.

14. A compound or pharmaceutically acceptable salt according to claim 9, wherein X and Y are both fluorine atoms.

15. A pharmaceutical composition, comprising a compound or pharmaceutically acceptable salt according to claim 1 and one or more pharmaceutically acceptable carriers or excipients.

16. A combination, comprising a compound or pharmaceutically acceptable salt according to claim 1 and one or more active ingredients selected from the group consisting of a beta2-agonist, an antimuscarinic agent, a corticosteroid, a mitogen-activated protein kinase (P38 MAP kinase) inhibitor, a nuclear factor kappa-B kinase subunit beta (IKK2) inhibitor, a human neutrophil elastase (HNE) inhibitor, a phosphodiesterase 4 (PDE4) inhibitor, a leukotriene modulator, a non-steroidal anti-inflammatory agents (NSAID), and a mucus regulator.

17. A process for the preparation of a compound or pharmaceutically acceptable salt according to claim 1, wherein R1 is —(CH$_2$)$_n$—Z—(CH$_2$)$_{n'}$—R4, wherein n is 1, said process comprising:
(a) reacting a compound represented by formula (VI):

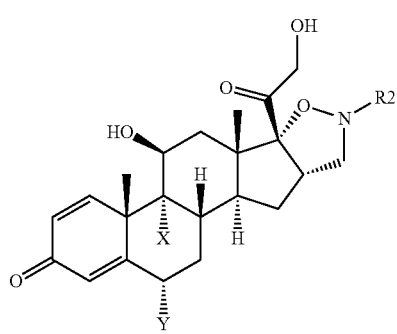
(VI)

with methanesulfonyl chloride or p-toluenesulfonyl chloride to obtain a compound represented by formula (XI)

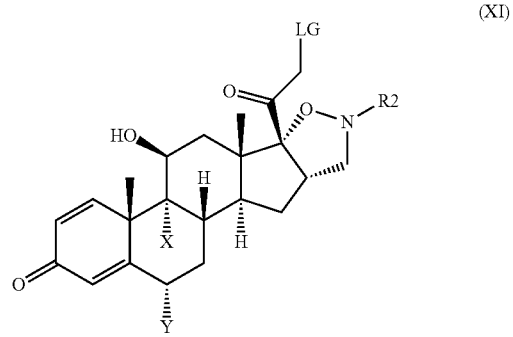
(XI)

wherein LG may be displaced by a nucleophile.

18. A process for the preparation of a compound or pharmaceutically acceptable salt according to claim 1, wherein R1 is (CH$_2$)$_n$—Z—(CH$_2$)$_{n'}$—R4 wherein n is 0, said process comprising:
(a) oxidizing a compound represented by formula (VI):

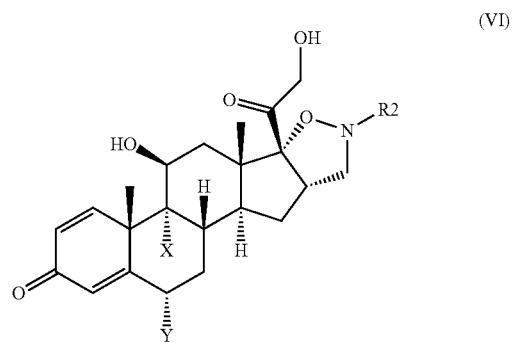
(VI)

to obtain a compound represented by formula (XII):

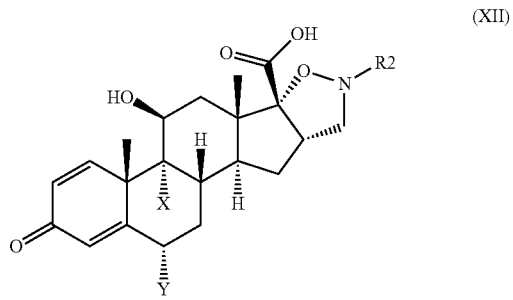
(XII)

(b) treating said compound represented by formula (XII) with one or more equivalents of an acid activating agent and then with a nucleophile.

19. A method for the treatment of asthma or chronic obstructive pulmonary disease, said method comprising administering a compound or pharmaceutically acceptable salt according to claim 1 to a subject in need thereof.

20. A method for the treatment of asthma, chronic obstructive pulmonary disease (COPD), allergic rhinitis, rheumatoid arthritis, inflammatory bowel disease or an autoimmune disease, said method comprising administering a compound or pharmaceutically acceptable salt according to claim 1 to a subject in need thereof.

* * * * *